United States Patent
Downs

(10) Patent No.: US 6,964,867 B2
(45) Date of Patent: Nov. 15, 2005

(54) METHOD AND APPARATUS FOR PERFORMING MULTIPLE PROCESSING STEPS ON A SAMPLE IN A SINGLE VESSEL

(75) Inventor: Robert Charles Downs, La Jolla, CA (US)

(73) Assignee: IRM, LLC, Hamilton (BM)

(*) Notice: Subject to any disclaimer, the term of this patent is extended or adjusted under 35 U.S.C. 154(b) by 485 days.

(21) Appl. No.: 10/101,491

(22) Filed: Mar. 18, 2002

(65) Prior Publication Data

US 2002/0164653 A1 Nov. 7, 2002

Related U.S. Application Data

(63) Continuation-in-part of application No. 09/810,020, filed on Mar. 16, 2001.

(51) Int. Cl.[7] .................... C12M 1/00; C12P 1/00; C12P 21/06; A61K 7/38; A01N 43/00
(52) U.S. Cl. ................ 435/289.1; 435/41; 435/69.1; 424/68; 424/418
(58) Field of Search ............. 424/418, 68; 435/69.1, 435/289.1, 41

(56) References Cited

U.S. PATENT DOCUMENTS

| | | | |
|---|---|---|---|
| 4,490,436 A | * | 12/1984 | Kawakami et al. .......... 428/403 |
| 5,871,248 A | | 2/1999 | Okogbaa et al. |
| 5,945,798 A | | 8/1999 | Stagnitto et al. |
| 6,197,517 B1 | | 3/2001 | Roberts |
| 6,296,673 B1 | | 10/2001 | Santarsiero et al. |

FOREIGN PATENT DOCUMENTS

| WO | WO 97/15588 A1 | 5/1997 |
|---|---|---|
| WO | WO 02/062484 A1 | 8/2002 |
| WO | WO 02/063027 A1 | 8/2002 |
| WO | WO 02/068157 A2 | 9/2002 |

OTHER PUBLICATIONS

Cole Parmer Catalog 1999/2000, pp. 228–229, 406, 444–445.*

* cited by examiner

*Primary Examiner*—Jon Weber
*Assistant Examiner*—Kailash C. Srivastava
(74) *Attorney, Agent, or Firm*—Timothy L. Smith; Christopher C. Sapponfield; Quine Intellectual Property Law Group, P.C.

(57) ABSTRACT

A method is provided for determining crystallization conditions for a protein, the method comprising: performing in a same fermentation apparatus 2 or more separate fermentations where each fermentation comprises cells expressing a protein to be purified and has a fermentation volume of less than 500 mL; purifying the expressed protein from the separate fermentations; and determining crystallization conditions for the purified protein by submicroliter crystallization experiments.

16 Claims, 33 Drawing Sheets

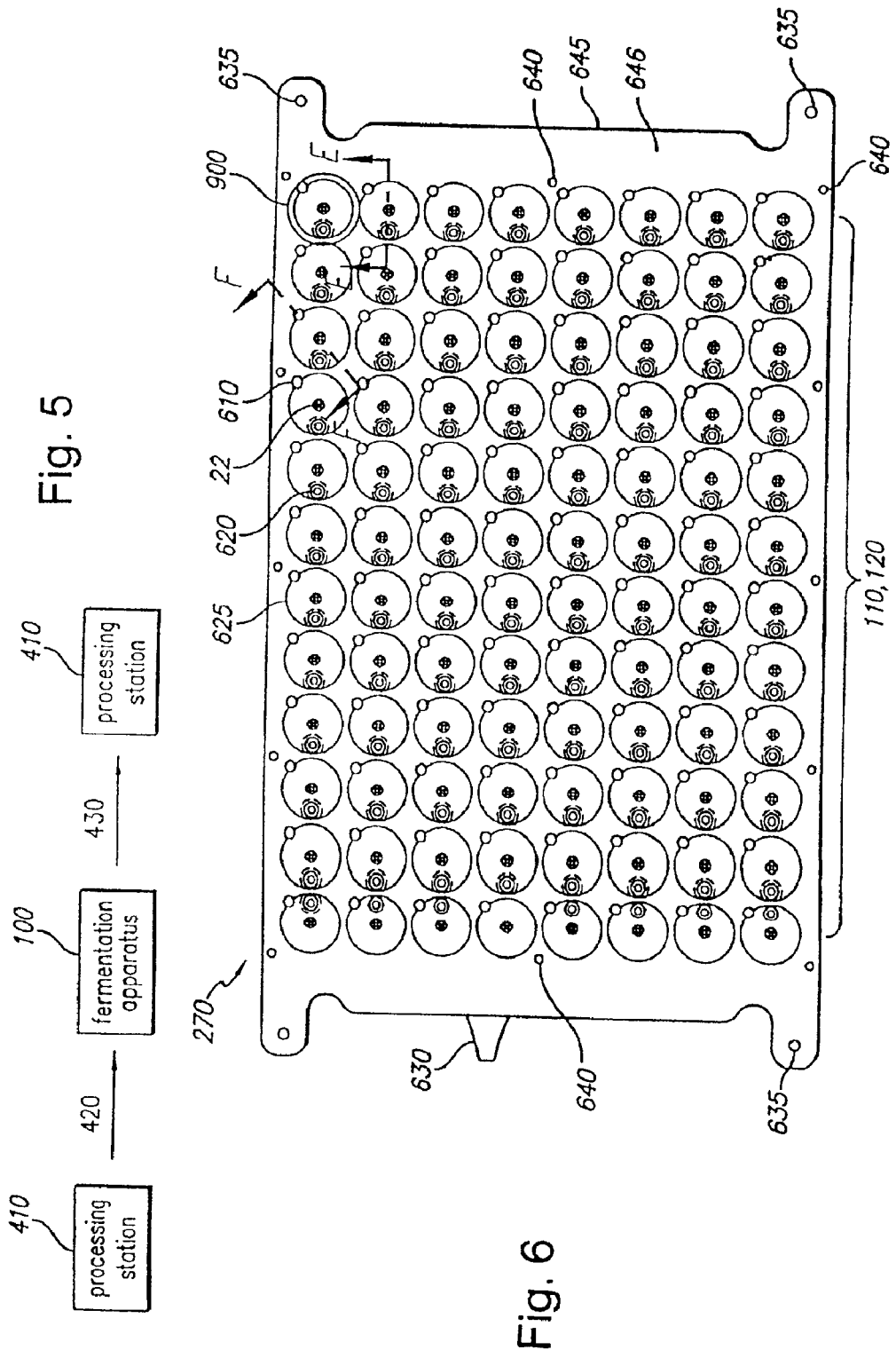

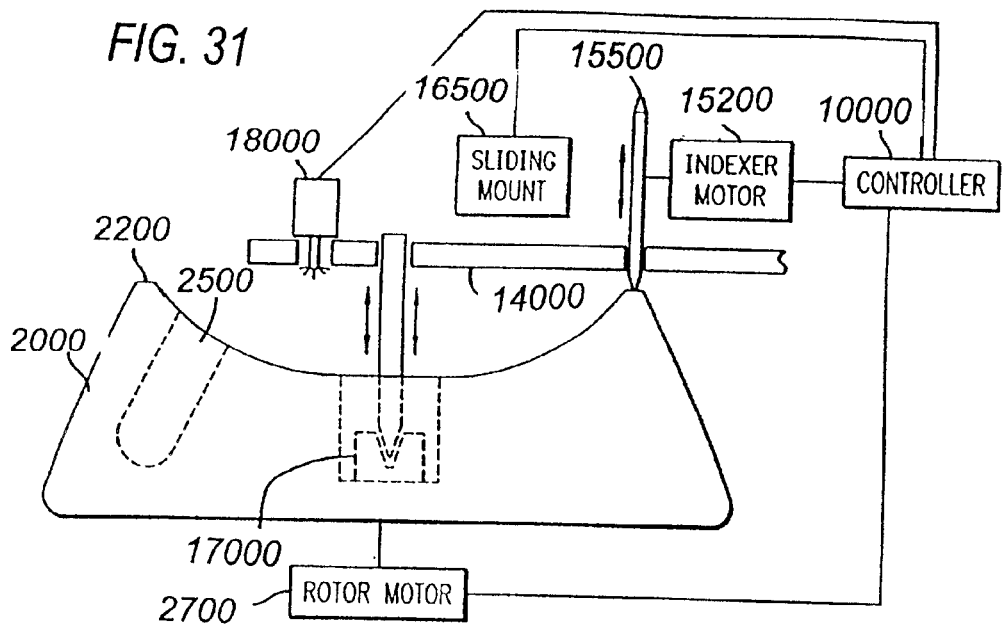

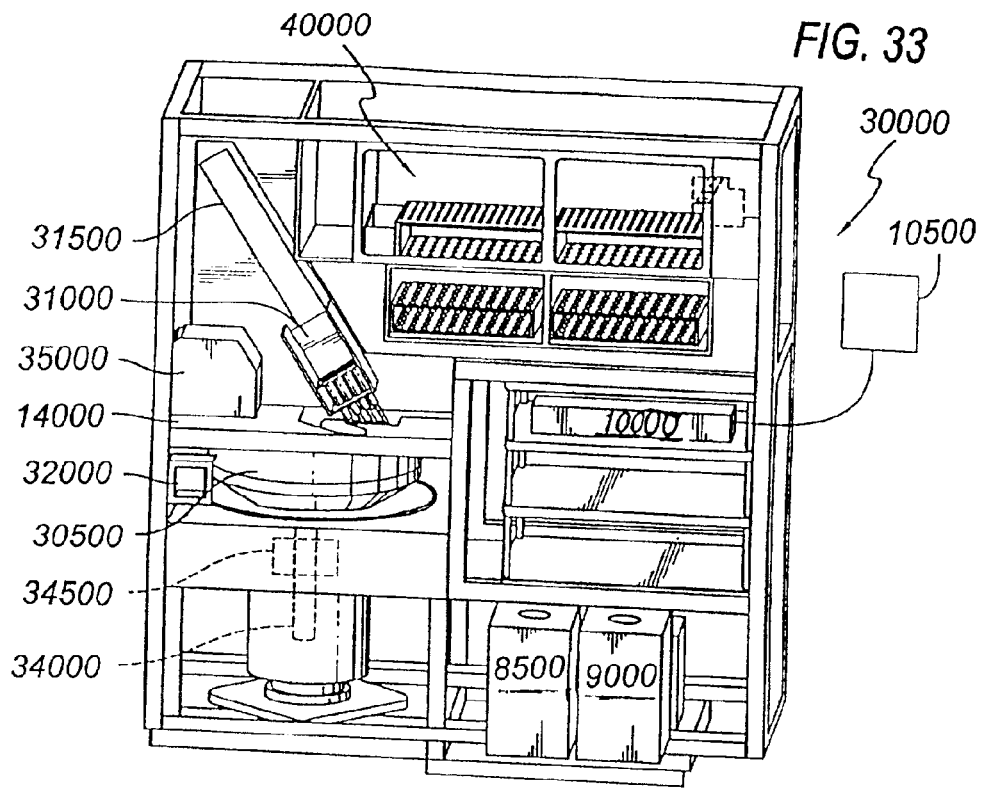
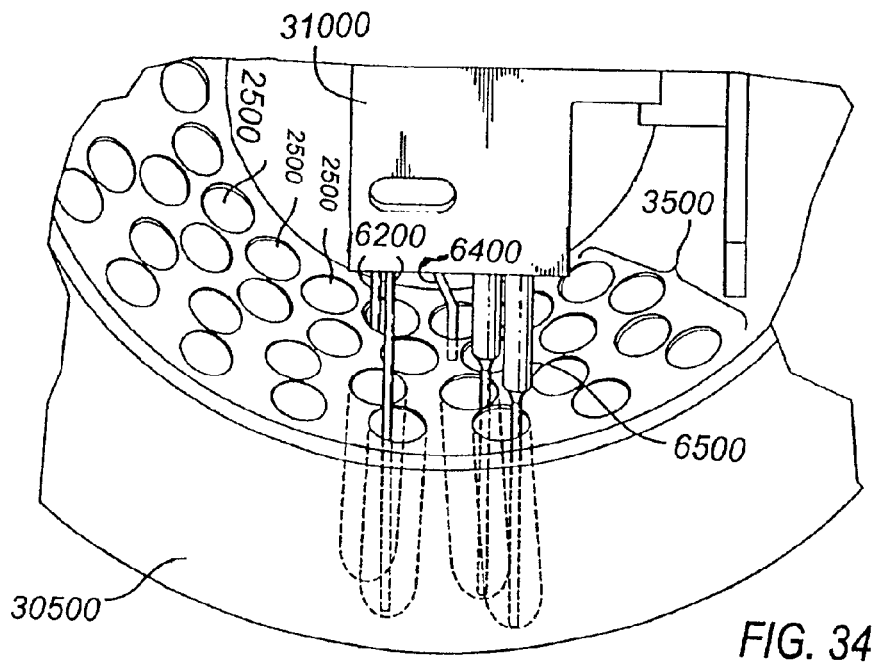
FIG. 33
FIG. 34

METHOD AND APPARATUS FOR PERFORMING MULTIPLE PROCESSING STEPS ON A SAMPLE IN A SINGLE VESSEL

CROSS-REFERENCES TO RELATED APPLICATIONS

This application is a continuation-in-part of U.S. patent application Ser. No. 09/810,020, filed on Mar. 16, 2001, entitled "METHOD AND APPARATUS FOR PERFORMING MULTIPLE PROCESSING STEPS ON A SAMPLE IN A SINGLE VESSEL," by Downs, the disclosure of which is incorporated by reference. The present application claims priority to and the benefit of this related application, pursuant to 35 U.S.C. §119, 35 U.S.C. §120, and any other applicable statute or rule.

COPYRIGHT NOTIFICATION

Pursuant to 37 C.F.R. § 1.71(e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

STATEMENT AS TO RIGHTS TO INVENTIONS MADE UNDER FEDERALLY SPONSORED RESEARCH AND DEVELOPMENT

Not Applicable.

FIELD OF THE INVENTION

The present invention relates generally to a method and apparatus for performing multiple processing steps on a sample in a single vessel. More specifically, the present invention relates to a method and apparatus useful, for example, in biomedical and biotechnology processes such as an automated centrifugation and fermentation process.

BACKGROUND OF THE INVENTION

Processing of a sample such as a biological sample for fermentation and centrifugation typically requires use of more than one vessel. For example, fermentation is carried out in one vessel and then the sample must be transferred to another vessel before the sample can be placed in a centrifuge for further processing. In addition, such multiple process procedures may require significant manual intervention to transfer the sample from one vessel to another and from one processing device or station to another.

Fermentation is a key technology in many fields and industries and is performed both on a mass production scale and on an experimental, bench top scale. For example, fermentation systems are used for the production of a large number of products such as antibiotics, vaccines, synthetic biopolymers, synthetic amino acids, and proteins. Fermentation technology is integral in the production of recombinant proteins using biological organisms such as *E. coli* and many other cell cultures. For example, production of commercial pharmaceuticals such as recombinant insulin (Eli Lilly), erythropoietin (Amgen), and interferon (Roche) all involve fermentation as an essential step.

Rapid advances in biotechnology have enabled the development of high throughput alternatives to traditional laboratory bench top processes. Unfortunately, fermentation methods have not been amenable to automation because limits in current fermentation technology prevent the uninterrupted processing flow that characterizes automated high throughput systems. Existing fermentation systems typically involve multiple handling steps by either a batch processing method or a continuous processing method.

Current production scale batch processes involve first fermenting in large scale, bulk fermentation vessels, then processing the fermentation medium to isolate the desired fermentation product, followed by transferring this product into the production stream for further processing, and finally cleaning the fermentation apparatus for the next batch. In a large-scale batch culture, it is generally necessary to provide a high initial concentration of nutrients in order to sustain cell growth over an extended time. As a result, substrate inhibition may occur in the early stages of cell growth and then may be followed by a nutrient deficiency in the late stages of fermentation. These disadvantages result in sub-optimal cell growth rates and fermentation yields. Another disadvantage of this method lies in the need to individually dispense the fermentation products from the bulk fermentation apparatus into separate sample vessels for further processing. Thus, by producing the fermentation product on a bulk scale, the fermentation product is not immediately available for automated processing. Further disadvantages include the decreased efficiency of both transferring the material to another sample vessel, as well as cleaning and sterilizing the fermentation apparatus for the next batch. These disadvantages result in increased production costs, inefficient production times and decreased yields.

Continuous batch processes involve siphoning off the fermentation product from the bulk fermentation vessel and continuously adding nutrients to the fermentation medium according to a calculated exponential growth curve. This curve, however, is merely an approximation that does not accurately predict cell growth in large, industrial scale quantities of fermentation medium. Consequently, due to the unpredictable nature of large-scale fermentation environments, experienced personnel are required to monitor the feeding rate very closely. Changes in the fermentation environment may result in either poisoned fermentation products being siphoned off into the production stream or sub-optimal production yields due to starved fermentation mediums. As a further disadvantage, unpredictable fermentation product yields affect the accuracy of subsequent processing steps. For example, when the fermentation yield decreases, the amount of aspirating, the amount of reagent dispensed, or the centrifuge time is no longer optimized, or even predictable. Frequent or continuous monitoring of the fermentation process and adjustment of the fermentation conditions is often not practicable or efficient in a production scale process.

Fermentation remains a key-processing step in a number of industries, particularly in biotechnology industries, and thus a need exists for incorporating fermentation processes into current multiple process systems, such as automated high throughput systems. A process that produces a precise, known, and repeatable amount of unpoisoned fermentation product with limited human interaction or sample vessel transfer is essential to integrating fermentation into modern production processes.

Centrifugation, like fermentation, is a key technology in many fields and industries. It may be performed on a mass production scale or an experimental, bench top scale. For example, centrifuges are used in a wide variety of disciplines, including the chemical, agricultural, medical and biological fields. In particular, centrifuge technology is integral to chemical syntheses, cell separations, radioactive isotope analyses, blood analyses, assaying techniques, as well as many other scientific applications.

Estimates stemming from the recent completion of the human genome sequencing projects are that the human genome probably comprises more than 40,000 genes. This highlights one important use of centrifuge technology, namely, the determination of each gene's function, which has become of paramount importance. Because each gene likely encodes at least one protein, more than 40,000 proteins must be expressed and isolated to understand the function of each gene in the human genome. Centrifugation is an important step in isolating and separating proteins, but protein isolation frequently requires several labor intensive and time-consuming sequential procedures that often involve more than one centrifugation step for each isolation process.

Particularly for commercial applications, these proteins and other products utilizing centrifuge technology must be synthesized analyzed or isolated on a production scale. Likewise, rapid advances in laboratory equipment have transitioned traditional laboratory bench top processes to more automated high-throughput systems. Unfortunately, limits in current centrifuge technology prevent the uninterrupted processing flow that characterizes automated high throughput systems.

These and other disadvantages are highlighted in a typical protein isolation process. Generally, a sample is centrifuged, removed from the centrifuge and a portion of the sample is removed, often by aspiration, from the sample at a separate processing station. At yet another processing station, a reagent is often dispensed into the remaining sample, followed by sonication in a separate sonication device (also at another processing station). Once the contents of the sample have been sonicated, the sample is placed back in the centrifuge and undergoes another centrifugation step. Frequently, this centrifugation-aspiration-dispensing-sonication-centrifugation cycle is repeated more than once for a particular protein isolation.

This cycle and all its drawbacks are also representative of many other applications involving centrifugation. Disadvantageously, typical sonication and centrifugation steps are not amenable to automated processing flows because of the need to physically transfer large numbers of samples to and from various processing stations. For example, in the example described above, a sample must be moved from a centrifugation station to an aspirating station, to a dispensing station, to a sonication station, and back to a centrifugation station. Unfortunately, this cycle may be repeated several times before a particular protein or other targeted material is isolated. Accordingly, the labor-intensive nature of the isolation process poses severe time constraints and cost increases, particularly when integration of the centrifuge step or the sonication step into an automated multiple process system is currently unavailable.

As centrifugation remains a key processing step in a number of industries, and particularly in biotechnology industries, a critical need exists for incorporating centrifugation processes into current multiple process systems such as automated high throughput systems.

SUMMARY OF THE INVENTION

It is therefore an object of the present invention to provide a method and apparatus for performing multiple processing steps on a sample in a single vessel. It is a separate object of the present invention to minimize the time, cost, clean up and labor associated with conventional fermentation, centrifugation and other processing methods and devices.

The present invention alleviates to a great extent the disadvantages of the known methods and apparatus for performing processing steps such as fermentation and centrifugation on a sample. Accordingly, the present invention improves the accuracy and precision in performing multiple processing steps on a sample.

An important feature of automated high throughput systems is their ability to perform multiple different experiments in a highly parallel manner. The present invention addresses this issue by not only facilitating the processing of a single sample by allowing it to undergo multiple processing steps in a single vessel, the present invention allows such multiple single vessel processing steps to be performed in a highly parallel manner. For example, according to the present invention, 2, 3, 4, 5, 10, 20, 50 or more different samples can be processed in parallel where each sample undergoes multiple processing steps in a single vessel. For example, the parallel processing of a 8×12 array of samples is described herein by way of illustration.

Briefly, the present invention provides a method and apparatus for performing multiple processing steps on a sample in a single vessel. Thus, for example, nutrients may be added to a sample in a vessel, the sample in the vessel may be fermented at one station, and the sample in the vessel may be placed in a centrifuge at a separate station without having to transfer the sample to another vessel.

Thus, one aspect the present invention provides a method of processing a sample in a single vessel, the method comprising performing multiple automated processing steps on the sample in the vessel, wherein one of the automated processing steps is automated fermentation of the sample in the vessel. An automated processing step is performed entirely by a machine or at most with operator input through an operator interface. The automated processing steps may occur before, after or before and after the automated fermentation. The automated processing method is preferably performed in parallel on multiple samples (e.g., 2, 3, 4, 5, 10, 20, 50 or more different samples).

Thus, the present invention provides a method comprising: performing a plurality of fermentations, each fermentation in a different sample vessel; and performing a further processing step on the plurality of fermented samples where each sample is retained in the same sample vessel during the fermentation and processing steps.

In a preferred embodiment the present invention is used in conjunction with the methods, devices and systems for fermentation described in U.S. patent application entitled "Multi-Sample Fermentor and Method of Using Same" Ser. No. 09/780,591, filed Feb. 8, 2001, and in U.S. patent application Ser. No. 10/071,842 entitled "Multi-Sample Fermentor and Method of Using Same," filed Feb. 8, 2002, which are incorporated herein by reference in their entirety for all purposes. The present invention also preferably may be used in conjunction with the methods, devices and systems for centrifugation described in U.S. patent application entitled "Automated Centrifuge and Method Of Using Same," Ser. No. 09/780,589, filed Feb. 8, 2001, and in international patent application Ser. No. 10/071,877 entitled "Automated Centrifuge and Method Of Using Same," filed Feb. 8, 2002, which are incorporated herein by reference in their entirety for all purposes. The sample in a vessel may be moved, for example from a fermentor to a centrifuge, in a preferred embodiment by a robotic gripper as described in U.S. patent application entitled "Gripper Mechanism," Ser. No. 09/793,254, filed Feb. 26, 2001, and in international patent application Ser. No. PCT/US02/06096 entitled "Gripping Mechanisms, Apparatus, and Methods," filed Feb. 26, 2002, which are incorporated herein by reference in their entirety for all purposes.

In a preferred embodiment, a sample comprising organisms that express a particular protein to be produced is fermented, centrifuged and then several additional downstream processing steps may be performed, either in or out of the sample vessel in order to isolate and purify the protein. In addition, once purified, the protein may be crystallized to form a crystallized protein. Once crystallized, crystals of the protein may be bombarded with x-rays in order to determine a 3-dimensional structure of the protein.

U.S. Pat. No. 6,296,673 entitled "Methods and Apparatus for Performing Array Microcrystallizations" describes performing protein crystallizations where a protein solution of less than 1 microliter is used per crystallization experiment. This patent is incorporated herein by reference in its entirety. A feature of the present invention is its ability to be used synergistically with array microcrystallizations such as those described in U.S. Pat. No. 6,296,673. More specifically, by being able to crystallize proteins from a protein solution of less than 1 microliter, less protein is needed to perform crystallization experiments to identify suitable crystallization conditions for a protein. As a result, less protein needs to be expressed, isolated and purified to feed such crystallization experiments. Accordingly, the highly parallel processes of the present invention allow a protein to be expressed in separate fermentations, isolated, purified and then ultimately crystallized with far less labor.

In one embodiment, a method for purifying a protein is provided that comprises: fermenting 2, 3, 4, 5, 10, 20 or more separate fermentations of the protein, purifying the protein from the fermentations so that the purified protein can be used to perform crystallization experiments for the protein. As will be described herein, the fermentations are designed to have relatively small volumes, e.g., 500 ml, 250 ml, 100 ml or less fermentation volumes. Similarly, the vessels within which the fermentations are performed are also relatively small volumes (e.g., 500 ml, 250 ml, 100 ml or less). Despite the small volumes of these fermentations, the fermentations of the protein performed in this manner yields a sufficient amount of protein to later isolate and then purify the protein to conduct successful crystallization trials. Advantageously, because multiple of the fermentation, protein isolation and purification steps can be performed in parallel and in at least a partially automated manner, the amount of labor required to produce a sufficient amount of purified protein to conduct protein crystallization experiments is significantly reduced.

Certain companies, such as Syrrx, Inc. of San Diego, Calif., are making attempts to perform high throughput crystallizations. Such efforts require large numbers of different proteins to be recombinantly expressed and purified prior to crystallization. The present invention provides automated, highly parallel technology that makes such efforts practical in view of the extraordinary labor demands that would otherwise be required.

Advantages associated with the present invention include a reduced amount of time required to perform the multiple process steps on the sample. In addition, the present invention provides a reduced amount of clean up, disposal, and labor, thereby reducing the overall cost of operation. Another advantage realized by the present invention is an increased accuracy, thereby increasing the reliability of the results of the multiple process method.

One advantage of the present invention is that the sample vessels are capable of undergoing multiple process steps before, during or after fermentation. Each of these sample vessels has a gripping surface that a transporter uses to transfer the sample vessel to another processing station. These sample vessels are constructed such that post- and pre-fermentation steps may be conducted directly on the sample in the sample vessel. The compatibility of the sample vessel with other processing steps in the production eliminates increased production costs incurred both from first transferring fermentation product from a bulk fermentation vessel to a sample processing vessel, and then cleaning and sterilizing the bulk fermentation vessel. Further, eliminating a transfer step increases the efficiency of the overall process because of the decreased production time in not having to perform an extra transfer step and the increased yield from not losing any fermentation product in a transfer step.

Another advantage is that the fermentation apparatus may also be used in non-production scale environments where uninterrupted process flows are desirable. For example, the fermentation apparatus may be adapted to bench top processes on an experimental scale. This provides a further advantage of easily modifying the process later to an industrial scale by eliminating the step of redesigning the fermentation conditions that is usually required when scaling up a bench top process to a production scale process. Because the present invention utilizes smaller scale fermentation volumes, the unpredictability and unmanageability of bulk fermentation volumes is eliminated while still providing production scale quantities of fermentation product. A fermentation method or apparatus made according to the present invention may be utilized in any production, analysis, or system requiring multiple process steps.

Disadvantages resulting from increased production costs incurred from transferring fermentation product from a bulk fermentation vessel to a processing sample vessel are thus eliminated, as are the costs of cleaning and sterilizing a bulk fermentation apparatus for the next batch. According to the present invention, only the sample vessels will be cleaned at the end of the production process. In addition, valuable time is saved and yields are increased by not having to transfer a bulk fermentation product to a sample vessel that would be amenable to high throughput processing.

A further advantage is that calculation of exponential growth curves is more precise and reliable. This advantage is created because the fermentation volumes of the sample vessels are smaller than current production scale bulk fermentation systems. As a result, the nutrient feed may be more accurately optimized, resulting in the production of known and repeatable yields of fermentation product. In addition, each sample vessel may be equipped with sensors that transmit data to a controller, enabling the apparatus to respond to suboptimal fermentation conditions by appropriately adjusting environmental parameters. The present invention uses relatively small volumes by fermenting in a sample vessel and thereby eliminates the erratic fluctuations in environmental conditions that lead to unpredictability of fermentation growth yields. As a result, for example, the amount of aspirating, the amount of reagent dispensed, or the centrifuge time may now be predicted and optimized, leading to a more efficient and reliable system. The steps of monitoring of the fermentation process to determine the fermentation yield and monitoring or adjusting further processes downstream, such as dispensing or aspirating steps based on the amount of fermentation product, are eliminated when using smaller volume fermentation batches.

Another added advantage stems from the size of the fermentation batches. Because these fermentation batches are relatively small compared to the bulk fermentation vessels currently being used, known amounts of nutrients may be calculated to optimize the fermentation yield and known fermentation yields may be calculated on a predictable and repeatable basis. This reliability in calculating a fermentation yield enables the optimization of centrifuge times, dispensing accurate amounts of reagent, and aspirating accurate amounts of liquid that is otherwise not possible in current bulk fermentation systems. Without a reliable and repeatable fermentation product yield, it is very difficult to engineer a high throughput system involving many processing steps where each processing step, such as the amount dispensed or the time centrifuged, would otherwise vary according to a fluctuating fermentation yield. The present invention overcomes these difficulties by providing predictable and repeatable fermentation yields upon which to calculate and optimize subsequent processing steps, such as those used in a high throughput system.

These and other features and advantages of the present invention will be appreciated from review of the following detailed description of the invention, along with the accompanying figures in which like reference numerals refer to like parts throughout.

BRIEF DESCRIPTION OF THE DRAWINGS

FIG. 5 is a block diagram showing the use of a fermentation system within a multiple process procedure in accordance with the present invention.

FIG. 6 is a schematic illustrating a bottom view of a gas arrangement in accordance with the present invention.

FIG. 31 is a side elevation view of a rotor constructed according to the present invention and a schematic block diagram of associated components of the present invention.

FIG. 32 illustrates one image projected on an operator interface illustrated in FIG. 29.

FIG. 33 is a perspective view of an alternative embodiment of the automated centrifuge of the present invention.

FIG. 34 is a perspective view of a section of a rotor employed in the centrifuge illustrated in FIG. 33.

Figure 1:
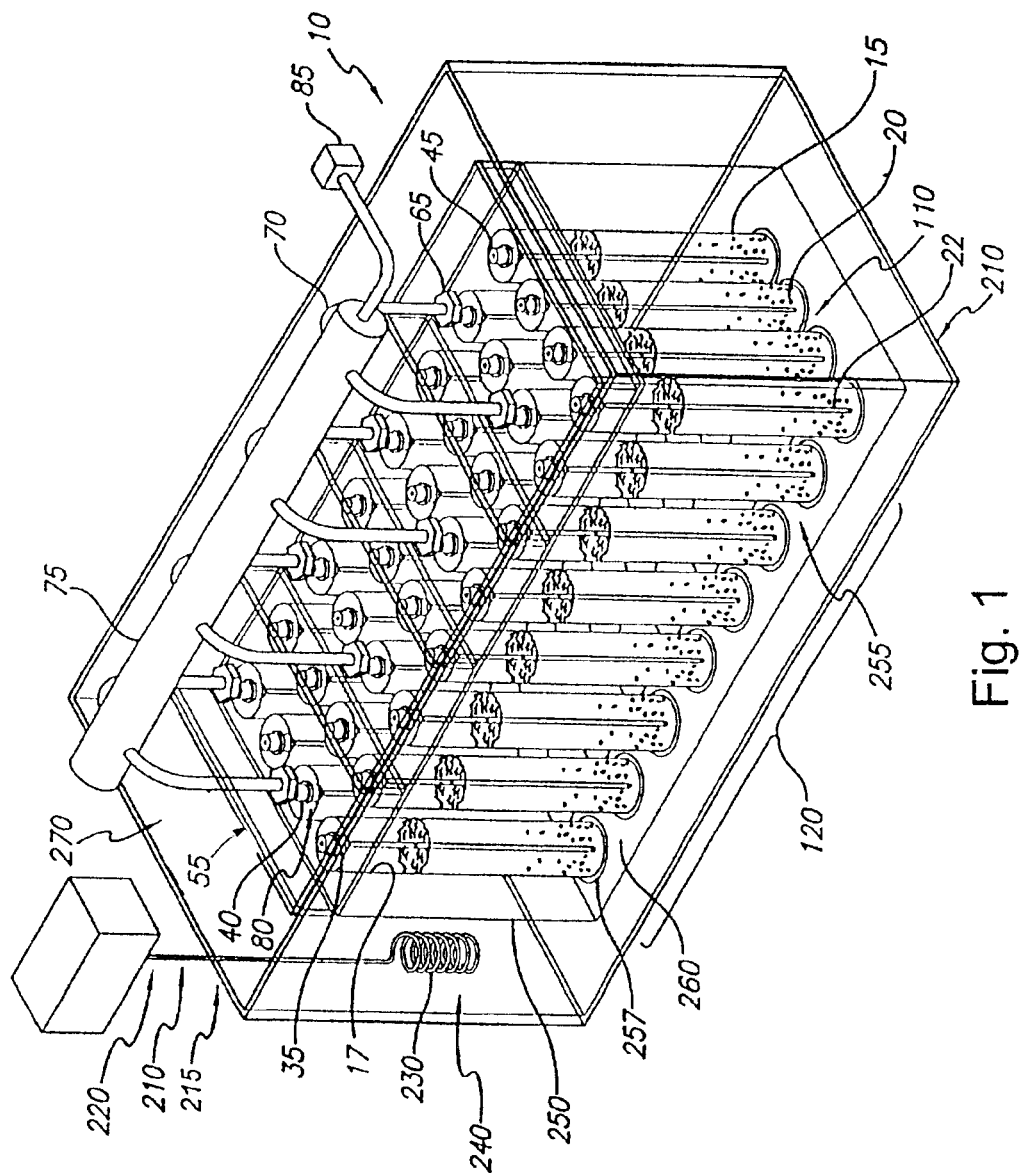
FIG. 1 is a schematic showing a perspective view of a fermentation apparatus in accordance with the present invention.

Some or all of the Figures are schematic representations for purposes of illustration and do not necessarily depict actual relative sizes or locations of the elements shown.

DETAILED DESCRIPTION OF THE INVENTION

I. Overview of the Invention

The present invention relates methods and devices which allow for multiple different sample processing steps, e.g., including fermentation, to be performed in the same sample vessel. The present invention also relates methods and devices which provide for automation for performing these different sample processing steps.

In one embodiment, a method is provided for fermenting a plurality of samples, comprising: providing a plurality of sample vessels each holding a fermentation sample in a sample carrier; fermenting the fermentation samples in the plurality of sample vessels in the carrier; and transporting the samples once fermented to a processing station where the samples may be further processed. Further processing may include, for example, centrifugation, sonication, and/or protein purification. Optionally, transporting the samples once fermented to a processing station is performed by transporting the samples in the same sample carrier as was used for the fermentation. This allows a series of samples to be fermented and then transported together.

In another embodiment, a method is provided for robotically moving an array of vessels to a fermentor, and then from a fermentor to a processing station. According to the method, a plurality of sample vessels are provided, each holding a fermentation sample. The plurality of sample vessels are introduced to a fermentation apparatus, preferably with the assistance of a robot. The fermentation samples are fermented and then transported once fermented with the assistance of a robot to a processing station where the samples are processed. In one particular application, processing station centrifuges the samples, most preferably in the same vessel as where the samples were fermented.

In another embodiment, a method is provided for robotically moving a same array of sample vessels from a fermentor to a centrifuge where samples are centrifuged in the same sample vessels. According to the embodiment, the method comprises fermenting a plurality of fermentation samples in a plurality of sample vessels; transporting the sample vessels containing the fermented fermentation samples to a centrifuge head with the assistance of a robot; and centrifuging the fermented fermentation samples in the same sample vessels in which the fermentation was performed. The method optionally further includes isolating the supernatant from the sample vessels after the fermentation samples have been centrifuged.

According to any of the above embodiments, the plurality of sample vessels preferably include at least 4 sample vessels, preferably at least 10 sample vessels, at least 20 sample vessels, and more preferably at least 40 sample vessels. Each sample vessel preferably contains at least 25 mL of fermentation sample, more preferably at least 50 mL of fermentation sample. Each sample vessel also preferably contains between 25 mL and 500 mL of fermentation sample, between 25 mL and 250 mL of fermentation sample, between 25 mL and 150 mL of fermentation sample, between 25 mL and 100 mL of fermentation sample, between 50 mL and 500 mL of fermentation sample, between 50 mL and 250 mL of fermentation sample, between 50 mL and 150 mL of fermentation sample, or between 50 mL and 100 mL of fermentation sample. Also according to any of the above embodiments, introducing the plurality of sample vessels to the fermentation apparatus may include moving at least 4 sample vessels at a time to the fermentation apparatus, more preferably moving at least 10 sample vessels at a time, and most preferably moving at least 20 sample vessels at a time. Also according to this embodiment, transporting the samples once fermented to a processing station may include transporting at least 4 sample vessels at a time from the fermentation apparatus to the processing station, more preferably moving at least 10 sample vessels at a time, and most preferably moving at least 20 sample vessels at a time.

Also according to any of the above embodiments, the plurality of sample vessels may have a layout which is maintained by the sample carrier, fermenting the fermentation samples including operably attaching the fermentor head relative to the sample vessels, the fermentor head having a layout which matches the layout of the sample vessels. Further according to any of the above embodiments, the fermentor head may have a plurality of probes which are inserted into the sample vessels when the fermentor head is operably attached to the sample vessels. Further according to any of the above embodiments, the plurality of probes may deliver oxygen to the sample vessels during the fermentation. The plurality of probes may also agitate the samples within the sample vessels during fermentation. When the fermentation is anaerobic, the plurality of probes may deliver inert gas to maintain anaerobic fermentation conditions in the vessels.

Also according to any of the above embodiments, the plurality of sample vessels may have a layout which is maintained by the sample carrier, fermenting the fermentation samples including operably attaching the fermentor head relative to the sample vessels, the fermentor head having a layout which matches the layout of the sample vessels. Further according to any of the above embodiments, the fermentor head may have a plurality of probes which are inserted into the sample vessels when the fermentor head is operably attached to the sample vessels. Further according to any of the above embodiments, the plurality of probes may deliver oxygen to the sample vessels during the fermentation. The plurality of probes may also agitate the samples within the sample vessels during fermentation. When the fermentation is anaerobic, the plurality of probes may deliver inert gas to maintain anaerobic fermentation conditions in the vessels.

Also according to any of the above embodiments, the plurality of sample vessels may be transported robotically to the processing station by robotic movement of the sample carrier. Alternatively the sample vessels may be transported manually.

Also according to any of the above embodiments, providing the plurality of sample vessels may include transporting to a fermentation station where the fermentation is performed with the assistance of a robot which moves the sample carrier to the fermentation station. Transporting the fermented samples may include moving the sample carrier with the assistance of a robot. According to this variation, the plurality of sample vessels may be transported robotically to the fermentation station and to the processing station without having to remove the sample vessels from the carrier.

The processing station to which the sample vessels are transported may include a centrifuge. The same sample vessels are preferably used to centrifuge the sample as are used to ferment the samples. Accordingly, the sample vessels are preferably compatible with being centrifuged.

If a sample carrier is used to transport the sample vessels, the method may further comprise removing the sample vessels from the sample carrier and introducing the same sample vessels into a centrifuge head compatible with the centrifuge. According to this variation, the sample vessels are preferably removed from the sample carrier and introduced into the centrifuge head with the assistance of a robot. Optionally, the sample carrier may be a centrifuge head compatible with the centrifuge.

The processing station may include an aspirator, the method further including aspirating the fermentation samples from the sample vessels. The sample carrier may be used to provide a layout to the plurality of sample vessels. The processing station may include an aspirator having an aspirator head having a layout which matches the layout of the sample vessels, the method further including operably attaching the aspirator head to the sample vessels and aspirating the fermentation samples within the sample vessels.

The processing station may include a dispenser, the method further including dispensing material into the fermentation samples. The sample carrier may be used to provide a layout to the plurality of sample vessels. The processing station may include a dispenser having a dispensing head having a layout which matches the layout of the sample vessels, the method further including operably attaching the dispenser head to the sample vessels and dispensing the fermentation samples within the sample vessels.

The layout which is maintained by the sample carrier may be a grid with at least 2 rows and at least 2 columns, optionally a grid with at least 4 rows and at least 2 columns, optionally a grid with at least 4 rows and at least 4 columns, and optionally a grid with at least 6 rows and at least 4 columns.

A robot is also provided for processing a plurality of fermentation samples, comprising: a robot having an arm and a griping element adjacent a distal end of the arm which is adapted to grip a plurality of sample vessels at the same time, the arm being capable of moving the griping element from adjacent a fermentor to adjacent a centrifuge head; and computer executable logic for controlling a motion of the robot arm and gripping element between the fermentor and the centrifuge head such that the robot moves a plurality of sample vessels from a fermentor into a centrifuge head at the same time. The robot is preferably capable of transporting at least 4 sample vessels at a time, more preferably moving at least 10 sample vessels at a time, more preferably moving at least 20 sample vessels at a time, and most preferably moving at least 40 sample vessels at a time.

The present invention also relates to the use of the various methods and devices of the present invention in combination with performing submicroliter crystrallizations experiments to determine crystallization conditions for a protein. More specifically, the present invention relates to fermenting cells which express a protein in 2, 3, 4, 5, 10, 20, 40 or more separate fermentations; and purifyng the expressed protein from the fermentations. The method may further comprise performing crystallization experiments using the purified protein to determine crystallization conditions for the protein.

Each of the separate fermentation vessels are sized to have relatively small volumes, e.g., 500 mL, 250 mL, 150 mL, 100 mL or less fermentation volumes, for example, between 25 mL and 500 mL, between 25 mL and 250 mL, between 25 mL and 150 mL, or between 25 mL and 100 mL. Because of the relatively small fermentation volumes, the fermentations can be performed using the fermentation system of the present invention. For example, the different fermentations vessels can be held in a same carrier. The fermentations can also be performed using a common gas distribution arrangement as described herein.

Also because of the relatively small fermentation volumes, purifyi• ng a protein from the fermentations can optionally be performed where at least part of the purification process is performed in the same fermentation vessels. For example, the fermentation volumes can be transferred to a centrifuge head by simply transferring the same fermentation vessels to the centrifuge head. The fermentations can then be centrifuged in parallel as part of the protein isolation process. Further processing steps such as cell lysis and cell pellet and supernatant isolations can also be performed in the same fermentation vessels. Using the devices and processes described herein, certain operations such as cell lysis, cell pellet isolation and supernatant isolation can also be performed in parallel.

The amount of protein that is purified from the different small volume fermentations can be used to perform submicroliter protein crystallization experiments in order to determine crystallization conditions for the expressed protein. By performing protein crystallization experiments where a protein solution volume of less than 1 microliter (e.g., 1000, 750, 500, 250, 100, 50 or less nanoliters) is used per crystallization experiment, such as by the process described in U.S. Pat. No. 6,296,673 entitled "Methods and Apparatus for Performing Array Microcrystallizations", the amount of protein that is needed to perform crystallization experiments to determine crystallization conditions is significantly reduced. For example, the amount of a given protein that is needed to perform crystallization experiments to determine crystallization conditions may be 5 mg, 4 mg, 3 mg, 2 mg, 1 mg, 0.5 mg or less. As a result, the amount of protein that needs to be expressed in a fermentation and then purified is significantly reduced.

It is reasonable to estimate a 10% yield going from expressed protein in a fermentation to purified protein for use in crystallization experiments. Accordingly, by being able to determine crystallization conditions using less than 5 mg of purified protein, it is possible to obtain this protein from a fermentation that comprises 50 mg of the protein. This amount of protein can be fermented and then processed using the methods and devices of the present invention.

It should thus be appreciated that the methods and devices of the present invention, in combination with performing submicroliter crystallization trials, make it possible to take cells expressing a protein to be crystallized, and in a substantially parallel manner, go from fermenting the cells to isolating, purifying and crystallizing the expressed protein. Thus, the reduced amount of purified protein needed to determine crystallization conditions made possible by submicroliter crystallization, in combination with the highly parallel and semiautomated process of going from fermentation to purified protein according to the present invention, a parallel, high throughput process of going from protein expression to protein crystal and to crystal structure is made feasible.

The methods and devices of the present invention will now be described in greater detail.

II. Fermentation Apparatus and Methods

A. Sample Arrangement for Fermentation

The present invention provides a multi-sample fermentation apparatus. Typically, the apparatuses of the invention comprise a sample holder or container frame and a gas distribution system. For example, in one embodiment, a container frame is used to hold and/or transport an array of sample vessels for fermentation. A fermentor head, e.g., comprising an array of cannulas corresponding to the array of sample vessels, is typically coupled, e.g., directly, to the container frame and/or sample vessels. Gas, e.g., oxygen and/or nitrogen, is distributed into the multiple sample vessels via the cannulas and fermentor head providing multi-sample fermentation. The fermentors are described in more detail below followed by methods of using them, e.g., to provide multiple processing steps in the same sample vessel.

A "container frame" as used herein refers to an arrangement that holds and/or maintains a plurality of sample vessels in a desired arrangement. Typically, the container frames of the invention are transportable and autoclavable. In addition, they typically have no movable parts. A transportable container frame is one that is easily transported or moved while holding the sample vessels in the desired arrangement. For example, a container frame of the invention optionally has handles for transportation to a processing station, e.g., after fermentation is complete. An autoclavable container frame is one that can be placed directly in an autoclave for sterilization, e.g., including the sample vessels and samples if desired.

By using a transportable container frame, the entire array of sample vessels is optionally transported to and from one fermentation processing station to another processing station in a multiple process production. For example, a transportable container frame is optionally used to transport an array of sample vessels into a temperature controlled area such as a water bath, e.g., a water bath controlled by a temperature controller and temperature coil immersed in the water bath. Other forms of temperature control are also optionally used, such as temperature controlled gel baths, ovens, glove boxes, or air chambers.

Typically, the container frame maintains the sample vessels in an array, e.g., a rectangular array. In an embodiment shown in FIG. 1, individual sample vessels 15 are configured in a rectangular array, but the array is optionally configured in any physical construct that is conducive to fermentation or that is compatible with other processing steps. For example, a honeycomb, circular, triangular, or linear configuration may be more efficient in other contemplated applications of the present invention.

The container frames of the present invention typically have a plurality of placement wells for positioning the plurality of sample vessels, e.g., in an array. For example, the placement wells optionally comprise indentations in the bottom of a container frame, into which sample tubes are optionally placed. In addition to the indentations or wells in the bottom of the container frame, the container frames optionally include an upper portion, e.g., for supporting the tops of the sample tubes and maintaining their position. An example container frame is shown in FIG. 1 (container frame 250).

For example, the bottom of each individual sample vessel is typically positioned within a placement well, e.g., placement well 257 in FIG. 1. The array of placement wells preferably mirrors the configuration of the sample vessel array and is embedded in the transportable container frame. Placement wells may, however, be arranged in alternative configurations. For example, placement wells may be arranged as linear troughs, each holding a row of sample vessels. In another embodiment, placement wells are absent from the transportable container frame. For example, the container frame optionally has a solid bottom surface with no indentations or wells. The sample vessels are then positioned in the frame, e.g., tightly packed against the sides of the frame to maintain the array configuration.

B. Sample Vessels

Sample vessels of the present invention typically comprise test tubes, other sample tubes, jars, flasks or any other container for holding a sample. Typically, the sample vessels have a volume of about 50 to about 200 milliliters, more typically about 80 to about 100 ml. The sample vessels are typically placed in an array of placement wells in a container frame, e.g., for autoclaving, processing, fermentation, and the like.

In some embodiments, the sample vessels are constructed of Pyrex glass or polycarbonate, but other suitable materials are optionally used to construct the sample vessels. For example, plastic, ceramic, metal, e.g., aluminum, or any other material is optionally used that is non-reactive to fermentation medium or to other materials involved in additional processes contemplated in a multiple process production, such as in a high throughput system. It will further be appreciated that the fermentation medium may be the same medium in each individual sample vessels or, alternatively, the array of sample vessels optionally includes a combination of different fermentation mediums. For example, fermentation medium may be the same in each individual sample vessel and contain the same fermentation broth for a bulk synthetic process. Alternatively, each sample vessel in an array may have a slightly different fermentation broth in order to optimize the production yield of a certain component.

In some embodiments, sample vessels with gripper surfaces are optionally used. In this embodiment, the container frame typically comprises a corresponding gripper surface, e.g., for maintaining the vessels in the desired configuration or to aid in transporting the array of sample vessels to and from a fermentation station and/or processing station.

In other embodiments, sensors are optionally included in the sample vessels of the invention. For example, a pH or temperature sensor is optionally positioned proximal to or within a sample vessel to monitor the fermentation reaction.

Fermentation samples are optionally placed in the sample vessels prior to their placement in the container frame or after such placement. In one embodiment, colonization of bacteria and other preparative steps are performed within the sample vessels, e.g., while they are contained in the container frame. For example, bacteria and initial nutrients are dispensed into each sample vessel at a prior processing station. Being able to prepare bacteria directly in each individual sample vessel eliminates the need to inoculate a culture and initiate colonization in a separate container before transferring the sample to the fermentation apparatus. Using the container frame arrangement of the present invention to colonize the fermenting bacteria decreases costs by eliminating a separate colonization arrangement. Once bacteria are colonized, sample vessels are conveniently transported, e.g., within the container frame, to a fermentation station, e.g., a water bath or any other temperature controlled area, such as a heated room. At the fermentation station or any time prior, a gas distribution arrangement is attached to the container frame to bubble gas into each sample vessel for fermentation. The gas distribution arrangements are described in more detail in the example below.

C. Example Fermentors and Systems

A gas distribution arrangement is used to provide gas flow to the sample vessels in the fermentor during fermentation. The gas distribution system typically comprises a gas inlet which is configured to flow gas from a gas source into a plurality of sample vessels in a container frame. Typically, the gas distribution arrangement is attached to the container frame, e.g., placed on top or screwed down. For example, the gas distribution arrangement typically comprises or is coupled to a plurality of cannulas through which the gas is flowed. The cannulas extend into each sample vessel for delivery of gas, e.g., to the bottom of the sample vessel. Such cannulas also optionally provide agitation of the sample within the sample vessel.

A gas source typically comprises a source of one or more gases, for example, air and oxygen. For example, in one embodiment the gas source contains an inlet for $N_2$ gas and an inlet for $O_2$ gas. The ratio of each gas can be controlled either manually or remotely by using a process controller. The ability to adjust gas ratios enables the present invention to optimize the amount of gas, e.g., oxygen, needed as the growing conditions change throughout the fermentation. For example, a process controller is optionally used to linearly change the ratio of air/oxygen over the course of a fermentation. Alternatively, the ratio is changed stepwise as fermentation proceeds. Any type, mixture, or number of gases are optionally introduced and mixed through the gas sources of the invention and provided to fermentation samples contained in one or more sample vessels, e.g., through a set of cannulas.

A cannula is a small tube for insertion into a duct or vessel, e.g., a fermentation sample vessel or tube as provided herein. In the present application, the cannulas are positionable inside the plurality of sample vessels, e.g., they typically comprise flexible or rigid tubes that are inserted into sample vessels for the delivery of various gases into the sample vessels. In one embodiment, the cannulas are arranged into an array, which array typically corresponds to an array of sample vessels. An example array of the invention comprises an 8 by 12 member array of sample vessels each having an associated rigid cannula. Typically, a cannula extends substantially to the bottom of each individual sample vessel in order to increase aeration and mixing. For example, the cannula optionally extend about 15 to about 16 cm from the bottom surface of a gas distribution arrangement. In some embodiments, two or more cannulas are provided in each sample vessel.

Figure 8:
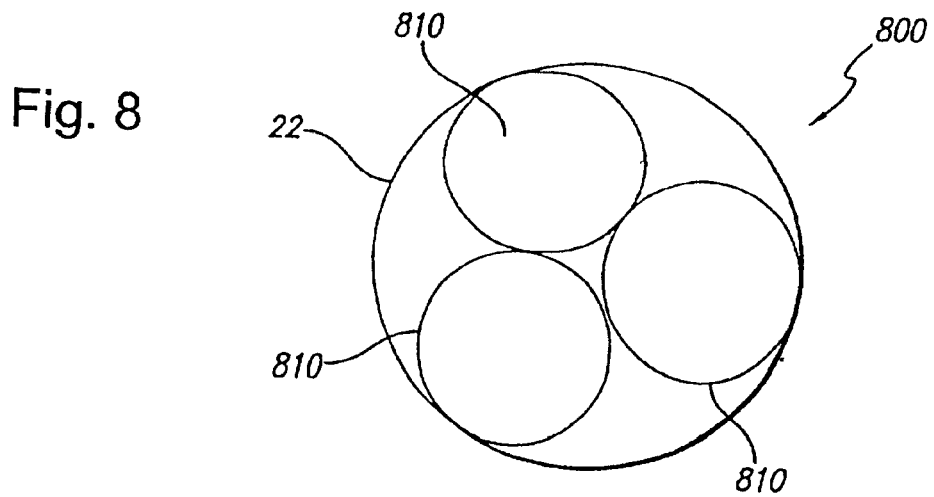
FIG. 8 is a cross sectional view of a cannula in accordance with the present invention.

In the embodiment illustrated in FIG. 8, gas flows through cannula 22 through three passages. Gas flow through passages is optionally individually or collectively regulated. Smaller gas bubbles are obtained with multiple small passages than with a single, larger passage through the cannula. As a result, gas bubbles formed from these multiple passages have more surface area than bubbles formed from a single passage. In a preferred embodiment, passages are precision drilled in order to more accurately adjust gas flow within each passage and to ensure uniform gas delivery across the set of sample vessels. Fewer or more passages may be used according to the specific application of the present invention. For example, the cannulas typically have about 1 to about 5 passages, more typically, 2 or 3 passages. Passages are optionally the same or different sizes and may be circular or any non-circular shape, such as rectangular, oval, or triangular.

In one embodiment cannula are included in a cannula assembly comprised of an array of individual cannulas corresponding to the plurality of sample vessels. Each individual cannula is optionally connected by a fastener which couples the cannula to a gas distribution arrangement.

Figure 12:
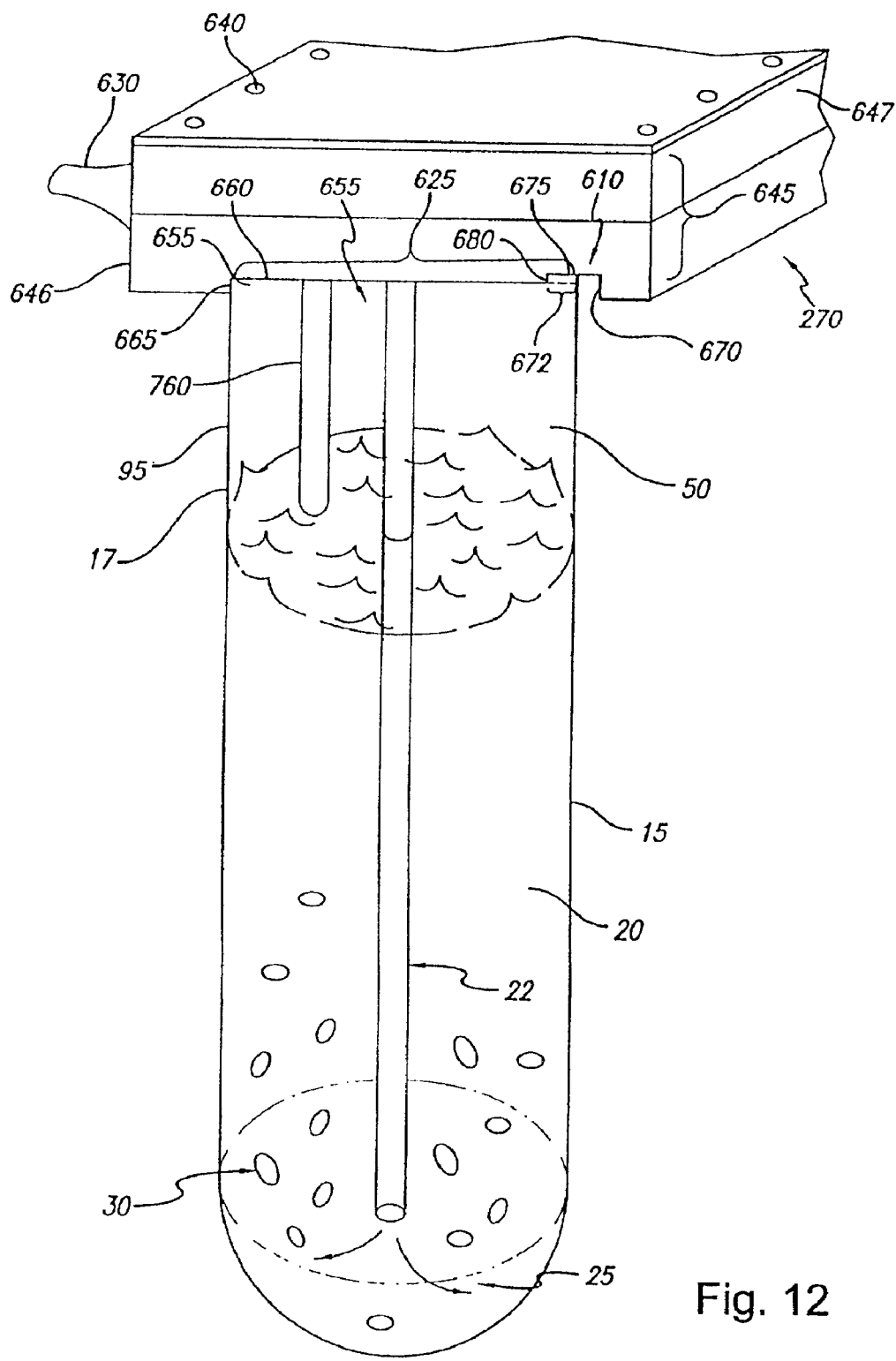
FIG. 12 is a schematic showing a perspective view of a fermentation sample vessel employing a dispensing plate in accordance with the present invention.
Figure 14:
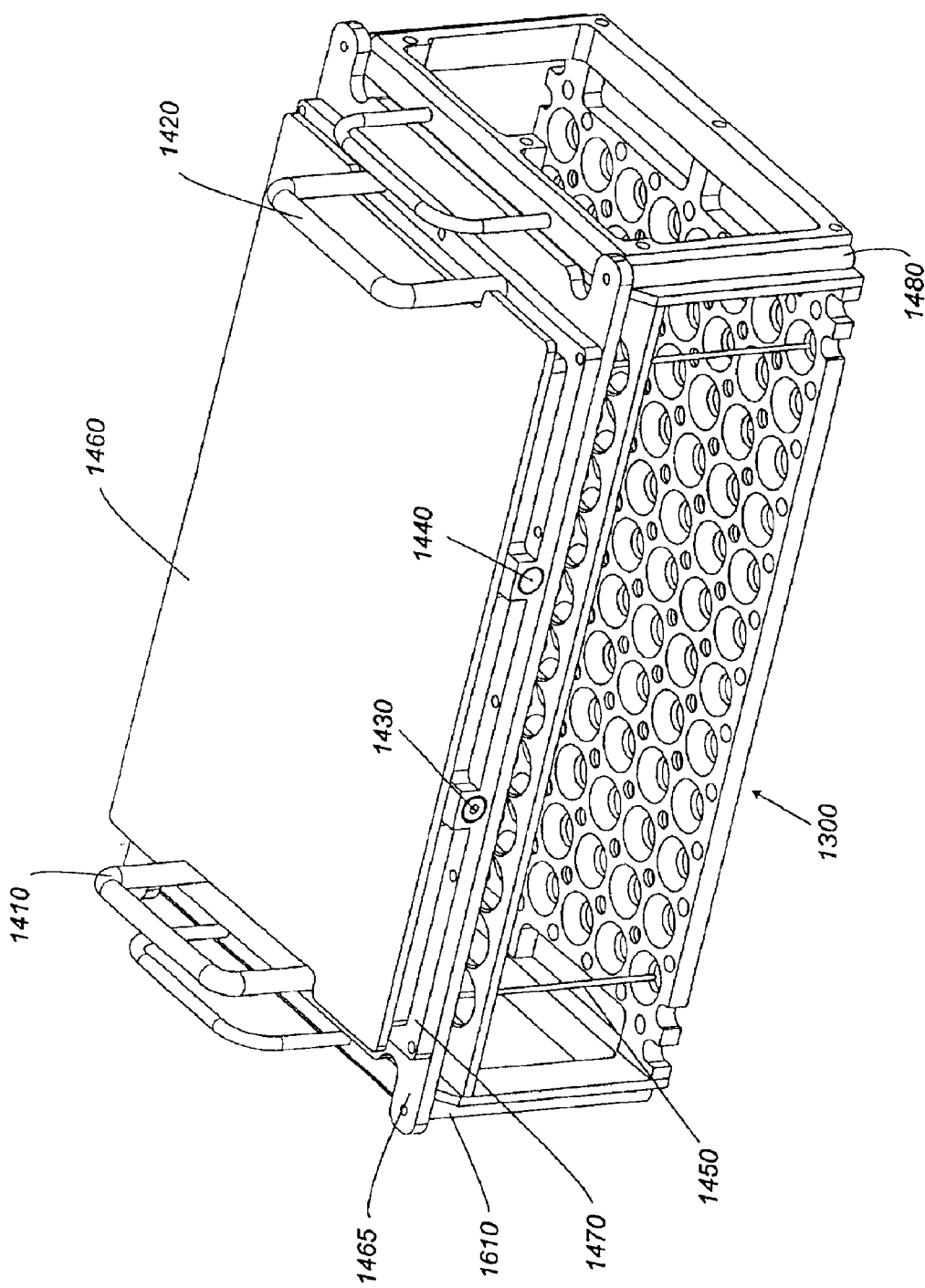
FIG. 14 is a schematic drawing that illustrates the container frame of FIG. 13 coupled to a gas distribution arrangement.

Gas, e.g., oxygen or an oxygen/air mixture, is delivered, e.g., from a manifold or other distribution system, to the sample vessels via the cannulas, thus oxygenating, if desired, the entire array of sample vessels within the container frame. For example, a gas source is optionally coupled directly to the gas distribution arrangement, e.g., with or without the use of a manifold, as illustrated in FIGS. 6, 12, and 14.

In this manner, the exact mixture of gases delivered from the gas source is uniformly distributed to each individual cannula assembly. Any gas distribution arrangement is optionally employed that uniformly delivers oxygen, an oxygen containing mixture, or another gas or gas mixture capable of fermenting the sample, from a gas source into the plurality of sample vessels. Example gas distribution arrangements are provided in FIGS. 1, 3, 12, and 14, which are described in more detail in the examples provided below.

In some embodiments, the gas distribution arrangement is comprised of one or more plates attached to an array of cannula, e.g., using a manifold, and a gas inlet, which delivers oxygen, an oxygen containing gas mixture, or another gas or gas mixture capable of fermenting the sample, to the sample vessels via the cannula.

Typically, the plates are aligned and fastened together, e.g., to form an air-tight, liquid-tight seal. A hollow space or interior space typically exists between the plates or within one of the plates through which gases are uniformly distributed to the associated cannula array. Any suitable fastener may be used. For example, guide pins, rivets, nails, nut/bolt combinations, or magnets may be used. A releasable fastener, such as a screw or nut/bolt combination, is used in a preferred embodiment, although permanent type fasteners, such as adhesives, may be desired in some applications. Vertical supports are optionally attached to the gas distribution arrangement, thus supporting the arrangement on an array of sample vessels.

The plates are optionally composed of any suitable material that maintains the structural integrity of the plate during fermentation. For example, a plate is optionally composed of metal, plastic, ceramic, or any suitable composite. In one example, the plates comprise Teflon®-coated aluminum, thus enabling the plates to undergo autoclave sterilization procedures along with the container frame and sample vessels as described above.

Figure 9:
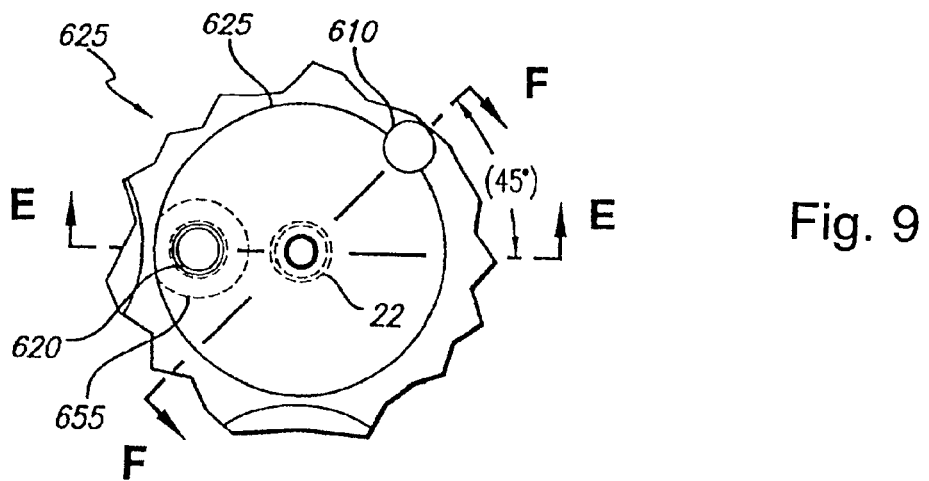
FIG. 9 is schematic showing a bottom view of a sample vessel area of a dispensing plate shown in FIG. 6 in accordance with the present invention.
Figure 10:
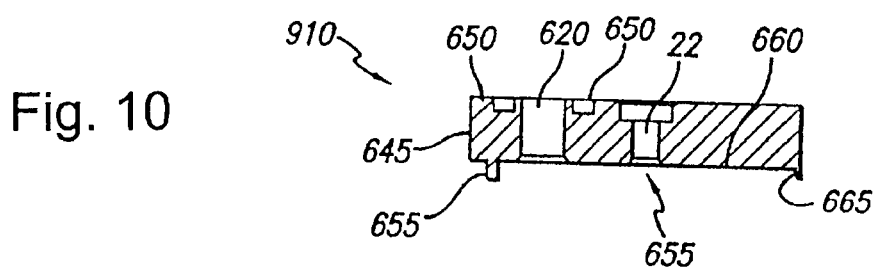
FIG. 10 is a schematic showing a cross sectional view of the sample vessel area shown in FIG. 9 taken along the line E—E in accordance with the present invention.
Figure 11:
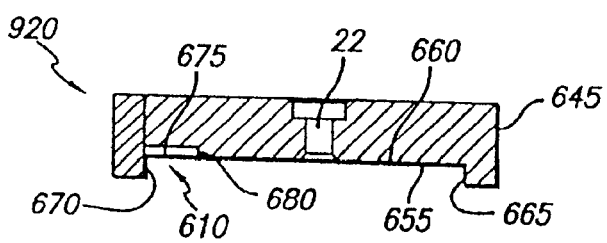
FIG. 11 is a schematic showing a cross sectional view of the sample vessel area shown in FIG. 9 taken along line F—F in accordance with the present invention.

In one embodiment, the gas distribution arrangement comprises two plates. The first plate, e.g., the bottom plate, typically comprises a plurality of sample vessel areas or indentations on the bottom surface. The indentations correspond to the array of sample vessels held in the container frame and serve to cap the sample vessels. FIGS. 9–11 illustrate features encompassed by the indentations, e.g., sample vessel area or indentation 625 on bottom portion 646. The indentations or recesses are also used, e.g., to immobilize the sample vessel within the container frame. Although the indentations are illustrated as circular, they are optionally any shape, e.g., to correspond to a variety of sample vessels.

One or more vents are typically positioned on the circumference of the sample vessel area, cap, or recess to allow gases and built up pressure to escape the sample vessel. FIG. 11 illustrates one embodiment of a venting space. However, other configurations of venting spaces and recesses are optionally constructed such that built-up pressure within sample vessels can escape without contaminating other sample vessels.

When the top surface of a sample vessel abuts the bottom surface of the gas distribution arrangement, gases, liquids, emulsions, or excess pressure built up in the sample vessel escape through a recess and/or venting space created in the gas distribution arrangement. Cross-contamination of these escaping elements is significantly reduced because a vertical edge in the bottom surface of the gas distribution arrangement separates each sample vessel from an adjacent sample vessel. Moreover, gas flow from the cannulas maintains a positive pressure within the sample vessel such that contaminants outside a particular sample vessel are not drawn in through the vent.

In some embodiments, the first plate comprises the plurality of cannulas that deliver gas to the sample vessels. The cannulas typically extend from the top surface of the plate, through the plate, and below the bottom surface of the plate. The cannulas are generally of sufficient length to reach within about 1 cm to about 0.1 cm of the bottom of the sample vessels. The cannulas open to the top surface of the plate, e.g., for gas to be distributed through the cannulas into the sample vessels. The cannulas are configured to be positionable in an array of sample vessels, e.g., held in a container frame.

In addition to the cannulas, the first plate optionally includes a plurality of apertures that correspond to the array of sample vessels. For example, the apertures optionally provide an opening through the first plate, through which fluids may be added into the sample vessels when the gas distribution arrangement is attached to a container frame.

The first plate is typically attached to a second plate, e.g., with screws or adhesives, which second plate typically comprises one or more gas inlets for providing gas flow into the cannulas of the first plate. The gas inlet opens into an interior space created between the second plate and the first plate, which interior space provides gas flow to the cannulas.

In addition, the second plate also comprises a plurality of apertures, e.g., to provide liquid access to the sample vessels. The apertures of the second plate typically align with or match the apertures on the first plate when the two plates are coupled. The apertures provide openings through which liquid can be added into the sample vessels in a container frame attached to the gas distribution arrangement. The apertures also serve as openings for an array of aspirators or dispensers that can be used to aspirate or dispense liquid into the sample vessels. In other embodiments, pipettes or syringes are used to draw samples or add nutrients, water, etc, e.g., through the apertures. The gas distribution arrangement also optionally comprises a lid for covering the apertures when a sealed environment is desired. The first plate and second plate together comprise a fermentor head or manifold for delivering gas or fluid to a plurality of sample vessels. More detailed examples are provided below.

A process controller is also optionally coupled to the fermentation apparatus of the invention, e.g., for controlling gas flow to the cannulas, for altering ratios of air to oxygen that are bubbled through the cannulas, for monitoring and controlling temperature, for directing the addition of various reagents, and the like. An automated process using a process controller is described in more detail in the examples below.

Other devices are also optionally coupled to the fermentor apparatus of the present invention. For example, dispensers, aspirators, centrifuges, and other processing devices are optionally coupled to the fermentor or configured for use with a container frame, e.g., so that samples can be processed in the same vessel in which fermentation is carried out. For example, a dispenser is optionally configured to dispense liquid into a plurality of sample vessels held in a container frame, e.g., through a plurality of apertures in a gas distribution arrangement. Aspirators are likewise optionally configured to coordinate with the container frame and gas distribution manifolds of the present invention.

As described further below, a centrifuge is also optionally used in processing fermentation samples. For example, a centrifuge is optionally configured to accept the sample vessels as centrifuge tubes to avoid transferring of samples prior to centrifugation. For more information on centrifugation systems for use in the present invention, see, e.g., U.S. Ser. No. 09/780,589, entitled "Automated Centrifuge and Method of Using Same," by Downs et al, filed Feb. 8, 2001.

1. Example Fermentor #1

In accordance with the present invention, an example fermentation apparatus is provided in FIG. 1. Fermentation apparatus 10 generally comprises sample holder arrangement 255, cannula assembly 80 and gas distribution arrangement 270. The illustrated fermentation apparatus 10 is configured to separately and simultaneously ferment multiple batch samples in sample vessels that are compatible with direct pre- and post-fermentation processing as described above.

Sample holder arrangement 255 is comprised of gripping surfaces 17, individual sample vessels 15, which typically form an array of sample vessels, such as array 110, a transportable container frame 250, and an array of placement wells 260 corresponding to array 110. Gripping surfaces 17 are optionally located on each individual sample vessel 15, which collectively form sample vessel array 110. It is preferable that gripping surface 17 resides on the bottom of each sample vessel, but gripping surface 17 is optionally located on any surface of the sample vessel that enables sample vessel 15 to be transferred to or from container frame 250 or another processing station.

The bottom of each individual sample well 15 is positioned within a placement well, e.g., placement well 257. The array of placement wells 260 preferably mirrors the configuration of array 110 and is embedded in transportable container frame 250.

By using transportable container frame 250, the entire array of sample vessels 110 is optionally transported to and from one fermentation processing station to another processing station in a multiple process production. In this illustrated example, transportable container frame 250 transports array of sample vessels 110 into a temperature controlled area 210 such as a water bath. In this embodiment, temperature controlled area 210 is comprised of water bath 240 in water bath container 215, which is controlled by water bath temperature controller 220 and temperature coil 230 immersed in water bath 240.

Figure 3:
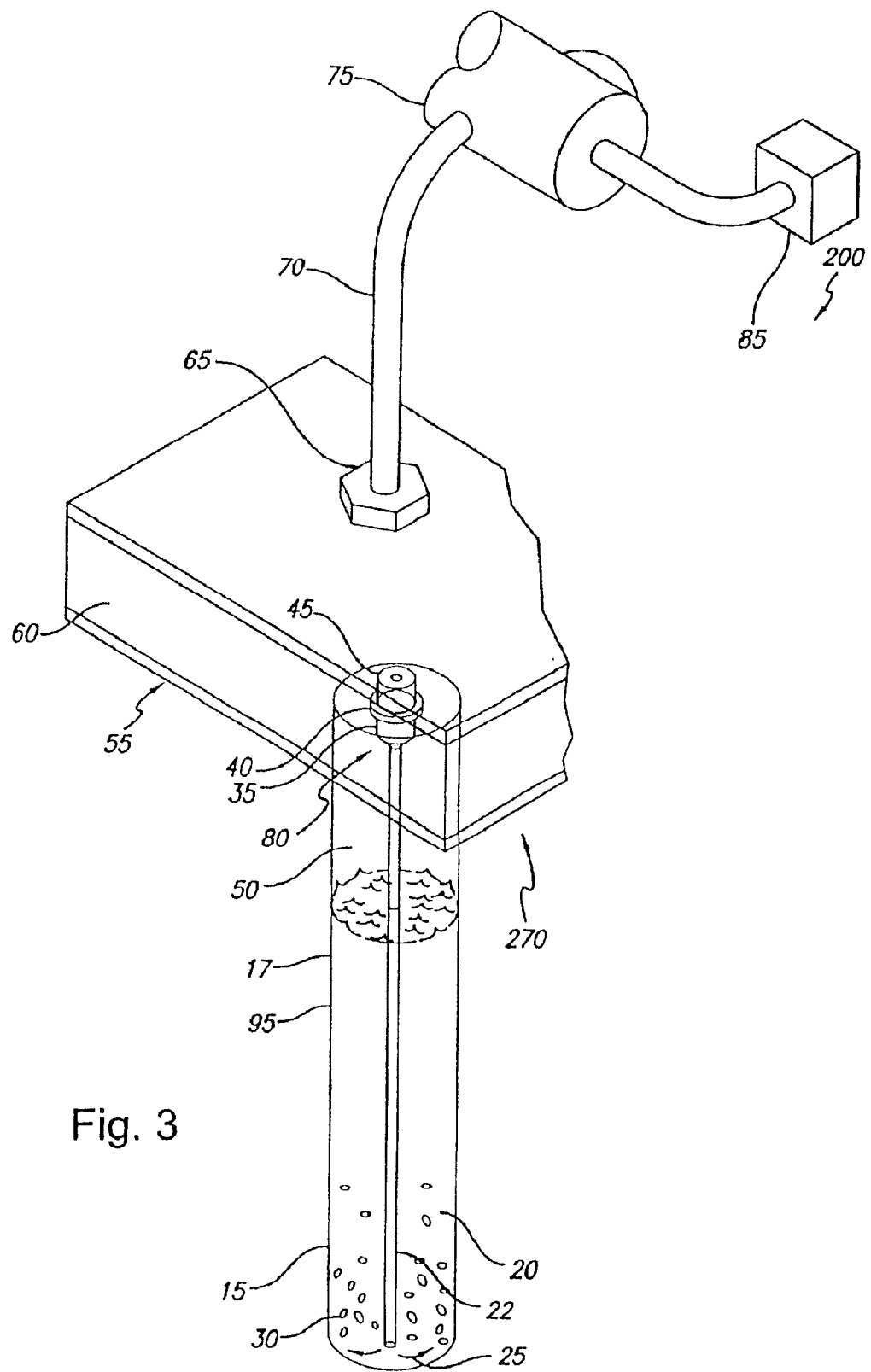
FIG. 3 is a schematic illustrating a perspective view of an individual fermentation sample vessel in accordance with the present invention.

In FIGS. 1 and 3, an example gas distribution arrangement is shown. Gas distribution arrangement 270 is comprised of gas source 85 connected to manifold 75. Conduit 70 connects manifold 75 to connector 65. Connector 65 connects manifold 75 to gas distributor 55.

In the embodiment illustrated in FIGS. 1 and 3, cannula assembly 80 is comprised of cannula array 120, which is composed of individual cannulas 22 that correspond to sample vessel array 110. Each individual cannula 22 is optionally connected by a fastener 35, which couples cannula 22 to a gas distribution arrangement 270. Cannula 22 preferably extends substantially to the bottom of each individual sample vessel 15 in order to increase aeration and mixing.

In another embodiment, each individual cannula is attached directly to gas distribution arrangement 270 in an airtight, liquid-tight manner. Eliminating the need for a fastener, this embodiment directly integrates cannula 22 into gas distribution arrangement 270, thereby decreasing the number of surfaces, grooves, and/or pockets available for possible bacterial contamination, and thus decreasing the opportunities for fermentation spoilage. Likewise, cannula 22, when integrated into a gas distribution arrangement 270 are optionally autoclaved with gas distribution arrangement 270, thereby eliminating the need to unfasten each cannula 22 separately before cleaning and sterilization. This convenience saves both time and money as well as adding to the uniformity of each batch. For example, the possibility for human error is minimized, because each cannula 22 does not have to be fastened individually before each fermentation run or unfastened individually prior to cleaning and sterilization. Also any non-uniformities in any one cannula 22 will be immediately apparent as an individual cannula 22 will be constantly associated with the same sample vessel in each run. Integrated cannula are shown in FIG. 14.

Referring to FIG. 5, gas, e.g., oxygen, is delivered from manifold 75 to all parts of distributor 55 through a hollow space 60 of distributor 55, thus oxygenating, if desired, the entire array of sample vessels 110. Oxygen and/or one or more other gases is delivered from distributor 55 through individual cannula 22, which is connected to distributor 55 by way of cannula assembly 80.

In one embodiment, cannula assembly 80 is comprised of a connector 45 on an inside face of distributor 55 as well as connector 40 on an outside face of distributor 55. Fastener 35 attaches individual cannula 22 to connector 40 on distributor 55. Arrows 25 depict oxygen and/or one or more other gases flowing from cannula 22 into fermentation medium 20 and producing gas bubbles 30. For example, gas source 85 is optionally coupled directly to dispensing plate 645 without the use of manifold 75, as illustrated in FIG. 6. Likewise, cannula assembly 80 may be constructed by alternative methods. For example, as shown in FIG. 6, cannula 22 is attached directly to dispensing plate 645.

In this manner, the exact mixture of gases delivered from gas source 85 is uniformly distributed to each individual cannula assembly 80. Any gas distribution arrangement is optionally employed that uniformly delivers oxygen, an oxygen containing mixture, or another gas or gas mixture capable of fermenting the sample, from gas source 85 into sample vessel 15.

FIG. 6 illustrates another embodiment of a gas distribution arrangement. Gas distribution arrangement 270 is comprised of a dispensing plate 645 directly attached to an array of cannula 120, that is configured without a manifold, manifold conduit, or manifold connector. In this embodiment, dispensing plate 645 is comprised of a bottom portion 646 and a top portion 647. Inlet 630 delivers oxygen, an oxygen containing gas mixture, or another gas or gas mixture capable of fermenting the sample, to dispensing plate 645 from gas sources 85 (not shown).

Bottom portion 646 and top portion 647 are aligned and fastened together through apertures 640, e.g., to form an air-tight, liquid-tight seal. A hollow space exists between portions 646 and 645 through which gases are uniformly distributed to cannula array 120. Apertures are used to fasten vertical supports to dispensing plate 645 that allow dispensing plate 645 to rest adjacent to array of sample vessels 110. Any suitable fastener may be used. In the illustrated example, screws connect upper portion 647 and bottom portion 646 to form dispensing plate 645. Screws also fasten aluminum legs to dispensing plate 645 as vertical supports.

Figure 2:
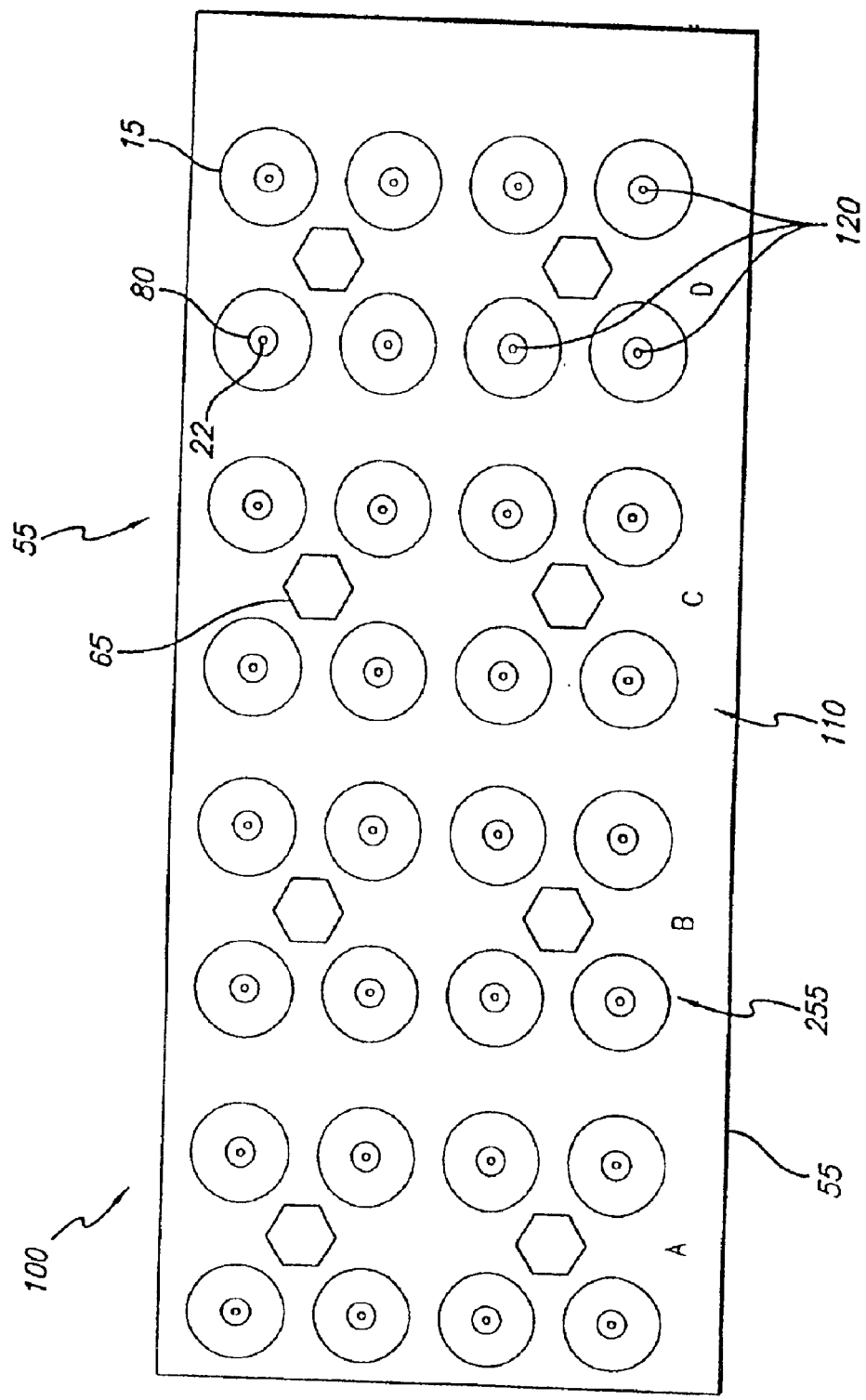
FIG. 2 is a schematic showing a top view of a fermentation apparatus in accordance with the present invention.
Figure 4:
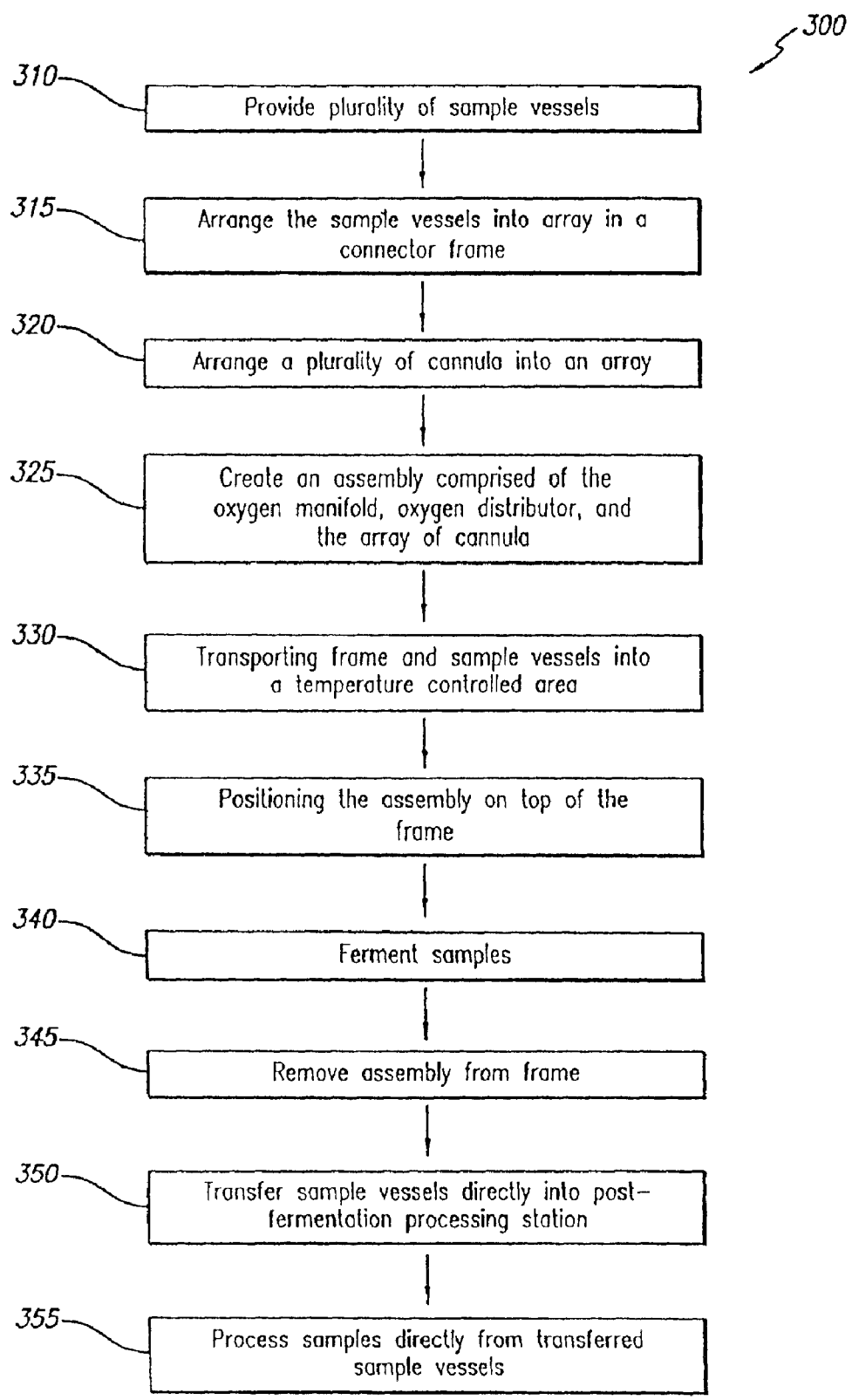
FIG. 4 is a block diagram of a fermentation method in accordance with the present invention.

FIGS. 2–4 illustrate yet another embodiment of a gas distribution arrangement. In this embodiment, cannula 22 is directly attached to bottom portion 646. Aperture 620 holds a dispensing tube 760 (not shown) for dispensing nutrients and other solutions into sample vessel 15. Aperture 620 is optionally used to access samples during the fermentation process, using, e.g., pipettes or syringes to draw samples or add nutrients, water, and/or the like into the sample vessels. Fastening groove 650 enables dispensing tube 760 to be fastened to dispensing plate 645. Indentation 655 and vertical edge 665 create a circular recess that helps immobilize sample vessel 15 within sample vessel area 625. Although in this embodiment, indentation 655 is circular and corresponds to the shape of sample vessel 15, other suitable shapes may be used.

Vent 610 is positioned on the circumference of sample vessel area 625 and allows gases and built up pressure to escape sample vessel 15. Referring to FIG. 4, vent 610 creates venting space 675. Because vertical edge 670 is larger than vertical edge 665, venting space 675 occupies a deeper recess than recess 655. The difference in height between vertical edges 670 and 665 is equal to the height of vertical edge 680 and determines the depth of venting space 675. Other configurations of venting space 675 and recess 655 (and, accordingly, vertical edges 665, 670, and 680) may be constructed such that built-up pressure within sample vessel 15 can escape through venting space 675 without contaminating other sample vessels.

When the top surface of sample vessel 15 abuts surface 660, gases, liquids, emulsions, or excess pressure built up in sample vessel 15 may escape through recess 655 and venting space 675. Cross-contamination of these escaping elements is significantly reduced because vertical edge 670 separates sample vessel 15 from an adjacent sample vessel 15. Moreover, gas flow from cannula 22 maintains a positive pressure within sample vessel 15 such that contaminants outside sample vessel 15 are not drawn in through venting space 675 into sample vessel 15 by way of recess 625, 655, or 675. Other vents 610 may be configured such that excess gases, liquids, emulsions, or excess pressure may escape through vent 610 without cross-contaminating other sample vessels 15.

In another embodiment of gas distribution arrangement array 110 is configured such that a gas distribution arrangement oxygenates, for example, each individual sample vessel 15 as opposed to utilizing a dispensing plate 645. Thus, array of sample vessels 110 is optionally oxygenated (or provided with other appropriate gas) collectively or individually by adjusting cannula assembly 80 for any individual sample vessel 15. For example, in one application, one section of the array may be oxygenated (or provided with other appropriate gas) twice as long as another section.

Referring to FIGS. 5 and 6, gripping surface 17 allows for automated or manual transfer of sample vessel 15 to and from the fermentation apparatus or another processing station, e.g., upon conclusion of fermentation. In one embodiment, gripping surface 17 is magnetic such that a magnet attracts gripping surface 17 and transfers the sample vessel to another processing station. In another embodiment, a gripping mechanism grips the outer sides of the sample vessel to effect transfer. In yet another embodiment, gripping surface 17 is a lip at the top of the sample vessel. Other surfaces that may be gripped in order to transport the sample vessel to or from the fermentation processing station are within the scope of the present invention. For example, gripping surface 17 is optionally on the inside, outside, top or bottom of sample vessel 15. In other embodiments, the samples are held in place and transported with the aid of a gripper structure.

FIG. 6 illustrates one embodiment of a gas distribution arrangement. Gas distribution arrangement 270 and cannula 22 are used together to provide gas to a sample vessel. In this example, oxygen, a mixture of oxygen and other gases, or another gas or gas mixture is introduced into dispensing plate 645 through inlet 630. Fasteners such as screws connect and align upper portion 647 to bottom portion 646 through apertures 640. Dispensing tube 760 and cannula 22 are directly attached to dispensing plate 645 and can be replaced by unfastening portions 646 and 647, replacing either or both dispensing tube 760 or cannula 22, and refastening portions 646 and 647. It is preferable for dispensing tube 760, cannula 22, inlet 630, and portions 646 and 647 to remain fastened together such that these elements are autoclaved as one unit. This allows for significant sterilization without the time and cost expense of dismantling arrangement 270 after each fermentation in order to separately sterilize each element.

In the illustrated example, a top surface of individual sample vessel 15 abuts directly onto surface 660 within sample vessel area 625. The top surface of sample vessel 15 is positioned within recess 655. Surface 660 preferably is not in contact with the entire circumference of the top surface of sample vessel 15. Also preferably, vent 610 is positioned adjacent to surface 660 such that a gap 672 exists between surface 660 and the vertical edge of sample vessel 15, thereby creating a passage for excess gases, emulsions, or pressure to escape from sample vessel 15 through venting space 675. Gas flow through cannula 22 provides sufficient pressure such that contaminants are not drawn into sample vessel 15 through venting space 675.

2. Example Fermentor #2

FIGS. 13–21 illustrate another embodiment of the fermentor apparatus of the present invention. Generally, the apparatus comprises a container frame comprising placement wells, and a gas distribution arrangement comprising a cannula array. Each piece is described in more detail below and by reference to the figures.

Figure 13:
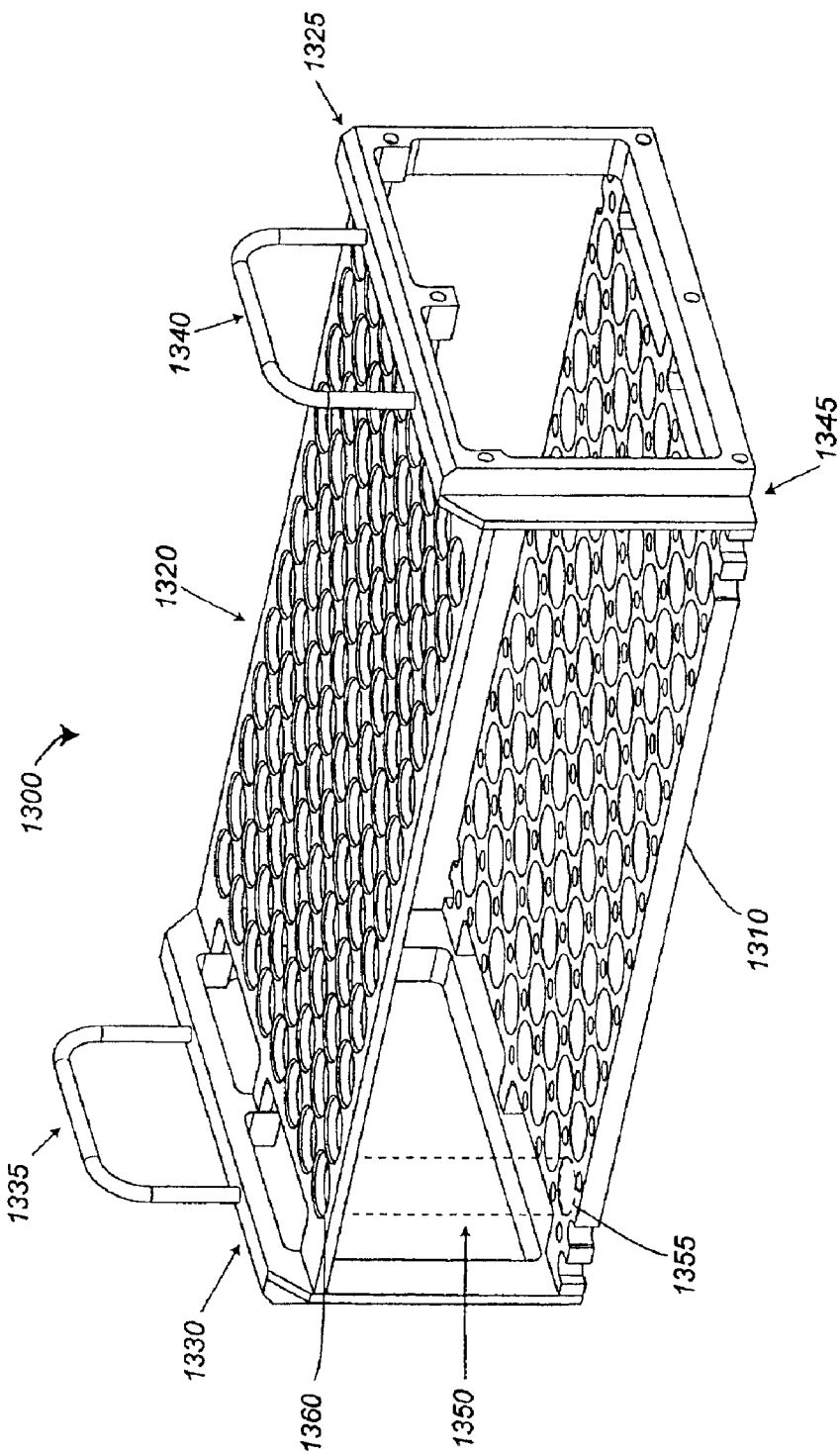
FIG. 13 is a schematic drawing that illustrates a container frame for maintaining a plurality of sample vessels in an array configuration.

Container frame 1300, as shown in FIG. 13, comprises bottom 1310 and top portion 1320 connected by side portions 1325 and 1330. The container is easily transportable, e.g., by grasping handles 1335 and 1340 which are attached to sides 1325 and 1330. Each side 1325 and 1330 has two grooves 1345 which can each receive a pin for securing a gas distribution arrangement, such as that shown in FIG. 16, e.g., using pins 1480. Top portion 1320 and bottom portion 1310 together form an array of placement wells 1350. Bottom portion 1310 of the container frame has a plurality of indentations that serve as bottoms for the placement wells, in which sample vessels are placed. For example, container frame 1300 comprises an 8 by 12 array of placement wells. Top portion 1320 comprises a matching array of holes 1360 which holes receive the sample vessels into the container frame and hold them in position within the container frame. Together holes 1360 and indentations 1355 in container frame 1300 form a rack for holding a plurality of sample vessels, e.g., tubes. Although holes 1360 are shown as circles, the shape is optionally configured to receive any desired sample vessel.

FIG. 14 illustrates a gas distribution arrangement coupled to container frame 1300. The gas distribution arrangement comprises four pins 1480 which slide into grooves 1345 to hold the gas distribution arrangement in place over the container frame. As shown in FIG. 14, the gas distribution arrangement comprises first plate 1465 and second plate 1470, which are typically fastened together, e.g., using screws or pins. An optional lid, e.g., lid 1460, is also shown. In addition, the gas distribution arrangement comprises handles 1410 and 1420 attached to second plate 1470 for easy positioning and removal of the gas distribution arrangement.

Inlets 1430 and 1440 provide gas inlets to the gas distribution arrangement, which gas inlets typically receive gas from a gas source and deliver it, e.g., to a plurality of cannulas. Typically, the plurality of cannulas is attached to the gas distribution arrangement, e.g., as part of the first plate. For example, in the illustrated embodiment, cannula 1450 is part of first plate 1465 and extends from the top of the first plate, through the first plate and below, such that the cannula is positionable inside a placement well, e.g., well 1350, or inside a sample vessel positioned within placement well 1350.

Typically, first plate 1465 comprises the cannula array and a plurality of apertures. The apertures of the first plate align with a set of apertures on the second plate to provide access to the sample vessels within the placement wells. The cannula array is optionally molded as part of the first plate or separately formed and then attached to the first plate. For example, an additional set of apertures is optionally present in the first plate to accept the array of cannula, e.g., which are received into the aperture and secured using o-rings.

Figure 18:
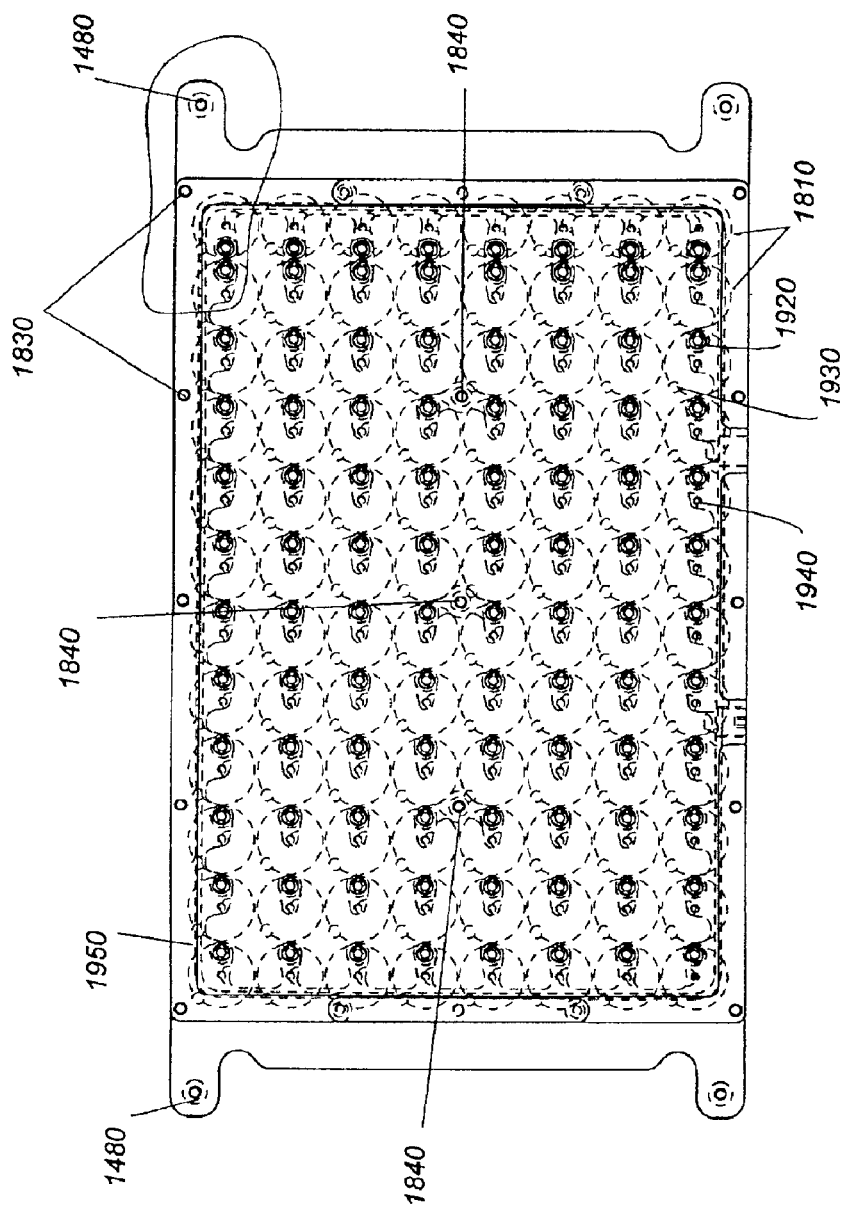
FIG. 18 is a schematic drawing that illustrates a bottom view of gas distribution arrangement as shown in FIG. 14.
Figure 19:
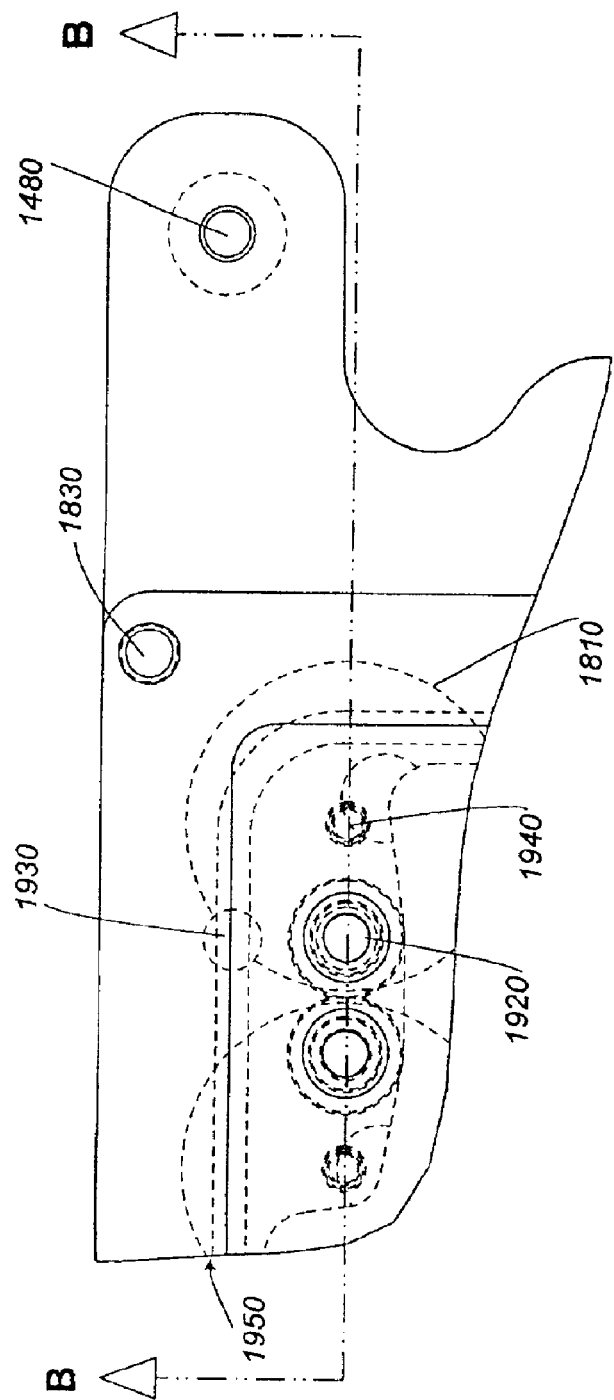
FIG. 19 is a detail illustration from FIG. 18.

FIG. 18 illustrates the bottom surface of first plate 1465. For example, on the bottom surface of the first plate, an array of sample vessel areas 1810 or indentations are used to cap the sample vessels and provide venting space as described above in Example 1. Each sample vessel area comprises an aperture to provide access to the sample vessel positioned with the associated placement well, a cannula associated with each placement well for delivering gas into each sample vessel positioned within the well, and a vent for relieving pressure build up during fermentation. In addition, FIG. 18 illustrates apertures 1830 and 1840, which are used, e.g., to attach the second plate to the first plate, e.g., via a set of screws. FIG. 19 provides a detail drawing of a portion of FIG. 18 illustrating aperture 1920, vent 1930, and cannula 1940. In addition, FIG. 19 illustrates gasket or o-ring 1950 that serves to provide a seal between the first and second plates.

Figure 21:
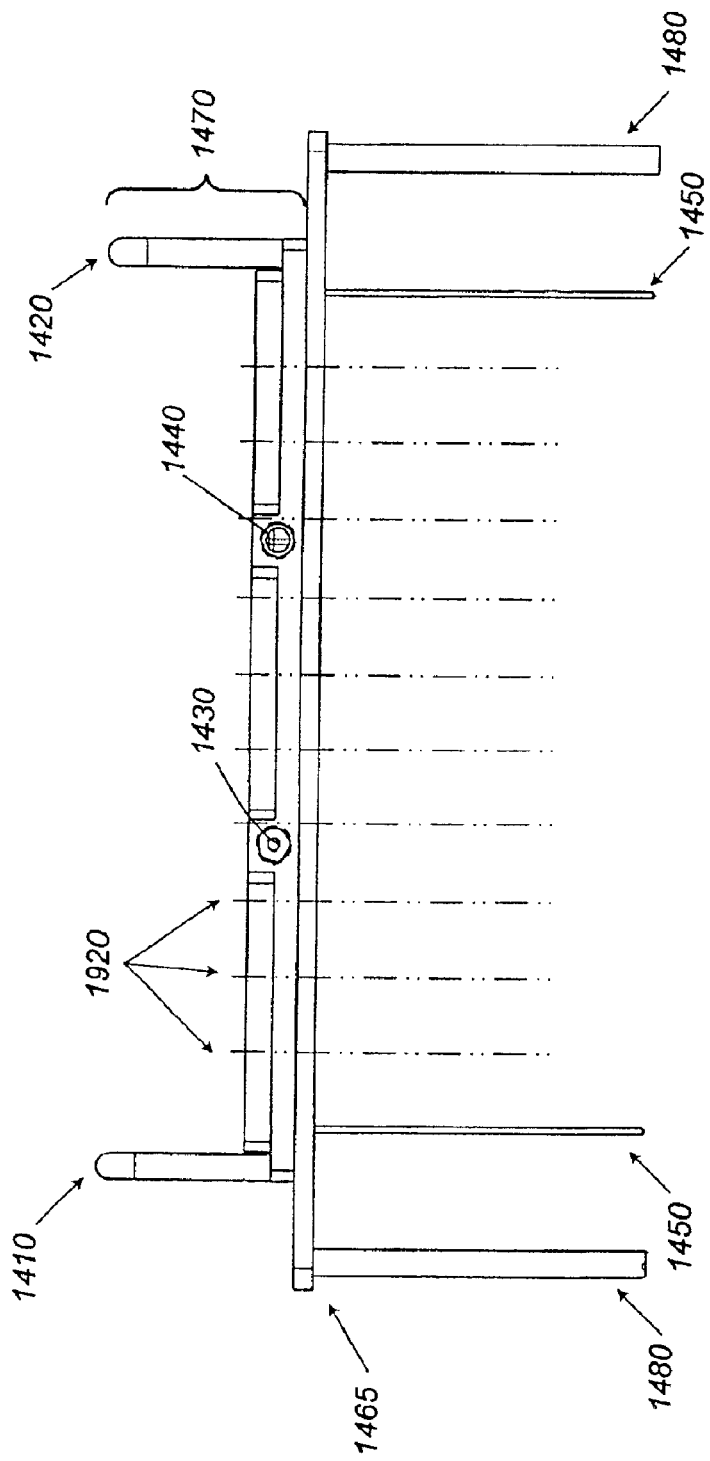
FIG. 21 is a schematic drawing that provides a side view of the gas distribution arrangement as shown in FIG. 14.

Second plate 1470 typically comprises a set of apertures as described above, which correspond to the set of apertures in plate 1465. These apertures are used, e.g., for liquid dispensing and/or venting. The apertures in the two plates connect to form a passageway that extends through both plates for access to placement wells 1350. The apertures are closed off from the interior space and can be capped using a lid as shown in FIG. 14 when a sealed system is desired. In addition, second plate 1470 typically comprises the gas inlet, e.g., inlet 1430, and an interior space through which gas is flowed. FIG. 21 provides a side view of the gas distribution arrangement as shown in FIG. 14. For example, FIG. 21 shows cannulas 1450 extending below the first plate into the placement wells and apertures 1920 extending through the first plate and the second plate.

Figure 20:
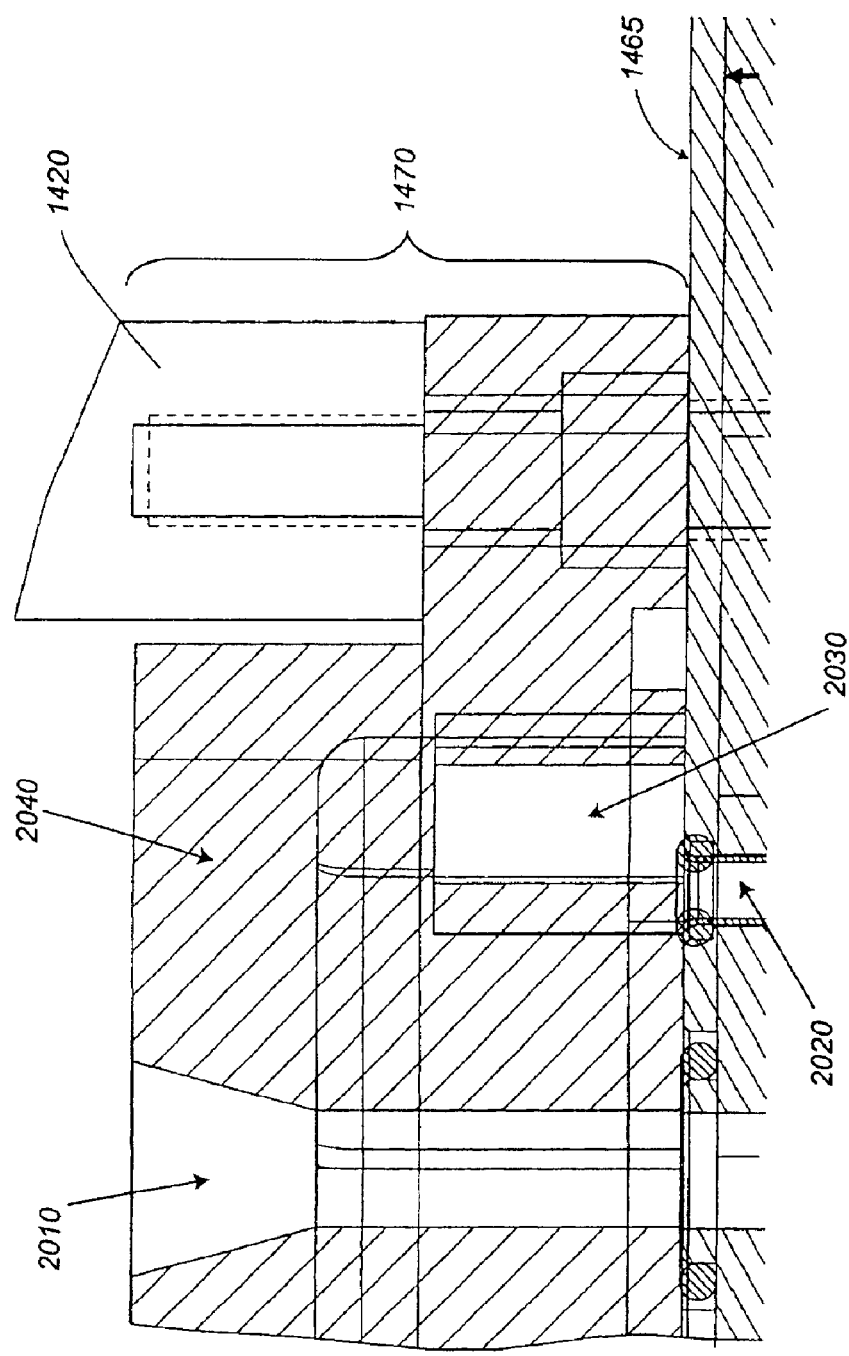
FIG. 20 is a schematic drawing illustrating a cross-sectional view of a gas distribution arrangement including top and bottom plates taken along line B—B of FIG. 19.

FIG. 20 illustrates a cross-sectional view of the gas distribution arrangement of FIG. 14, which comprises a first and a second plate. Top plate 1470 is attached to bottom plate 1465, e.g., using screws positioned through apertures 1830, and 1840. The first plate, which is on the bottom, comprises apertures 2010 and cannulas 2020. The apertures are open holes in first plate 1465, which align with similar apertures in second pate 1470, the top plate. The cannula are inserted into the first plate through another set of apertures secured with O-rings, e.g., to form a seal between the top and bottom plates. The cannulas extend from the top surface of plate 1475 into placement wells 1350 such that they are easily positioned in an array of sample vessels held in the placement wells. Cannula 2020 does not extend into plate 1470, but abuts it. Adjacent to where cannula 2020 abuts plate 1470 is venting space 2030 which couples the cannula to interior space 2040 of the top plate through which interior space gas flows in through an inlet, e.g., inlet 1430.

Figure 15:
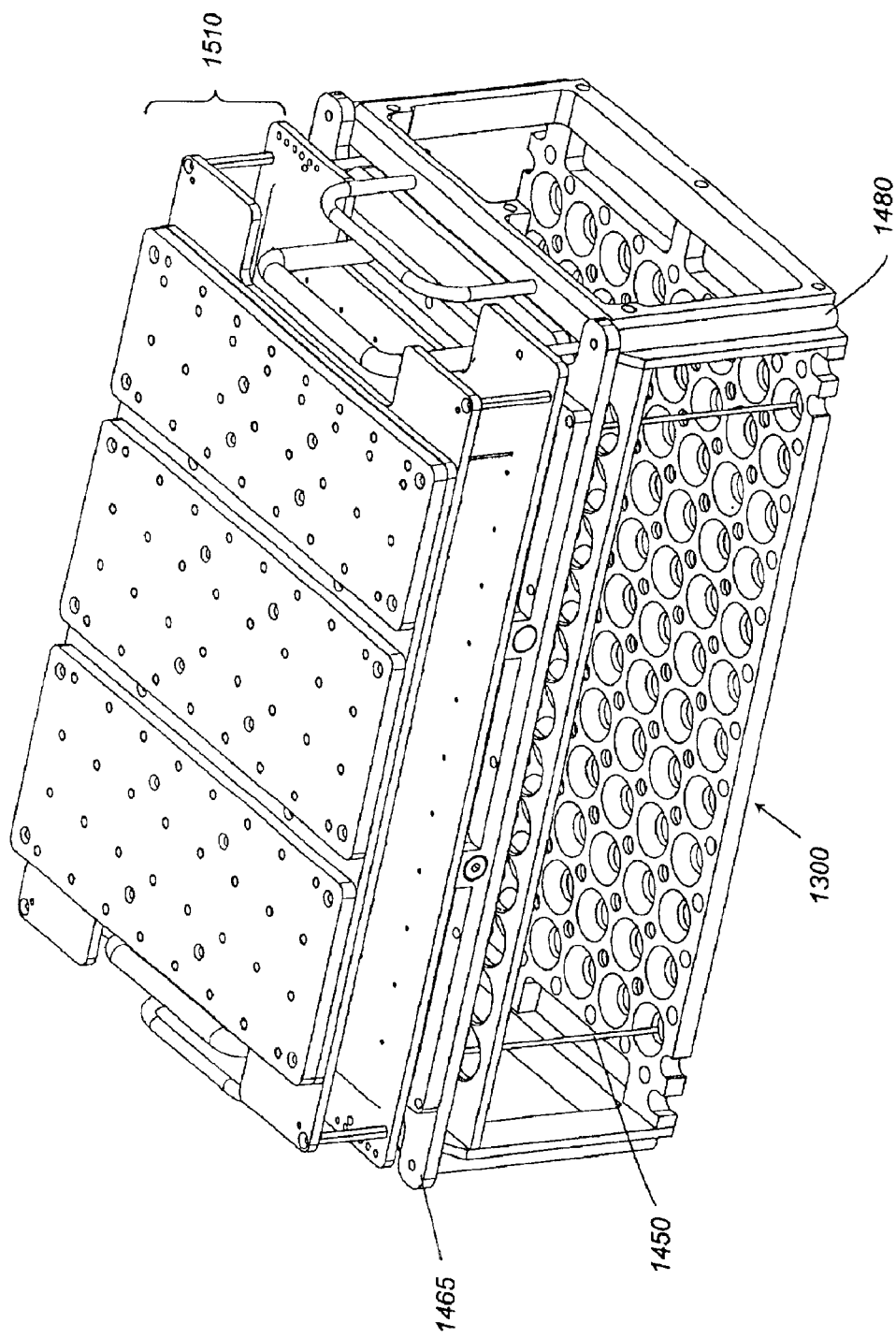
FIG. 15 is a schematic drawing that illustrates the container frame of FIG. 13 coupled to an alternative gas distribution arrangement configured for liquid additions.
Figure 16:
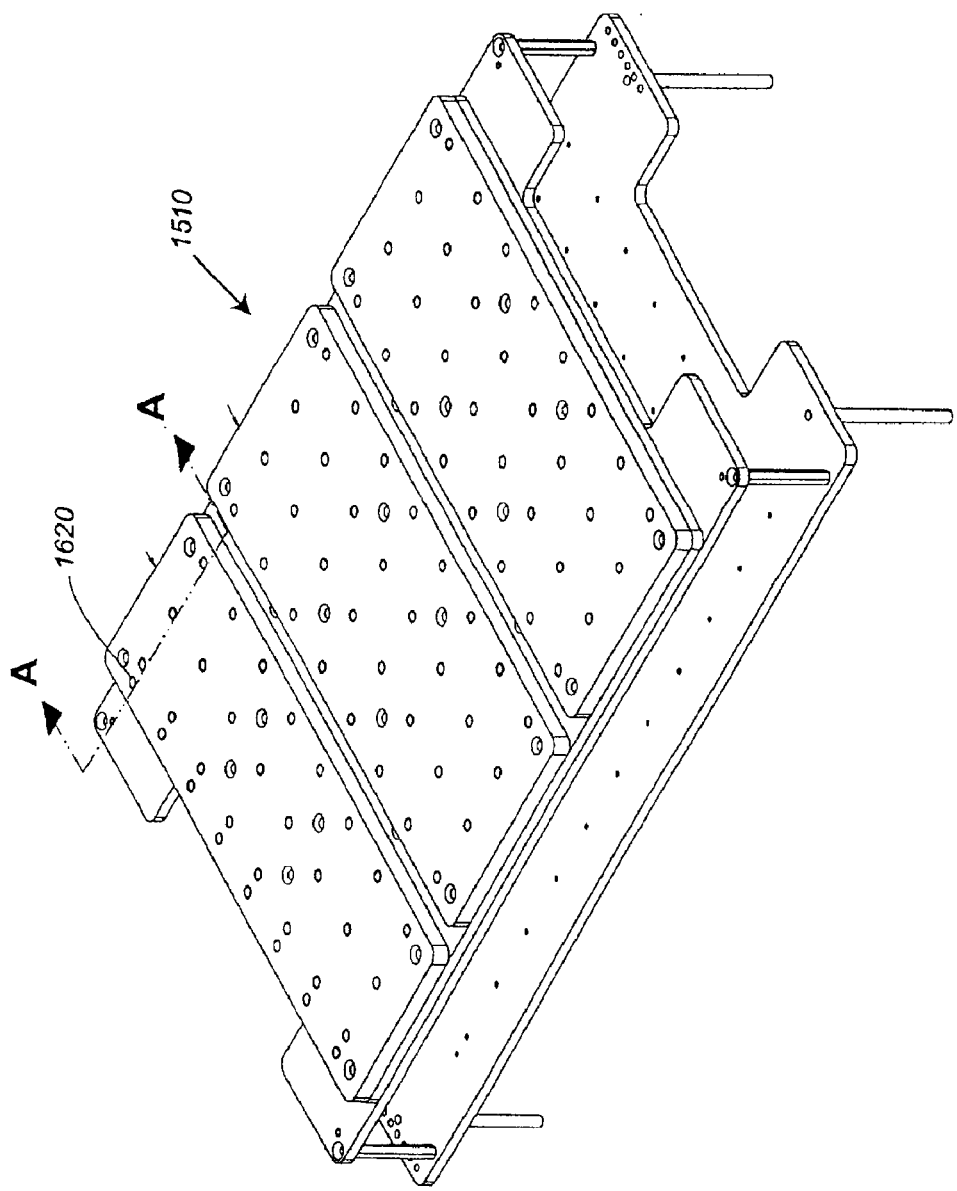
FIG. 16 is a schematic drawing that illustrates the gas distribution manifold with a liquid addition capacity of FIG. 15.
Figure 17:
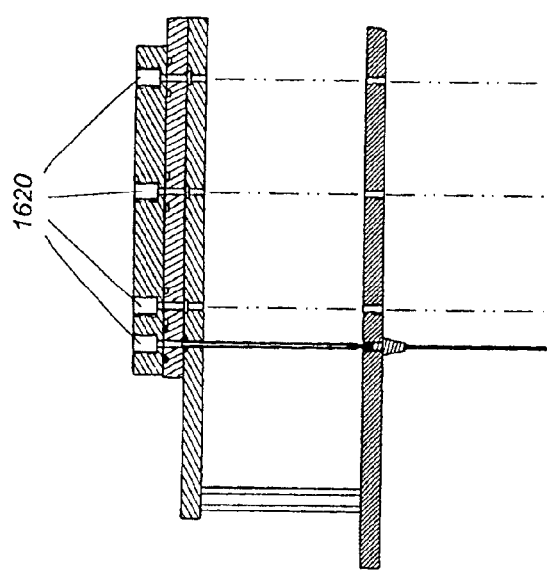
FIG. 17 is a schematic drawing that illustrating a cross-sectional view taken along line A—A of FIG. 16.

FIG. 15 illustrates a container frame with a liquid addition manifold assembly coupled to it. Container frame 1300 is shown with first plate 1465 positioned on top using pins 1480. Second plate 1470 is positioned on top of the first plate and liquid addition manifold 1510 is shown on top of the second plate of the gas distribution system. The liquid addition manifold is optionally used to add liquid into the sample vessels, e.g., through corresponding sets of apertures in the first and second plate. FIG. 16 illustrates liquid addition manifold 1510 in more detail, e.g., apertures 1620, which align with apertures on the first and second plates of the gas distribution arrangement. Apertures 1620 are used to deliver liquid reagents into the sample vessels contained in the apparatus. Manifold 1510 is placed, e.g., using pins, on top of the gas distribution system. In addition, FIG. 17, a cross-sectional view of the liquid addition manifold along line A—A, illustrates how pipettes or additional cannulas are used to dispense liquid into the sample vessels. For more information on fermentors, see, e.g., U.S. patent application Ser. No. 10/071,842 entitled, "Multi-sample Fermentor and Method of Using Same," filed Feb. 8, 2002 by Downs et al.

3. Example Automated Fermentor System

Figure 7:
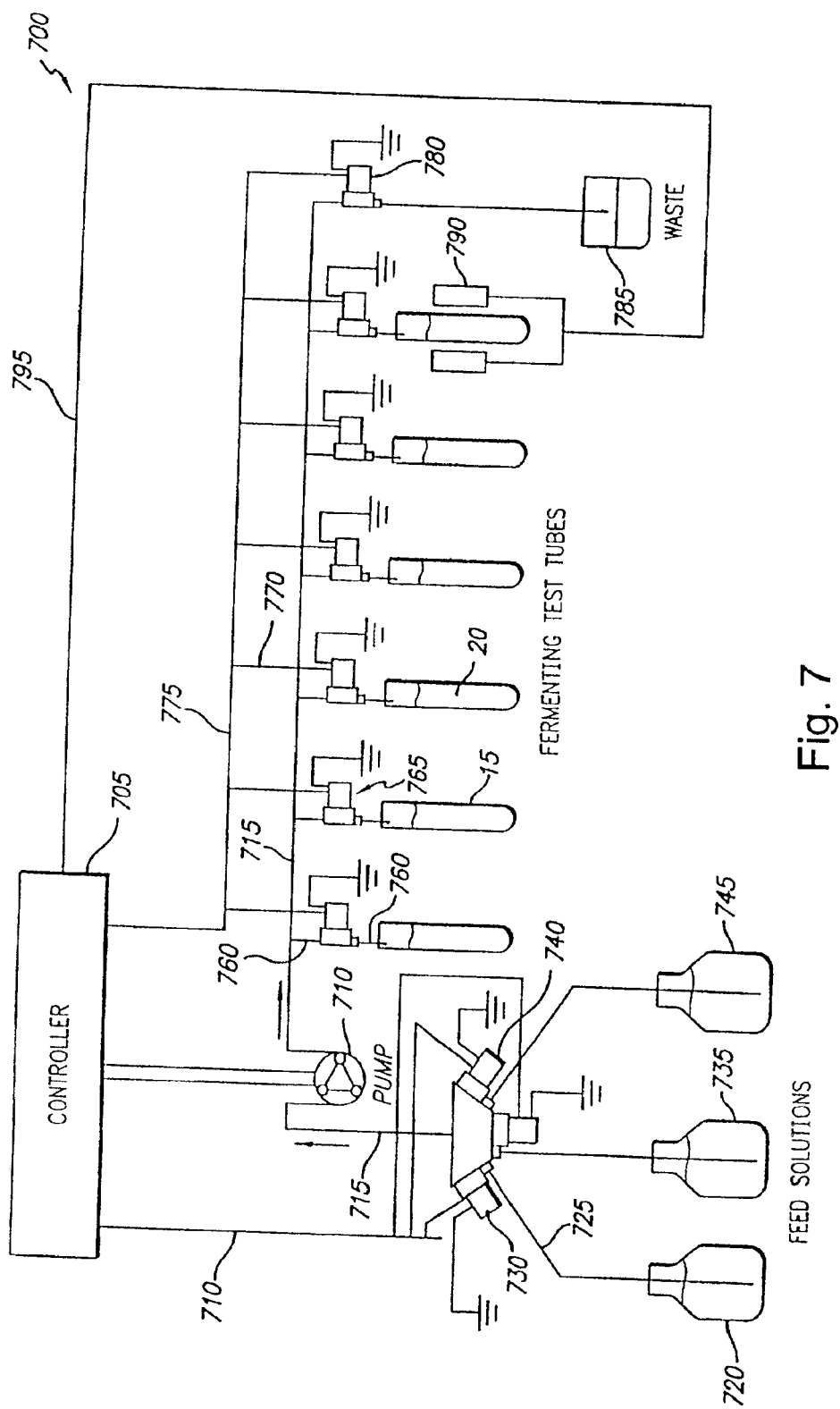
FIG. 7 is an automated fermentation assembly in accordance with the present invention.

FIG. 7 illustrates an example of an automated fermentation apparatus. Process controller 705 monitors and controls various components of apparatus 700 and preferably is a programmable computer with an operator interface. Alternatively, process controller 705 is any suitable processor that coordinates multiple components of apparatus 700, such as timing mechanisms, adding solutions, adjusting temperature, adjusting gas flow rates and gas mixtures, detecting measurements, and/or sending an alarm or notification prompting operator intervention. Electronic couples 710, 755, and 795 connect various components of fermentation apparatus 700 to process controller 705. For example electronic couple 710 enables controller 705 to start, stop, and monitor solution flow from feed solutions 720, 735, and 745. Likewise, electronic couple 775 enables controller 705 to start, stop and monitor reagent dispensing into sample vessels 15. Electronic couple 795 also enables controller 705 to transmit and receive information from sensors 790 as well as monitor and adjust temperature controlled areas. Other coupling devices are also optionally used in the present invention.

In one embodiment of fermentation apparatus 700, feed solutions 720, 735, and 745 are pumped (either singly, in combination, sequentially, or collectively) from individual feed tubes 725 into dispensing tube 715. Selecting the appropriate solenoid determines which feed solution is pumped through dispensing tube 715. For example, solenoid 730 controls flow from feed solution 720 through feed tube 725. In another application, a mixture of feed solutions 720 and 735 are simultaneously pumped into dispensing tube 715. In another application, feed solution 720 is fed into dispensing tube first, followed by an incubation period (directed by controller 705), followed by feed solution 735 being pumped into dispensing tube 715. Different combinations of feed solutions are optionally used and more or fewer feed solutions may be used with apparatus 700 according to any desired application.

Using pump 710, which is optionally a peristaltic pump, dispensing tube 715 transfers feed solution to an individual dispensing tube 760. Each individual dispensing tube 760 corresponds to an individual sample vessel 15 and tube 760 is positioned such that feed solution 720, for example, is transferred volumetrically from dispensing tube 760 into its corresponding sample vessel 15 once solenoid 765 is opened. Each solenoid 765 corresponds to an individual sample vessel 15. Volumetric dispensing of feed solutions is controlled by process controller 705 which preferably controls the amount, the rate and the time of dispensing. Dispensing tube 760 is optionally composed of plastic, metal, or any material that is non-reactive to the feed solution being dispensed.

In one embodiment, delivery solenoids 765 work in conjunction with pump 710 and controller 705 to deliver multiple feed solutions such as feed solutions 720, 735, and 745 into individual sample vessels 15. Each solenoid 765 corresponds to a sample vessel 15 and the solenoids 765 are manifolded together and fed by the output of a single peristaltic pump 710. Each solenoid 765 preferably opens sequentially in order to dispense a volumetric amount of feed solution 720. However, parallel addition is also contemplated within the present invention.

In one embodiment, feed solution 720 introduces nutrients into fermentation medium 20 through dispensing tube 715 using pump 710 and solenoid 765 to deliver solution 720 to individual dispensing tube 760. After addition of feed solution 720, solenoid 730 is closed and solenoid 740 corresponding to rinse solution 745 opens. Pump 710 delivers rinse solution 745 through dispensing tube 715, thereby rinsing dispensing tube 715 with solution 745, which is then flushed into waste container 785. Solenoid 780 controls flow from dispensing tube 715 into waste container 785. Feed solution 735 is then pumped through dispensing tube 715 and dispensed through tube 760. Dispensing tube 715 is rinsed again with rinse solution 745 before another addition. Solenoids 765 are preferably located very near to dispensing tube 760 in order to minimize dead volume downstream. In this way, dispensing tube 715 accurately delivers a known amount of feed solution 720 and 735 without cross contaminating or fouling the next or different addition of feed solution through dispensing tube 715. Accordingly, each addition is volumetrically precise with a minimal, known amount of feed solution from a previous addition diluting the next addition. In this way, feed solutions such as additional nutrients, trace minerals, vitamins, sugars, carbohydrates, nitrogen containing compounds, evaporating liquids, pH balancing compounds, buffers, and other liquids may be added to fermentation media 20 in an automated, yet highly precise manner.

Coordinated by process controller 705, various components may be activated either at pre-determined time intervals or in response to the measurement of some physical property within sample vessel 15. For example, in one embodiment, an operator programs process controller 705 to incubate sample vessels 15 for a predetermined time period at a particular temperature, add a desired amount of feed solution 720, and incubate further for another pre-determined time period at a different temperature. Any suitable combination of fermentation conditions may be programmed into process controller 705, which optionally comprises a computer, computer network, other data input module, or the like.

In a preferred embodiment, process controller 705 coordinates temperature control, the addition of feed solutions, adjustment of gas rates and gas mixtures, incubation periods, and rinsing in response to data received from sensors 790. Sensors 790 are optionally located inside or outside of individual sample vessels 15. Sensors 790 can detect color changes spectrophotometrically, monitor evaporation rates, measure changes in optical density, detect light changes photometrically, detect pH changes, electrolytically measure redox potentials, monitor temperature fluctuations, or detect other physical changes and transmit this data to process controller 705. In response, process controller 705 accordingly adjusts various components of apparatus 700. For example, by measuring the redox potential, sensors 790 detect when a fermentation sample is being over-oxygenated or over-provided with another gas and process controller 705 accordingly adjusts the gas flow or gas mixture ratio. As another example, process controller 705 can respond to a change in pH, as detected by sensors 790, by adding a pH buffer from feed solution 720. In one embodiment, maximum protein expression may be detected by monitoring light emission, at which point fermentation is halted to minimize wasting fermentation resources after optimum fermentation yield has been reached.

Because of the uniformity of each fermentation medium 20, cannula 22, and dispensing of feed solutions 720, very few, for example, one, sensor 790 is all that is necessary to monitor the entire array of sample vessels 110. Alternatively, when sample vessels 15 contain different fermentation media 20 or undergo different fermentation conditions, numerous sensors 790 are optionally employed.

D. Method of Using Vessel to Ferment a Sample

The multi-sample fermentors described above are used for simultaneously fermenting a plurality of samples, e.g., in a container frame that is transportable, e.g., to a processing station. The present invention also provides methods of using such fermentors, e.g., in conjunction with one or more processing steps. For example, the methods provided typically comprise providing a plurality of sample vessels in a container frame, each of which sample vessels contains a sample of about 50 to about 100 milliliters, more typically 65 ml. The samples are fermented in the sample vessels within the container frame.

Fermentation is used herein to refer generally to any process in which cells are used to convert raw materials, e.g., water, air, sugars, mineral salts, nitrogen sources, and the like, or enzyme substrates into desired products, e.g., proteins. Types of cells used include, but are not limited to, animal cells, yeast cells, and bacterial cells, e.g., *E. coli, Bacillus*, and the like. The cells are typically grown in a growth medium and then products are harvested. Fermenting typically involves simultaneously delivering gas to each of the sample vessels through a plurality of cannulas associated with the sample vessels, e.g., to aid growth of the cells. For example, the methods typically comprise attaching a fermentor head as described herein to a container frame containing the plurality of samples to be fermented. Once fermented, the samples are transferred to a post-processing station, e.g., a centrifuge. Typically, the post-processing station is configured to accept the same sample vessels in which the samples were fermented. In addition, some processing stations are configured to receive the container frame containing the sample vessels, e.g., a dispensing or aspirating station. An example method is described below and in FIGS. 4 and 5.

FIG. 4 describes fermentation method 300 practiced in accordance with the present invention. Block 310 provides for a plurality of sample vessels 15. By providing a number of smaller volume fermentation vessels, this method is more advantageous than production scale fermentation methods that use bulk fermentation vessels, in that smaller volumes of growth medium are more predictable in their yield and nutrient needs than are standard production scale volumes that are utilized in bulk fermentation methods. The number of sample vessels that may be fermented at any one time is unlimited by the present invention, and instead is only limited either by the configurational practicalities of any one fermentation apparatus or by the number of sample vessels that may be handled by further processing steps in the production.

Block 315 arranges a plurality of sample vessels into an array, e.g., a rectangular 8 by 12 array. However, the array is optionally configured in any shape that is practicable for the fermentation apparatus. For example, sample vessels are optionally arranged in a rectangular array, a honeycomb configuration, or a linear array.

Block 320 arranges a plurality of cannula into an array corresponding to the sample vessels. According to the present invention, each cannula in this cannula array corresponds to an individual sample vessel in the sample vessel array, which are arranged in block 315. In one embodiment, the plurality of cannula is limited by the number of sample vessels arranged in block 315.

Block 325 creates a gas distribution arrangement for delivering oxygen and/or one or more other gases to a fermentation media in the sample vessels. For example, one embodiment fastens a cannula array to a gas distributor, which is connected to a manifold. The cannula array may be fastened by any means achieving a liquid-tight seal. For example, cannula are optionally connected via a union connector to a gas distributor. Alternatively, cannula are pneumatically connected to the distributor, or the cannula array and gas distributor are optionally molded as a single unit. In another embodiment, the distributor connects directly to a gas source without using a manifold. The methods of creating a gas distribution arrangement are optionally achieved using any method of uniformly delivering oxygen and/or one or more other gases from a gas source to a gas distributor such that gas is delivered to each individual sample vessel selectively or collectively by way of a corresponding cannula.

Block 330 transports the container frame containing the plurality of sample vessels to a temperature controlled area. Other methods known to those of skill in the art for controlling temperature are also contemplated within the present invention. For example, the container frame is optionally transported to a heated gel bath or a controlled temperature room used to maintain a constant temperature.

Block 335 positions the gas distribution arrangement created in block 330 on top of the container frame, e.g., using screws or by merely being placed on top and held in position by a groove assembly as shown in FIG. 14. From this configuration, the array of sample vessels is fermented in block 340.

Once fermentation is complete, block 345 removes the gas distribution arrangement from the container frame. The sample vessels are optionally transferred from the container frame directly to a post-fermentation processing station in block 350, e.g., by manipulating a gripping surface located on each sample vessel. This post-fermentation processing station includes any processing step where the fermentation product may be processed directly from the sample vessel. For example, the array of sample vessels may be transferred, either manually or robotically, from the container frame directly to an automated centrifuge. Alternatively, sample vessels may be transferred to an aspirating station or detecting station. In other embodiments, the sample vessels are not removed from the container frame but remain in it for further processing, such as dispensing or aspirating, using a dispenser or aspirator configured to coordinate with the array of sample vessels in the container frame.

In block 350, the fermentation product in the sample vessels is directly transferred into a post-fermentation processing station and in block 355 the fermentation product is directly processed in the sample vessels themselves. For example, in one embodiment, sample vessels are transferred directly to a centrifuge station in which the sample vessels are positioned directly inside the centrifuge such that the sample vessels act as centrifugation tubes and the fermentation product is centrifuged according to methods known in the art. Further processing steps such as aspirating, reagent dispensing, or detecting also optionally occur directly in the sample vessel used in the fermentation process. In this way, the fermentation vessel provides a sample vessel that holds the sample throughout the entire production process, thereby eliminating excess waste from transferring sample material from sample vessel to sample vessel as well as decreasing the cost of washing and sterilizing a fermentation apparatus in addition to sample vessels from each production process step. Other multiple process productions or analyses may also be practiced in accordance with the present invention.

In FIG. 5, block diagram 400 shows how the present invention is integrated into a multiple step, multiple process production. Block 410 depicts a processing station prior to fermentation. In one embodiment, fermentation broth and fermentation nutrients are added to sample vessels at prior processing station 410. Other processing steps involved in a multiple step production or analysis are also contemplated in accordance with the present invention. For example, bacteria colonization may occur in sample vessels at prior processing station 410. Example preprocessing steps include, but are not limited to, deionization, e.g., of solvents, pasteurization of materials, and mixing, e.g., of cell nutrient broths and the like. Such steps are typically used to process the raw materials, such as water, cell broths, sugars, nitrogen sources, and the like, used for the fermentation. Transporter 420, e.g., a robot, a technician, a conveyor belt, or the like, is optionally used to transfer the sample vessels from processing station 410 to a fermentation apparatus such as fermentation apparatus 100. Other embodiments of a fermentation apparatus practiced in accordance with this invention may also be used. For example, the fermentation apparatus shown in FIG. 14 or in FIG. 1 is optionally used.

It will further be appreciated that transporter 420 may transfer the sample vessels individually, in groups, or in an array configured for the fermentation apparatus. For example, in one embodiment, a container frame transports the sample vessel array to fermentation apparatus 100. Similarly, after fermentation, transporter 430 transports sample vessels from a fermentation apparatus to a post-fermentation processing station 410. In one embodiment, transporter 430 transports a container frame holding an array of sample vessels to a centrifuge processing station 410. Post-processing station 410 is optionally any other processing step occurring in a multiple process or analysis, such as an aspirating step, a dispensing step, or a detecting step. Example post-processing steps include, but are not limited to, precipitation, deionization, chromatography, evaporation, filtration, centrifugation, crystallization, drying, and the like. These steps are generally directed to purification, retrieval, and concentration of materials produced in the fermentation. In this manner, multiple processing steps are executed on each sample contained in the same sample vessel, thus enabling fermentation processes to be incorporated into high throughput or other multiple process systems. Example fermentation conditions are described below.

The present invention preferably uses fermentation conditions that lead to high level production of soluble proteins. These fermentation conditions may employ the use of high levels of yeast extract and bactotryptone (rich media, referred to as terrific broth or TB). Secondly, this media is optionally supplemented with 1% glycerol (additional carbon source). Lastly, the media preferably is typically buffered with 50 mM MOPS. Alternatively, a defined media comprising amino acids and 50 mM phosphate as opposed to MOPS is used. The first two additions allow the cells to be grown for up to about 10 hours without apparent loss of nutrients. The highly buffered media prevents the cells from being exposed to high levels of acid (low pH) which routinely occurs during fermentation.

Surprisingly less than 5% of human proteins expressed in normal Luria Broth or LB media, are typically found to be soluble. However, using the above media, 15–20% of human proteins expressed in *E. coli* now appear to be soluble.

In a preferred embodiment, the fermentation media is prepared as follows. TB media is prepared in 7L batches. Antibiotics are not added to TB media until the day it will be used for a fermentation run. To prepare the 7L bath, the following steps are performed: (1) Fill a clean 10L pyrex bottle with ~4L DI $H_2O$ or 18 megohm water, add a large stirbar; (2) Add 168 g Yeast Extract; (3) Add 84 g Tryptone; (4) Add 70 ml Glycerol; (5) Stir on stirplate until completely dissolved; (6) QS to 6.3L, e.g., with 18 megohm water; (7) Autoclave on the longest liquid cycle. Remove TB media from the autoclave as soon as possible, e.g., to prevent carmelization or burning of the carbon source and/or to allow for a quick cool down; (8) Store TB media at room temperature; and (9) Record process. TB Media is the same for all fermentor runs. However, Fermentor Media is not necessarily the same for all runs. For example, one difference in media is the antibiotic(s) added just before fermentation. On the same day of a fermentation run, the following may be added to TB media: (1) 350 mls of 1 M MOPS pH 7.6; (2) 7 ml Antifoam; (3) 7 ml 20 mg/ml Chloramphenicol; (4) 7 ml 100 mg/ml Ampicillin; (5) Add enough 18 megohm $H_2O$ to bring the volume up to 7L; (6) Write everything added to TB media on its label; (7) Cap tightly and shake bottle well; and (8) Record process. The above medium is only one of many possible choices known to those of skill in the art, which are optionally used with the present fermentors and methods.

Once fermentation is complete, block 345 includes removing the gas distribution arrangement from the container frame. The sample vessels are optionally transferred, e.g., manually or robotically, from the container frame directly to a post-fermentation processing station in block 350, e.g., by manipulating a gripping surface located on each sample vessel. This post-fermentation processing station includes any processing step where the fermentation product may be processed directly from the sample vessel. For example, the array of sample vessels may be transferred, either manually or robotically, from the container frame directly to an automated centrifuge (described below). Alternatively, sample vessels may be transferred to an aspirating station or detecting station. In other embodiments, the sample vessels are not removed from the container frame but remain in it for further processing, such as dispensing or aspirating, using a dispenser or aspirator configured to coordinate with the array of sample vessels in the container frame.

In block 350, the fermentation product in the sample vessels is directly transferred into a post-fermentation processing station and in block 355 the fermentation product is directly processed in the sample vessels themselves. For example, in one embodiment, sample vessels are transferred directly to a centrifuge station (described below) in which the sample vessels are positioned directly inside the centrifuge such that the sample vessels act as centrifugation tubes and the fermentation product is centrifuged according to methods known in the art. Centrifuge apparatus used with the devices, systems, and methods described herein are optionally those which are commercially available or those specifically adapted to high-throughput processes, such as those described below and in, e.g., international patent application Ser. No. 10/071,877 entitled "Automated Centrifuge and Method Of Using Same," filed Feb. 8, 2002, which is incorporated herein by reference in its entirety for all purposes. Further processing steps such as aspirating, reagent dispensing, or detecting also optionally occur directly in the sample vessel used in the fermentation process. In this way, the fermentation vessel provides a sample vessel that holds the sample throughout the entire production process, thereby eliminating excess waste from transferring sample material from sample vessel to sample vessel as well as decreasing the cost of washing and sterilizing a fermentation apparatus in addition to sample vessels from each production process step. Other multiple process productions or analyses may also be practiced in accordance with the present invention.

III. Sample Centrifugation and Purification

Previously available centrifuge systems are generally simply "stand alone" centrifuges that are difficult to incorporate into high throughput sample processing systems, because they must be manually loaded and unloaded. This is time consuming, and therefore expensive. Indeed, loading and unloading centrifuge rotors can even be dangerous, due to the weight of the rotors that are often used and the awkwardness of lifting the rotor down onto a rotor spindle, as well as due to the possible presence of hazardous materials in sample tubes which are loaded into the rotor.

While some systems have been proposed for automated loading of centrifuge rotors (e.g., "Automated System Including Automatic Centrifuge Device," U.S. Pat. No. 6,060,022 to Pang et al.) these systems have generally only proposed using simple robotics for the loading and unloading of sample containers, one a time, to and from the rotor. Furthermore, no attempt has been made in these systems to integrate sample processing and centrifugation.

The present invention takes a very different approach to the integration of centrifuge and sample processing elements. In particular, the systems of the invention are typically configured to provide sample processing while sample containers are in physically located in the rotor. This is accomplished by providing transport robotics coupled to sample processing components that are designed to be inserted into the sample containers. These sample processing components can include essentially any components that processes a sample and that can be configured to be inserted into a sample container. These include, without limitation, fluid handling components (e.g., dispensing and/or aspirating tubes), sample resuspension components (e.g., mixing or vibrating apparatus such as mixer elements or sonication rods), heater rods, refrigeration rods, heat sinks, detection elements (e.g., pH detectors, fiber or tube optics, temperature probes, conductivity probes), electrical probes, and many others that will be apparent to one of skill. Moreover, the transport robotics can be coupled to the sample processing components to provide for the simultaneous insertion of multiple sample processing components into one or multiple sample containers. The elimination of the need to load and unload samples to sample processing stations substantially increases throughput of the system, as does the ability to multiplex the sample processing components.

An additional aspect of the invention is that sample vessel transport robotics can be provided such that multiple samples can be loaded into a rotor simultaneously. This speeds the loading and unloading of samples into rotors and increases throughput of the overall system.

Rotors of the invention are optionally provided which facilitate insertion of sample processing components into the rotors. For example, rotors of the invention have sample receiving elements (e.g., cavities, depressions, holes, apertures, buckets, or the like, suitable for receiving a sample vessel such as a test tube), optionally arranged in clusters of elements.

Clusters of sample receiving elements are characterized in that they have one of at least two characteristics. First, the clusters typically display a distinct spatial grouping of the sample receiving elements. That is, when viewing the rotor, the sample receiving elements are arranged in spatially distinct groupings. Second, the clusters typically have sample receiving elements having substantially the same longitudinal axes. In most cases, the longitudinal axes of the clusters is not perfectly vertical, e.g., at least 1° off of vertical, typically about 5° or more off of vertical. In general, when referring to numeric ranges such as "about 5°", it will be appreciated that an equivalent range may be substituted.

For example, where the rotor is a fixed-angle rotor, sample receiving elements such as rotor cavities can be clustered in sets of non-vertical cavities, where each member of the cluster has substantially the same longitudinal axis. This facilitates insertion of sample processing components into the cavities, by permitting multiple sample processing components to be arranged along a single longitudinal axis as well, permitting simultaneous insertion of the sample processing components into the cluster. This increases the ability to multiplex simultaneous sample processing in the rotor, increasing the throughput of the system. Similarly, the clustered nature of the sample receiving elements permits a centrifuge vessel loading robot to arrange the vessel insertion components of the robot along the same axis, facilitating simultaneous loading of vessels into the clusters and, again, increasing the overall throughput of the system.

The system can include any of a variety of additional traditional or non-traditional sample storage or processing components as well. For example, the system can include refrigeration components (indeed, any part or all of the system can be refrigerated to prevent sample degradation), sample purification apparatus (e.g., sample/ fraction collectors, sample purification columns, etc.), sample analysis apparatus (sample electrophoresis apparatus, spectrophotometers, mass spectrometers, etc.), station robotics that move samples or sample vessels between stations, sample vessel cleaners that clean sample vessels for re-use in the system, and tracking/inventory systems that track the status and/ or location of samples in the systems.

Accordingly, the present invention alleviates, to a great extent, deficiencies of known centrifugation processes, e.g., by providing an automated centrifuge system that can incorporate any of several processing steps, e.g., within a single processing station or set of related stations. Typically, the automated centrifuge system includes at least one centrifuge rotor defining a sample receiving element such as a cavity. One or more movable sample vessels are structured to be insertable into the cavity. A transport is configured to position and insert one or more movable sample vessels into the cavity. Once the sample vessels are inserted into the cavity, the system performs a sample treatment (e.g., fluid movement) function such as aspiration, dispensing, sonication or the like.

One embodiment of the automated centrifuge system employs a centrifuge rotor defining a cluster of sample receiving elements such as rotor apertures (also referred to as "holes") located in the rotor. Each aperture has a longitudinal axis and the longitudinal axes of the cluster of rotor holes preferably are substantially parallel, although any arrangement of rotor holes may be used that can suitably receive and position sample vessels. A group of movable sample vessels (e.g., centrifuge tubes) are positioned by a transport so that the movable sample vessels are capable of being inserted into the cluster of rotor apertures.

The automated centrifuge system of the present invention affords several advantages. For example, sample receiving elements are optionally grouped in sets with each sample receiving element in the set being substantially parallel to all the other sample receiving elements in the set. Such an arrangement permits the simultaneous insertion of a group of tubes for further processing steps, such as automated aspiration or dispensing of fluids without removing the sample vessels to a separate processing station. A sonication device can also be inserted (simultaneously or separately) with the aspiration/dispensing tube. Advantageously, suspended materials can be centrifuged, aspirated, sonicated, and centrifuged again without the removal of the sample vessels from the centrifuge and, optionally, without human intervention. The present invention introduces numerous advantages over current technology, in that multiple-step procedures involving centrifugation that formerly required substantial human involvement and physical transfer of sample vessels to separate processing stations are now incorporated into an apparatus that performs multiple step processes at a single processing station.

Moreover, the automated centrifuge system of the present invention increases the reproducibility of experimental results, thereby decreasing the possibility of operator variation or error. Accordingly, other advantages of the present invention include reducing operator error and increasing the consistency and reliability of experimental results.

In one aspect, the present invention provides an automated centrifuge system. The system optionally includes: (a) a group of sample processing elements such as movable tubes, each structured to transport a liquid; (b) a cluster sample receiving elements such as rotor holes located in a rotor, arranged to receive the group of sample processing elements; and (c) a transport holding the sample processing elements and constructed to substantially simultaneously move the group of sample processing elements into the cluster.

Thus, in one embodiment, the automated centrifuge system includes: (a) a rotor; (b) a cavity located in the rotor; (c) a tube structured to be insertable into the cavity; (d) a transport coupled to the tube; and (e) a controller communicating with the transport, the controller directing the transport to insert the tube into the cavity.

In an alternate embodiment, the automated centrifuge system includes: (a) a cluster of holes located in a rotor; (b) a group of tubes configured to be received into the cluster of holes; (c) a transport operably coupled to the group of tubes; and (d) a controller that directs the transport to insert the group of tubes into the cluster of holes. The system may also include: (1) a second (or additional) rotor, the second rotor including a cluster of holes; and (2) a movable platform coupled to the transport; wherein the movable platform moves the transport to selectively position the group of tubes for insertion into the cluster of holes in the rotor and into the cluster of holes in the second rotor.

In another aspect, the automated centrifuge includes: (a) means for placing a plurality of vessels in a plurality of centrifuge rotor cavities; (b) means for substantially isolating a majority of a sample component located in each vessel by centrifugation; (c) means for re-suspending the component in a first group of vessels; and (d) means for substantially simultaneously dispensing a substance into a second group of vessels.

In still another aspect, the invention provides a method of automated centrifugation. The method includes the steps of: (a) placing a vessel in a centrifuge rotor cavity; (b) substantially isolating a majority of a component located in the vessel by centrifugation; and (c) re-suspending a majority of the component while the vessel is located in the centrifuge rotor cavity. In another aspect, the method of automated centrifugation includes the steps of: (a) arranging a cluster of cavities on a centrifuge rotor, each cavity configured to receive a sample; (b) inserting a set of elongated tubes into the cluster of cavities, each tube being inserted into a corresponding cavity for depositing a liquid in each cavity; and (c) centrifuging the liquid and the sample.

The inventions also features a centrifuge rotor. The rotor includes a cluster of sample receiving elements located in the centrifuge rotor, each including a longitudinal axis. The longitudinal axes of the sample receiving elements in the cluster are substantially parallel.

Other aspects of the invention feature: (a) automated loading and unloading of the centrifuge rotor using a robot; (b) automated manipulation of samples in vessels in a centrifuge rotor using a robot; (c) an automated method for moving samples into cavities of a centrifuge rotor using a robot; (d) an automated method for manipulating samples in vessels in a centrifuge rotor using a robot; (e) controller logic (e.g., the logic for controlling the various automated operations of the system, e.g., system software comprising instructions and/or code embodied in a computer readable medium), as well as the sample tracking logic; and (f) an overall automated method.

The number of various elements or steps of the invention may be modified. For example, in preferred embodiments, the rotor body may comprise 1, 2, 3, 4, 5, 6, 7, 8 or any whole number of clusters and each cluster may have 1, 2, 3, 4, 5, 6, 7, 8, 9, 10, 11, 12, 13, 14, 15, 16 or any whole number of cavities. The number of cavities or clusters can thus be, for example, any integer between 1 and 100, e.g., between 1 and 50 or, e.g., between 1 and 25. In addition, the robot is capable of positioning at least 2 centrifuge vessels, for example, into cavities in a same cluster of the centrifuge rotor at the same time. Again, any number of centrifuge vessels can be positioned by the robot in such a manner, a number that corresponds to the number of cavities. Finally, a plurality of sample processing elements such as sample probes are capable of performing a function on at least 3 different samples, for example, at the same time. The sample processing elements, however, may be able to perform a function on at least any number of different samples at the same time. The number of different samples is any integer between 1 and 100, e.g., between 1 and 50, or, e.g., between 1 and 25.

The systems, devices and methods of the present invention optionally include means or steps for recognizing specific tubes or vessels, or groups of tubes or vessels, as they are placed into the centrifuge and/or mechanisms or steps for indexing or tracking one or more tubes or vessels as they are transferred from the centrifuge to another system, device or method, for example a fermentor. For example, the system, device or method may incorporate barcodes or colors to achieve the above, either manually or robotically.

Further details on rotors, sample processing and sample processing components and other elements of the systems are found below.

A. Rotors

The above provides a general discussion of the types of rotors that are suitably used in the systems of the invention and many specific examples are set forth in the figures below. Other than the clustered nature of preferred rotors, traditional methods of rotor manufacture and materials used for rotors can be used in the present invention. Rotors are manufactured from a wide variety of metals, composites, ceramics and polymers, depending on the g-forces to be experienced by the rotor, the properties of the samples to be centrifuged, and compatibility with existing centrifuges. Fixed angle rotors are particularly suitably arranged to include clusters of sample receiving elements, though swinging bucket rotor configurations can also be used (in a swinging bucket configuration, the axes of the sample receiving elements (e.g., the buckets) go to vertical when the rotor is not spinning. The general considerations for rotor design are well established and are considered to be well within the capabilities of one skilled in the art of high speed rotating machinery.

In addition to cluster rotors, traditional rotors can be used in the present invention, e.g., by arranging the sample processing components to mate with the longitudinal angles of the relevant available rotors at rest, or, e.g., by inserting sample processing components one at a time into the relevant sample receiving elements. Literally thousands of rotors are commercially available and can be used in the systems of the invention.

B. Sample Processing Components

The sample processing components of the invention are arranged for insertion into sample vessels while they are located in a rotor. The discussion above provides a general overview of the configuration of the sample vessels and many specific example configurations are set forth below. At least three general types of sample processing components can be used in the systems of the invention.

First, the sample processing components can add or remove fluid or other materials to sample vessels in the rotor. Common configurations include tubes which dispense fluid into the sample vessels and tubes which remove fluid from sample vessels (the same tube can serve both functions, or different tubes can serve these functions). The tubes can be made of any material that is substantially inert with respect to the fluids and/or the samples. Common materials include stainless metals (e.g., stainless steel), plastics, polymers, ceramics, coated materials (e.g., metal, ceramic or plastic coated with a non-stick surface such as TEFLON®) and/or the like.

Second, the sample processing components can mix or suspend sample components in the sample vessels. Common examples of such components include vibrating rods (e.g., sonication rods), rotary mixers, and the like.

Third, the sample processing components can analyze or treat the materials in the sample vessels. Common analyzer components include pH meters, thermometers, current meters, ion meters, electrodes, magnetic field detection components, radiation detection elements, optical elements (e.g., fiber optics, tube optics, lenses, photodiodes, photoemitters, etc.), spectrophotometer elements, heater or refrigeration elements (e.g., resistively heated wires, heat sinks, Peltier heaters or coolers, or the like), and many others. These elements can perform simple operations such as analyte detection (e.g., via pH detection, detection of an emitted signal such as a fluorescent emission, or the like), or can perform complex experimental operations such as controlled heating and cooling for thermocyclic reactions, cell lysis operations (e.g., via delivery of detergent or heat), or the like.

Any other available sample processing component that can be configured to be inserted into a sample receiving element can be used in the systems of the invention.

C. Sample Processing

Samples can be any of a variety of biological or non-biological components. For example, where biological samples are at issue, any of a variety of proteins, cells, cell fractions, nucleic acids, or the like can be the desirable component of the sample. Thus, the systems of the invention can include biological production components and the methods of the invention can include delivery of biological components to sample receiving elements and/or processing of components from such sample receiving elements.

An introduction to biological sample preparation, component purification (e.g., nucleic acid and/or protein purification) and many other sample preparation procedures can be found in many available standard texts, including Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (3rd Ed.), Vol. 1–3, Cold Spring Harbor Laboratory, Cold Spring Harbor, N.Y., 2001 ("Sambrook") *Current Protocols in Molecular Biology*, F. M. Ausubel et al., eds., Current Protocols, a joint venture between Greene Publishing Associates, Inc. and John Wiley & Sons, Inc., (supplemented through 1999) ("Ausubel")); Freshney (1994) *Culture of Animal Cells, a Manual of Basic Technique, third edition*, Wiley-Liss, New York and the references cited therein, Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York) and Atlas and Parks (eds) *The Handbook of Microbiological Media* (1993) CRC Press, Boca Raton, Fla.; *Protein Purification*, Springer-Verlag, New York (1982); Deutscher, *Methods in Enzymology Vol. 182: Guide to Protein Purification*, Academic Press, Inc. New York (1990); Sandana (1997) *Bioseparation of Proteins*, Academic Press, Inc.; Bollag et al. (1996) *Protein Methods*, $2^{nd}$ *Edition* Wiley-Liss, New York; Walker (1996) *The Protein Protocols Handbook* Humana Press, New Jersey, Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice* $3^{rd}$ *Edition* Springer Verlag, New York; Janson and Ryden (1998) *Protein Purification: Principles, High Resolution Methods and Applications, Second Edition* Wiley-VCH, New York; and Walker (1998) *Protein Protocols on CD-ROM* Humana Press, New Jersey; and the references cited therein.

In addition to sample processing components which are inserted into sample receiving elements, any of a variety of sample production, treatment, processing and purification systems can be incorporated into the automated systems of the invention. These can include, e.g., cell fermentation apparatus which produce cells to be delivered to a sample receiving region, sample/fraction collectors which process materials from the sample receiving region, refrigerated modules that store samples and sample materials, analysis stations that perform sample or sample component analysis (e.g., mass spectroscopy equipment, gel electrophoresis apparatus, capillary electrophoresis equipment, photodiodes or photo-emitter arrays, microscope stations, cell sorters, flow cytometers, FACS equipment, DNA chips, nucleic acid or protein blotting stations, 2-d electrophoresis stations, etc.) and the like. Many such components are set forth in the references above and are commercially available. One example cell fermentation apparatus that can be used in conjunction with the centrifuge elements herein is set forth in "Multi-Sample Fermentor and Method of Using Same" by Downs et al. Ser. No. 10/071,842.

D. System Logic

As noted herein, any component of the system can be coupled to an appropriately programmed processor or computer which functions to instruct the operation of these components in accordance with preprogrammed or user input instructions, receive data and information from these components, and/or interpret, manipulate and report this information to the user. As such, the computer or processor is typically appropriately coupled to one or more components (e.g., including an analog to digital or digital to analog converter as needed).

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation of the system carry out the desired operation. The computer or controller then receives data from the one or more sensors/detectors included within the system, and interprets the data, either providing it in a user understood format, or using the data to initiate e.g., controller instructions, in accordance with the programming, e.g., such as in monitoring and control of flow rates, temperatures, applied motor current or voltages, and/or the like.

In the present invention, the computer or controller typically includes software for the monitoring of materials in the system. These can include spreadsheet programs, database programs, inventory programs or the like. Additionally, the software is optionally used to control injection or withdrawal of material from the sample receiving elements, mixing or sonication of samples, fraction collector functions or the like.

E. Example Embodiments

The present invention provides automated systems comprising centrifuge elements, new centrifuge rotors that can be used in the system and new robotic systems that interface with the centrifuge rotors. In the following paragraphs, the present invention is described in detail by way of example with reference to the figures. Throughout this description, the preferred embodiment and examples shown should not be considered as limiting the scope of the present invention. Many equivalent embodiments are apparent to one of skill.

Described below are: (a) an automated centrifuge system, (b) the functions of the automated centrifuge, and (c) an alternative automated centrifuge system.

1. Automated Centrifuge System Comprising Purification Modules

Figure 22:
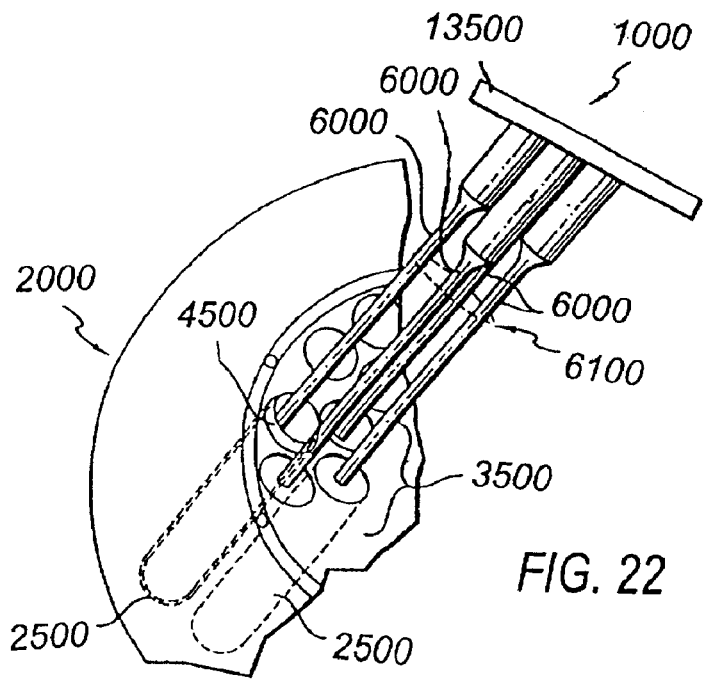
FIG. 22 is a perspective view showing a centrifuge rotor constructed according to the present invention and a group of sample vessels inserted therein.

Referring to FIG. 22, example automated centrifuge system 1000 is shown. Generally, automated centrifuge system 1000 comprises rotor 2000 having cluster 3500 of sample receiving elements (in this case rotor cavities) 2500 arranged to cooperate with group of sample processing elements (in this case tubes for fluid delivery or removal) 6100. Each cavity in the cluster holds a sample, while each tube is used to aspirate or dispense a fluid from its associated cavity. Group of tubes 6100 are moved by transport 13500 so that each tube in the group is insertable into associated cavity 2500 in cluster 3500. Accordingly, the cooperative and complementary arrangement of the cluster and group of tubes enable the efficient automated processing of samples (or any other materials) held in each cavity.

For example, rotor 2000 can be rotated until cluster 3500 is positioned in a cooperative manner with group of tubes 6100. Rotor 2000 then can be held in place when each tube 6000 is positioned so that it is insertable into corresponding cavity 2500. When positioned, transport 13500 is moved to cause tubes 6000 to be inserted into cavities 2500. Once inserted, the tubes provide a sample treatment function, e.g., a fluid movement function, such as dispensing a buffer or aspirating a fluid product into or from one of the tubes. When the sample treatment function is complete, the transport moves to cause the tubes to be removed from the cavities. With tubes 6000 removed, rotor 2000 is optionally freed and the samples centrifuged.

Several clusters 3500 preferably are arranged radially on rotor 2000. As the rotor is rotated, different sets of cavities 2500 are positioned to receive group of tubes 6100. In such a manner, each set of cavities 2500 in rotor 2000 is acted upon by the same group of tubes 6100, in a sequential manner. With automated centrifuge system 1000, rotor 2000 can be loaded with many samples, and a multiple step process can be performed on each sample (or on selected samples) without any human intervention. More specifically, several centrifugation, dispensing, and aspirating steps can be performed with controlled accuracy and repeatability using the automated system. Accordingly, a process, such as a protein isolation process, can be performed more efficiently, more quickly, and more reliably than by using a conventional system.

Referring again to FIG. 22, rotor 2000 in centrifuge system 1000 contains a plurality of cavities 2500 arranged in cluster 3500. Each cavity 2500 has a longitudinal axis, and in one preferred embodiment, the longitudinal axes of each cavity 2500 in each cluster 3500 are substantially parallel to each other. Tubes 6000 that are coupled to a robotic actuator or transport 13500, which inserts the tubes into corresponding cavities. In the embodiment illustrated, tubes 6000 are arranged in a set and can be substantially simultaneously inserted into cavities 2500, because the longitudinal axes of the cavities are substantially parallel to the longitudinal axes of tubes 6000. In this manner, a plurality of tubes 6000 can be inserted into a plurality of cavities 2500.

The precise nature of the transport robotics that moves either the sample processing components or sample vessels varies according to the application and, e.g., the nature of the tubes used in the system. For example, sample processing components or sample vessels can be gripped externally by the relevant robotics, e.g., where the sample vessels comprise a mating feature that mates with the transport robotics. This can be as simple as an outside dimension of the relevant sample processing component or sample vessel, or can be more sophisticated, e.g., a lip on the sample vessels (e.g., near or at the top of the vessels), or a fitting on the sample processing component that is grasped by the robotics. In another embodiment, the relevant robotics are designed to grip the inside, e.g., of a transport vessel, e.g., via simple friction or by contacting a specialized mating feature that fits with the transport vessel.

Figure 23:
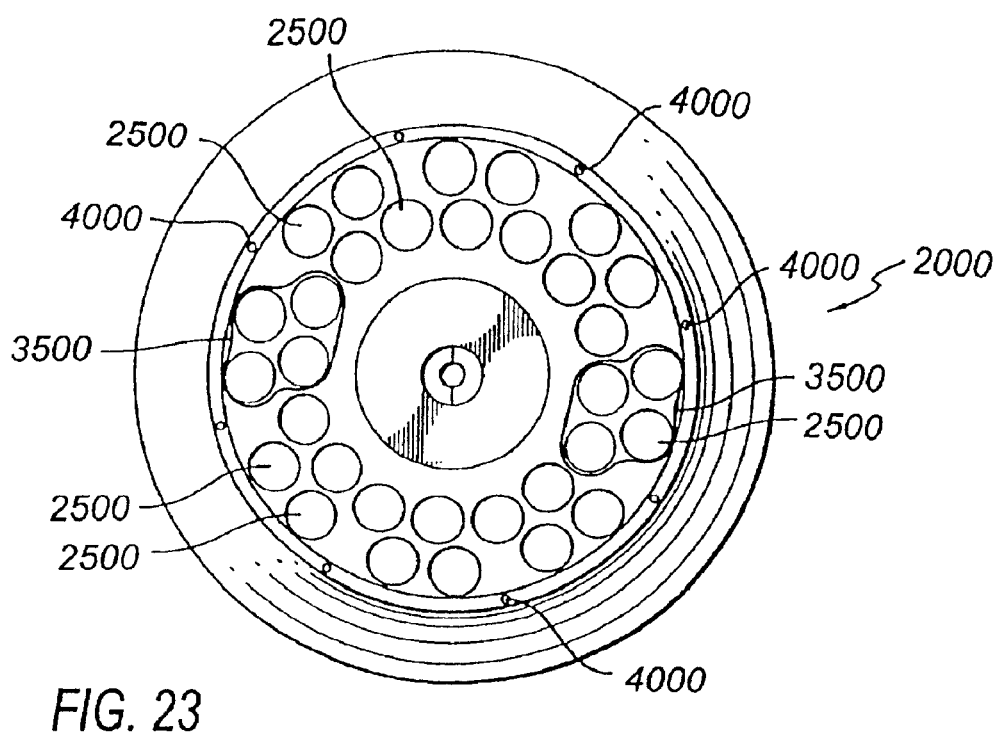
FIG. 23 is a plan view of the embodiment illustrated in FIG. 22.
Figure 23A:
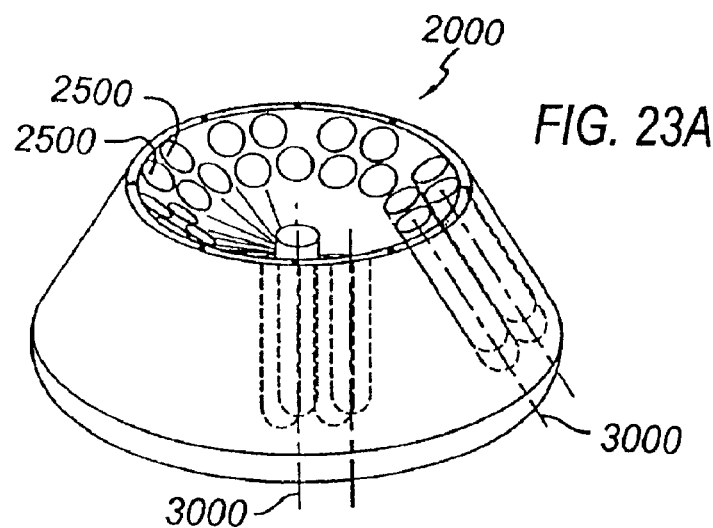
FIG. 23A is a phantom view of the embodiment illustrated in FIG. 23.

Referring to FIGS. 23 and 23A, another aspect of the present invention is illustrated. Centrifuge rotor 2000, for use in a centrifuge system, contains a plurality of cavities 2500 (e.g., rotor holes). Although, in a preferred embodiment, cavity 2500 (a sample processing component) is simply a rotor hole, the sample processing component can take other forms. For example, the component can be a well in a sample plate, a bucket in a bucket rotor, or the like.

In the preferred embodiment, each cavity 2500 has a longitudinal axis (e.g., longitudinal axis 3000) that is configured to receive a vessel 4500 (shown in FIG. 22). In a preferred embodiment, vessel 4500 holds a biological sample (a sample comprising or derived from a biological material, such as a cell, cell lysate, solution comprising a protein, solution comprising a nucleic acid, or the like). However, in an alternate embodiment, the biological sample (or any other sample) is optionally placed directly into the sample receiving element (e.g., cavity 2500) to satisfy application specific needs.

As shown in FIGS. 23 and 23A, sample receiving elements are arranged in clusters, e.g., clusters 3500. In the embodiment illustrated, cluster 3500 comprises four cavities 2500. In the illustrated embodiment, the longitudinal axis (e.g., axis 3000) of each cavity in each cluster is substantially parallel.

Figure 24:
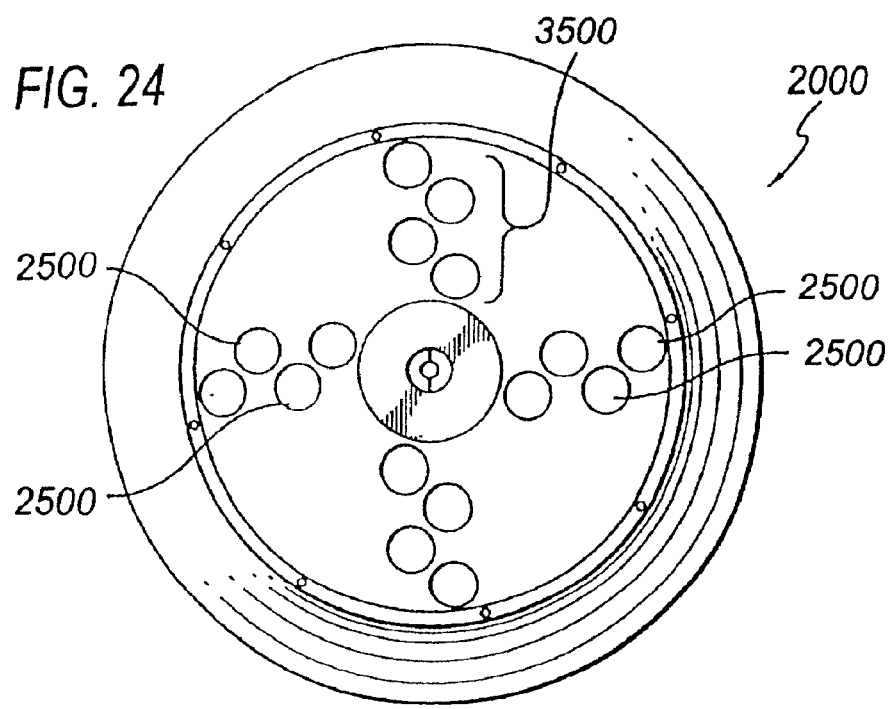
FIG. 24 is a plan view of an alternative embodiment centrifuge rotor constructed according to the present invention.

As illustrated in FIG. 24, the clusters can be arranged substantially radially in centrifuge rotor 2000. In contrast to conventional centrifuge rotors that have individual rotor holes with non-parallel longitudinal axes, rotor 2000 has clusters 3500 arranged so that the cavities are substantially parallel in a cluster while the clusters are radially arranged on the rotor. The number of sample receiving elements in each cluster can vary depending upon the size of the rotor, the size of the sample receiving elements, or other relevant factors such as the material of the rotor, the rotational operating speed of the rotor and the like. The number of clusters in a rotor can also vary. For example, in a preferred embodiment, the centrifuge rotor has thirty-two cavities arranged in eight clusters. In another embodiment, the rotor has ninety-six cavities arranged in twenty-four clusters.

As illustrated in FIGS. 23, 23A, and 24, the shape of rotor 2000 is substantially triangular with a flat base and an annular upper surface. Rotor 2000 can be made from aluminum, steel, polymers (e.g., plastics) or other suitable materials. One embodiment is manufactured from an aluminum alloy and coated with an epoxy-Teflon mixture that resists reaction with laboratory chemicals. However, the material, size and general shape of the rotor can be adjusted for application specific needs.

Each cavity 2500 of centrifuge rotor 2000 is sized to accommodate sample vessel 4500 (e.g., a test tube). Other vessel configurations can be substituted. For example, the vessel can be a well in a plate, with the plate having a plurality of sample wells. In such a manner, the plate is optionally received in the rotor.

In any case, the vessels are capable of undergoing multiple process steps, before or after the isolation process. Each of the vessels optionally has a surface that is designed to interface with a transporter which transfers the vessel to another processing station. For example, the vessels optionally comprise lips (e.g., on the outer surfaces) which can easily be gripped by a robotic apparatus. Alternately, the transporter can have generic transport mechanisms, e.g., which insert into a vessel and expand, gripping the vessels from the inside of the vessel. The transport can, thus, rely on simple frictional forces to grip the inside (or, similarly the outside) of a vessel such as a tube, or alternately, can grip a structure such as a lip, detent, groove, indentation or other structure on the outside (or, similarly, the inside) of the tube.

Vessels such as vessels 4500 are constructed such that post- and pre-isolation steps may be conducted directly on the material in the vessel. The compatibility of the vessel with other processing steps performed prior to or after the isolation process eliminates increased production costs incurred from transferring material from one vessel a second or third vessel, and then cleaning and sterilizing the used vessels. Further, eliminating one or more transfer steps increases the efficiency of the overall process, because of the decreased production time in not having to perform an extra transfer step and the increased yield from not losing any material in a transfer step.

In the illustrated embodiment, a common use for a centrifuge is to concentrate or purify materials, e.g., that are in suspension or dissolved in fluids. The fluid is placed in vessel 4500 with the vessel then being placed in cavity 2500.

Rotor 2000 is then spun by rotor motor 2700 or other suitable device to create a centrifugal force on the fluid inside in vessel 4500. The centrifuge is optionally refrigerated, e.g., to prevent sample degradation or to keep a cell culture from growing.

Rotor motor 2700 optionally accurately positions and indexes the rotor. This motor can be a single motor or can be more than one motor. That is, the motor can provide both forms of rotor control (rotation for centrifugation or for rotation to align sample receiving elements and sample processing elements).

Figure 25:
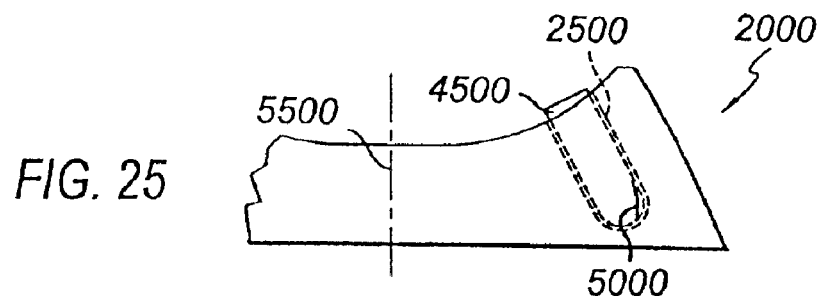
FIG. 25 is a side elevation view of a rotor cavity constructed according to the present invention.

The centrifugal force acts on the fluid and objects suspended in the fluid, separating them by density. For example, suspended particles denser than the suspending liquid tend to migrate towards the side of vessel 4500, e.g., as illustrated in FIG. 25. When the centrifugation process is complete, pellet 5000 of denser material forms on the side or bottom of vessel 4500 (depending on the angle of the vessels relative to the centripetal force exerted on them in the rotor). Illustrated in FIGS. 23, 23A, and 25, cavities 2500 are angled relative to rotor rotational axis 5500. Vessel 4500, located in cavity 2500 is thereby also angled, which positions pellet 5500 near the bottom of vessel 4500. In a preferred embodiment, this angle is about 32 degrees, but other angles can be employed to locate pellet 5000 in a different location in vessel 4500.

Figure 26:
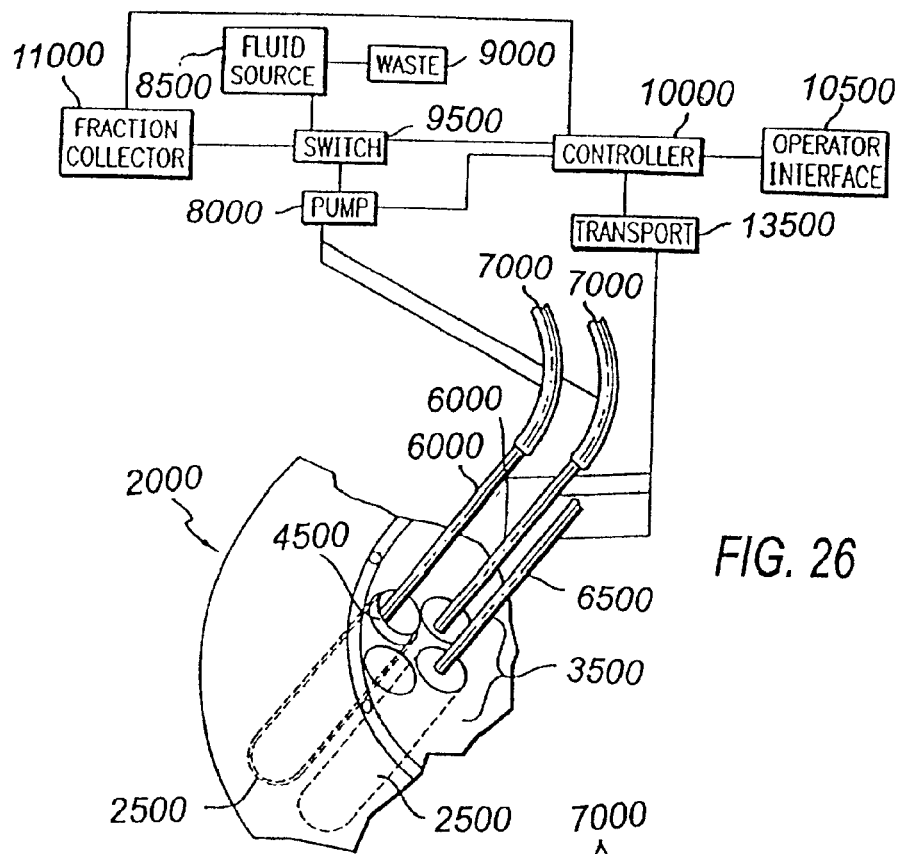
FIG. 26 is a perspective view of a section of a rotor constructed according to the present invention and a schematic block diagram of associated components of the present invention.

Referring to FIG. 26, cluster 3500 is illustrated with tube 6000 inserted in cavity 2500 containing vessel 4500. Tube 6000 is connected to hose 7000 that communicates with pump 8000. Fluid source 8500, fraction collector 11000 and waste deposit 9000 communicate with pump 8000 through switch 9500. Tube 6000 is moved into and out of cavity 2500 by transport 13500. Controller 10000 also optionally directs pump 8000 and switch 9500.

Although depicted as a single element, controller 10000 can be a control system having one or more controller elements. For example, the controller (or control system) can be a programmable logic controllers, a set of programmable logic controllers, a computer, a network of computers, or the like.

Also illustrated in FIG. 26 is second tube 6000 and sonication rod 6500. In one illustrated embodiment, the robotic actuator controls four tubes 6000 and inserts them, e.g., substantially simultaneously, into cluster 3500 (in this example including four cavities 2500). Because the longitudinal axes of the four cavities are substantially parallel, the four tubes can be inserted substantially simultaneously into the cavities. In this manner, tubes 6000 can simultaneously dispense fluid from fluid source 8500 or aspirate fluid from vessel 4500 and into waste dump 9000 or into fraction collector 11000. In another embodiment, sonication rod 6500 is coupled with each tube 6000 so that sonication can be performed during, before or after aspiration or dispensing of fluid by tube 6000. In yet another embodiment, tube 6000 is inserted in one cavity 2500 while sonication rod 6500 is inserted in a second adjacent cavity 2500, and in this manner, different steps can be performed simultaneously within each cavity 2500. Different combinations of tubes 6000 and sonication rods 6500 can be employed, with a myriad combination of aspiration/dispense/sonication procedures possible.

Tube 6000 is connected by hose 7000 to pump 8000 which, in one embodiment is a peristaltic pump. Other types of pumps (e.g., pneumatic or pressure-based) can also be employed for pumping fluids through hoses 7000. Hoses 7000 preferably are made of nylon tubing, which resist reaction with laboratory chemicals, and the tubes are preferably made of stainless steel, or a coated material which resists reaction with laboratory chemicals. In a preferred embodiment, the tubes are made of 316 stainless steel, but the tubes and hoses can be made of other suitable materials. For example, in another preferred embodiment, other types of materials such as 304 stainless steel are used in place of 316 stainless steel, e.g., where the 304 stainless steel is coated with TEFLON® or a similar non-stick coating. Similarly, sonication rod 65 is optionally made of titanium, but other suitable materials can be used for the sonication rod.

Fluid source 8500 optionally comprises buffers, washes, cleansers and other fluids and substances useful for conducting one or more desired scientific tests. For example, a variety of buffers, such as Triton X-100, DB (deoxycholate buffer), and GB (guanidine buffer), all manufactured by Sigma-Aldrich Company of St. Louis, Mo., can be employed in the fluid source 8500. In a preferred embodiment, up to six or more different fluids can be employed in the fluid source 8500, but more or fewer fluids (as necessary to conduct a specific test) can be used in the fluid source 8500.

Waste dump 9000 is configured to accept waste fluids from the pump 8000. In one embodiment, waste dump 9000 comprises a hose that runs to a container located outside of the automated centrifuge. Alternatively, waste dump 9000 can, be e.g., a trough located adjacent to fraction collector 11000. Also, waste dump 9000 can be located adjacent to rotor 2000. Switch 9500 comprises one or more switches that preferably comprise electrically driven solenoids, e.g., solenoid valves. In one embodiment, the wetted surfaces in switches 9500 include TEFLON®, or are TEFLON®-coated (TEFLON is a registered trademark of E.I. du Pont de Nemours, a Delaware corporation), but other types of switches having other types of suitable coatings or base materials can also be employed.

Referring to FIGS. 26 and 31, controller 10000 can be a specifically designed controller or a general purpose computing device such as a personal computer that includes or controls one or more programmable logic controllers. Other types of general purpose computing devices can similarly be used as controller 10000. In a preferred embodiment, a personal computer using RS VIEW software, manufactured by Allen Bradley, provides operator interface 10500, that directs controller 10000. Controller 10000 communicates with transport 13500, pump 8000, switch 9500, fraction collector 11000, and other devices on the automated centrifuge through wires or other suitable means.

Figure 27:
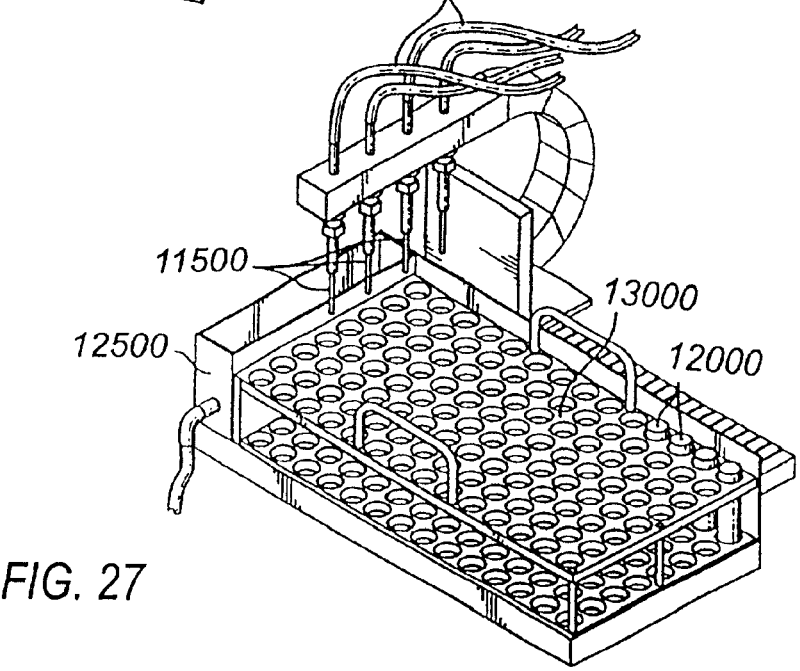
FIG. 27 is a perspective view of the fraction collector depicted schematically in FIG. 26.

Illustrated in FIGS. 26 and 27, fraction collector 11000 is connected to switch 9500 and to controller 10000. Fraction collector 11000 comprises hoses 7000 connected to one or more tips 11500 which dispense fluid obtained from one or more vessel 4500 into specimen collectors 12000 that are located in tray 13000. Depending upon the fluid in hoses 7000 and the instruction from controller 10000, tips 11500 can also dispense fluid into waste trough 12500 located adjacent to tray 13000. Specimen collectors 12000 collect material that is obtained from the vessels by one or more tubes 6000 after a separation procedure has been completed by centrifugation. Tips 11500 can vary in number depending upon the number of tubes that obtain fluid from the vessels.

In one embodiment, four tips 11500 correspond to four tubes 6000 that are inserted into cluster 3500 containing four vessels 4500. The number of tips 11500 can vary depending upon the number of tubes 6000 and the number of corresponding cavities 2500 in each cluster 3500. The tips communicate with controller 11000 and are movable so that they can dispense fluid into any number of specimen collectors 12000, where the specimen collectors are, e.g., in a 96, 384, 1536 or other standard member sample format. In a preferred embodiment, tips 11500 are mounted on a sliding actuator that is controlled by an electric motor. The tips can be moved by other means such as hydraulic, pneumatic or other suitable movement devices.

Figure 28:
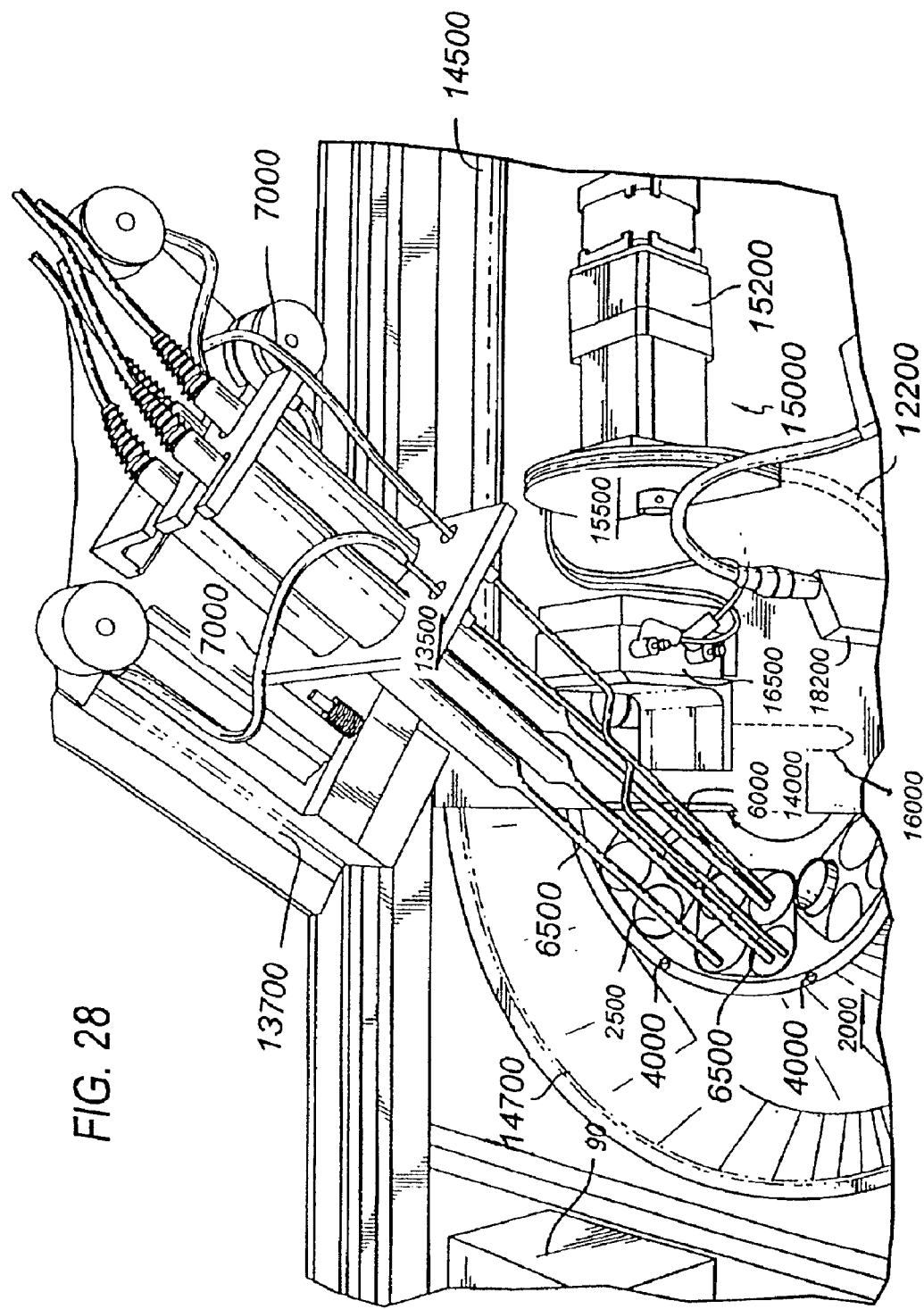
FIG. 28 is a perspective view of some of the components depicted schematically in FIG. 26.

Referring to FIG. 28, one embodiment of the present invention is illustrated. In this embodiment, rotor 2000 having cluster 3500 containing four cavities 2500 is configured to be substantially simultaneously inserted with a group of tubes 6000 and rods 6500 arranged in pairs so that one tube and one rod are inserted into each cavity 2500. In this arrangement, each cavity 2500 of cluster 3500 can be simultaneously inserted with tube 6000 and rod 6500. Transport 13500 holds the four tubes 6000 and four rods 6500, and as discussed above, the tubes are connected to hoses 7000 and the rods comprise a sonication device employing, e.g., a 20 kilohertz transducer. The sonication device re-suspends particles that have been compressed by centrifugation. Other types of re-suspension devices can be employed, such as chemical re-suspenders, pipettors, etc.

Movable transport 13500 is mounted on pneumatic slide 13700 that is actuated by controller 10000 to insert and remove tubes 6000 from cavities 2500. In addition to the movement into and out of the cavities, the transport can also be moved horizontally by an electric motor that communicates with the controller. In this manner, the transport can be moved away from rotor 2000 to permit insertion of vessels 4500 into the rotor and removal of the rotor from the centrifuge.

Figure 29:
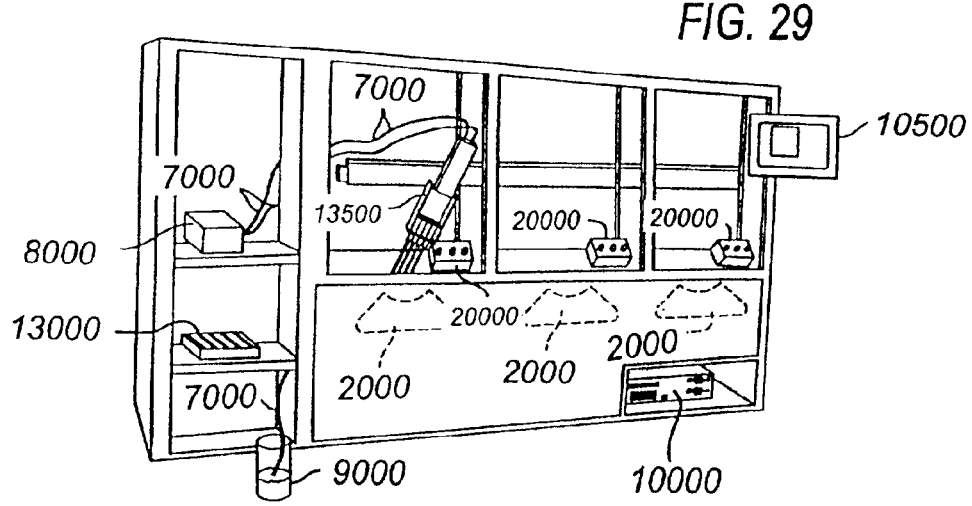
FIG. 29 is an elevation view of one embodiment of an automated centrifuge of the present invention.

Also, as shown in FIG. 29, one embodiment of the present invention employs three rotors 2000, and transport 13500 can be moved into position over each rotor 2000 by controller 10000 directing the movement of the transport. The number of rotors incorporated into an automated centrifuge constructed according to the present invention can vary according to the needs of the laboratory, or research facility. Similarly, the system can be reconfigured so that the rotors move relative to tubes 6000, rather than moving the tubes with transport 13500. Also shown in FIG. 29, are operator interface 10500, fluid pump 8000, and rotor control boxes 20000.

Another preferred embodiment employs multiple transports, such as transport 13500. With multiple transports, each transport can be arranged to simultaneously (or sequentially, if desired) cooperate with different clusters 3500. In such a manner, the same sample treatment function can be performed on more cavities 2500 at the same time, enabling a more high throughput operation. Alternatively, each transport can control a group of tubes 6100 to perform a single function, which minimizes the need for washing or cleaning the tubes between process steps. For example, one group of tubes is optionally used to dispense a buffer, another group to aspirate a first fluid, and a third group to aspirate a second fluid. Since each group of tubes 6100 has only one function, there is no need to wash or clean the tubes between steps.

Again referring to FIG. 28, rotor cover 14000 is slidably positioned over rotor 2000 by actuator 14500. In this embodiment, two actuators each comprise a pneumatic piston that communicate with controller 10000. Other devices can be used to position the rotor cover over, and away from the rotor. The rotor cover has a circumferential seal located on the underside of the rotor cover so that when the rotor cover is positioned over the rotor, the seal engages rotor housing 14700.

In one embodiment the seal is comprised of rubber and can be expanded by the injection of air, thereby causing the seal to mate with rotor housing 14700. In this manner, an air-tight seal can be created between rotor housing 14700 and rotor cover 14000 to increase centrifugation efficiency by minimizing the movement of air generated by the spinning rotor.

2. Functions of the Automated Centrifuge

With reference to FIGS. 28–32, a description of the discrete functions which the automated centrifuge of the present invention can perform is described below.

Illustrated in FIGS. 29 and 32, operator interface 10500 allows a technician to program controller 10000 with a "recipe" that is, a list of instructions that directs the controller to perform specific functions appropriate to a specific test. FIG. 32 illustrates a recipe entry screen. In the illustrated embodiment, up to twenty-five or more separate steps can be performed in one recipe. More or less than 25 steps can comprise a recipe, depending upon the requirements of a specific test. Once specific step 19500 has been chosen by the operator, a corresponding function is chosen from possible operations box 18500.

Once the recipe is finished and all of the steps have been entered by the technician, the recipe can be named and saved in recipe file control box 19000. In this manner, hundreds of discrete recipes can be stored for easy access to quickly program the system, thereby saving valuable technician time.

Generally, a first step is to load vessels 4500, containing a material for centrifugation, into cavities 2500. This can be performed either manually or with the indexer 15000 engaged. Illustrated in FIGS. 28, 30, and 31, indexer 150 comprises wheel 15500 positioned to contact rotor rim 2200. Wheel 15500 is driven by indexer motor 15200 that communicates with controller 10000. An example motor suitable for use as motor 15200, that is commercially available is the silver max motor from QuickSilver Controls, Inc. Many other suitable motors are also commercially available.

The indexer motor and wheel are slidably mounted on rotor cover 14000 by a pneumatically driven slide that communicates with the controller. In manual mode, the controller instructs the pneumatically driven slide to raise the wheel away from the rotor rim, so that the rotor can easily be spun by hand. In this manner, the rotor can be rotated and vessels can be placed into the cavities.

Alternatively, rotor 2000 can be loaded with vessels 4500 by configuring the present invention into "index mode." In index mode, indexer 15000 is lowered by controller 10000 so that wheel 15500 directly contacts rotor rim 2200. To keep rotor 2000 from tilting when the wheel engages the rotor rim, live center 16000 is inserted into rotor post 17000, shown in FIG. 31. The live center is connected to sliding mount 16500, which communicates with the controller. The sliding mount is optionally pneumatically driven, but other devices can be used to raise and lower sliding mount 16500, to disengage or engage live center 16000.

Other devices can also be used to raise and lower indexer 15000 and wheel 15500. When indexer motor 15200 is lowered, with wheel 15500 contacting rotor rim 2200, the controller searches for a first cluster 3500. This is accomplished by two optical sensors 18000 and 18200 that communicate with controller 10000, wherein the sensors are mounted on rotor cover 14000. The optical sensors tell the controller where the rotor is and the indexing motor moves the rotor around. Alternately, this is replaced with an optical encoder on the rotor shaft and the main drive motor moves the rotor as well as spinning it during centrifugation.

One aspect of the invention is simply the specific positioning of the rotor relative to the rotor chamber. That is, prior art centrifugation systems which simply perform centrifugation do not specifically position the rotor.

Figure 30:
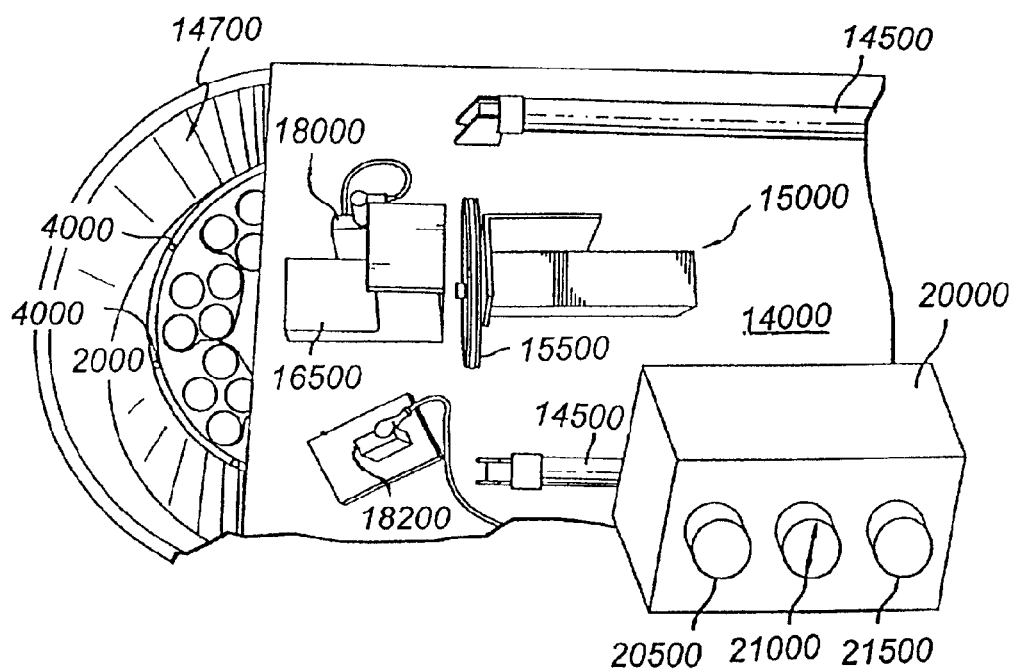
FIG. 30 illustrates the rotor and rotor cover illustrated in FIG. 27 and also illustrates the rotor control box of the present invention.

Referring to FIGS. 27, 29, and 30, reference optical sensor 18000 detects designated first cluster 3500, and rim optical sensor 18200 detects all of the clusters by reading indexes 4000 on rotor rim 2200. The rim optical sensor reads the indexes and controller 10000 then positions the appropriate cluster that corresponds to each index under tubes 6000. In one embodiment, reference optical sensor 18000 detects a reference located on rotor 2000 that indicates the designated first cluster. Once the first cluster is located, the index wheel 5500 rotates the rotor one cluster at a time using information from the rim optical sensor, which reads the indexes located on the rotor rim. In this manner, the first cluster can be determined and each subsequent cluster can be positioned underneath the tubes and rods. Other suitable sensors and methods can be employed to determine the location of each cluster.

As described above, when the system is configured in index mode, rotor 2000 is rotated by wheel 15500 so that an operator can insert vessels 4500 into cavities 2500 without manually turning rotor 2000. Illustrated in FIG. 30, rotor control box 20000 that communicates with controller 10000, controls the movement of the rotor by the above-described system of optical sensors 18000 and 18200, indexer motor 15200 and wheel 15500. The rotor control box comprises a open/close switch 20500, a rotor rotation button 21000, and an emergency stop knob 21500. When in index mode, as described above, the optical sensors, working with the indexer motor and wheel position the rotor over a first cluster. A technician can then load the vessels into the four cavities comprising the first cluster. When finished, the technician presses the rotor rotation button, rotating the rotor in a clockwise direction so that the next cluster is positioned for insertion of vessels.

As illustrated in FIG. 30, the rotor rotation button comprises an up-arrow switch that moves rotor 2000 in a clockwise direction and a down-arrow switch that moves the rotor in a counterclockwise direction. When the technician has completed inserting vessels 4500 into all of the cavities 2500 by rotating the rotor one cluster 3500 at a time, the technician activates the open/close switch 20500 which instructs controller 10000 to slide rotor cover 14000 over rotor 2000. Rotor control box 20000 also includes emergency stop knob 21500 that cuts power to all the electrically driven devices on the present invention in case of an emergency situation.

Another function of the present invention is the incubation of components or other materials contained in vessels

4500 that are located in cavities 2500. For example, protein isolation and other laboratory procedures can require the incubation of the proteins. Incubation is accomplished by positioning rotor cover 14000 over rotor 2000, inflating the rotor seal, and thereby sealing rotor 2000 from the environment. A conventional centrifuge cooling system communicates with rotor 2000 and temperatures can be accurately maintained in a range between minus 10 degrees centigrade to above 50 degrees centigrade, depending on the application. A centrifuge cooling and heating system can be employed with the automated centrifuge system.

Yet another function of the present invention is the centrifugation of suspended particles located in vessels 4500 that have been placed in the cavities 2500. This is accomplished by sealing the rotor 2000 from the environment by placing the rotor cover 14000 over the rotor 20 inflating the rotor seal and spinning the centrifuge rotor 2000 thereby separating the suspended particles by their densities.

Still another function performed by automated centrifuge system 1000 is the dispensing of buffers, rinses or other fluids into vessels 4500 that have been placed in cavities 2500. Illustrated in FIGS. 26 and 28, tubes 6000 are inserted into vessels 4500 by transport 13500 that is directed by controller 10000. Hose 7000 connected to tube 6000 carries fluid from pump 8000 which obtains the fluid from fluid source 8500. Different fluids, such as buffers, washes, or cleansers can be selected from the fluid source by the controller and thereby be dispensed by the pump through the hoses and into the tube and finally into the vessels. In this manner, various fluids can be dispensed into the vessels as part of a bio-molecule (e.g., protein) isolation or other centrifugation procedure. In a preferred embodiment, shown in FIG. 28, fluid can be dispensed into four vessels substantially simultaneously by the four tubes that are positioned over each cavity in a cluster, e.g., containing four cavities 2500 in the depicted embodiment. One, two, three, four or more than four vessels 4500 can receive fluid from the tubes, depending upon the number of tubes 6000 and the arrangement of cavities 2500 in rotor 2000.

Aspiration of fluids from vessels 4500 can be performed by the present invention in a manner similar to the dispensing function described above. Tube 6000 is inserted into vessel 4500 that is located in cavity 2500, and pump 8000 is activated to create a vacuum, thereby sucking out the fluid contained in vessel 4500. The removed fluid travels through tube 6000 into hose 7000 through pump 8000 and can either be sent to specimen/fraction collector 11000 or to waste dump 9000, depending upon the instructions sent by controller 10000. For example, after centrifugation, denser material has been forced to the bottom of vessel 4500 and the less-dense fluid is aspirated by tube 6000 into waste dump 9000. Alternatively, a soluble protein maybe suspended in vessel 4500 and the soluble protein can be aspirated from vessel 4500 by tube 6000 and sent to fraction collector 11000. The fraction collector is optionally refrigerated, e.g., to prevent sample degradation. At fraction collector 11000, the soluble protein fluid is deposited into specimen collectors 12000. As discussed above, and illustrated in FIG. 28, aspiration of up to four vessels 4500 can be conducted substantially simultaneously by the present invention, drastically reducing the time required for laboratory experiments. The number of vessels 4500 that can be aspirated, however, can be varied depending upon the arrangement of tubes 6000, and the instructions sent by controller 10000.

An additional function performed by the present invention is the sonication of materials located in vessel 4500. When one or more vessels are chosen for sonication, sonication rod 6500 is inserted into a vessel and controller 10000 activates the sonicator. During sonication, the rod is vibrated at a frequency of, e.g., about 20 kilohertz. Other frequencies can be employed for sonication. This creates sound waves which break apart the material located in the vessel. For example, once an initial centrifugation step has been performed, a collection of cells is located near the bottom of the vessel. The sonication rod is inserted into the vessel and the cells are sonicated, which breaks the cells apart, thereby exposing proteins which are later isolated.

In a preferred embodiment, as illustrated in FIG. 28, sonication rod 6500 is positioned adjacent to an aspirate/dispense tube 6000. In this manner, sonication can be performed immediately after, before or during the dispensing or aspiration of fluids from vessel 4500.

A sample recipe will now be described, illustrating one example automated isolation process which can be performed by the present invention. Vessels 4500 containing suspended material are placed in cavities 2500 in rotor 2000. Controller 10000 moves rotor cover 14000 over centrifuge rotor 2000 and rotor 2000 is spun by rotor motor 2700. Rotor cover 14000 is slid back revealing vessels 4500. Transport 13500 moves tubes 6000 and rods 6500 into position over a first cluster 3500 found by optical sensors 18000 and 18200. Four tubes 6000 are substantially simultaneously inserted into four vessels 4500 and fluid located therein is aspirated into waste dump 9000. The tubes are removed by the transport, indexing motor 15200 rotates index wheel 15500 to a next cluster 3500 and this procedure is repeated until all of the fluid in all of the vessels is removed.

The vessels are then removed by a technician and frozen, which breaks up many of the cells located in the pellet, which is formed in the bottom of the vessel as a result of the centrifugation. After freezing, the vessels are again loaded into cavities 2500 in rotor 2000. Controller 10000 instructs transport 13500 to position tubes 6000 into vessels 4500 and a selected buffer is dispensed into each vessel. Also, sonication rod 6500 is simultaneously inserted with tube 6000 and the pellet is sonicated, thereby disbursing the components of the pellet into the buffer fluid. This fluid dispensing and sonication procedure is performed on all vessels 4500 that are contained in rotor 2000.

Rotor cover 14000 is positioned over rotor 2000 and rotor and vessels 4500 are incubated. Rotor cover 14000 is then slid away from rotor 2000 and sonication rods 6500 are inserted into vessels 4500 and activated to resuspend the cells. The sonication rods are removed by transport 13500, the rotor cover is positioned over the rotor, and the rotor is then spun to centrifuge the materials contained in the vessels.

Now, tubes 6000 are inserted into vessels 4500 and the fluid is aspirated out into fraction collector 11000. The material aspirated may contain soluble proteins as part of a protein isolation procedure. After depositing fluid into fraction collector 11000, the hoses 7000 can be rinsed by flushing fluid from the fluid source 8500 through hoses 7000 and through tubes 6000 into waste dump 9000 located adjacent to centrifuge rotor 2000. After the flushing procedure, controller 10000 activates pump 8000 to aspirate the rinsing solution into the waste dump 9000. Tubes 6000 are inserted into the vessels and a selected buffer from the fluid source is inserted into the vessels. Sonication rod 6500 is then activated, sonicating the recently dispensed buffer and the materials still remaining in the vessels.

Tube 6000 and rod 6500 are removed from vessel 4500 and rotor 2000 is spun, thereby centrifuging sample in vessel

4500. The tube is again inserted into the vessel and supernatant fluid is aspirated into waste dump 9000, using pump 8000.

This process of dispensing buffer, sonicating, centrifuging and aspirating waste fluid can be repeated as many times as necessary to further purify remaining proteins left after centrifugation. In one recipe, remaining insoluble proteins located in vessel 4500 can be dissolved by instructing tube 6000 to dispense a buffer designed to place the insoluble proteins into solution, such as GB buffer, described above. Again, these materials are sonicated either during dispensing of the buffer or shortly thereafter. They are also centrifuged and supernatant fluid is aspirated by tube 6000. The aspirated fluid is deposited into fraction collector 11000 and into specimen collectors 12000. The order of dispensing fluid, sonicating, incubating, aspirating can be changed or varied depending upon the requirements by the user.

3. An Alternative Automated Centrifuge System

Referring to FIG. 33, an alternative embodiment automated centrifuge system 30000 is shown. In this embodiment, the automated centrifuge system 30000 comprises large rotor 30500 containing a plurality of clusters 3500 of cavities or holes 2500 arranged to cooperate with aspirate tubes 6200, dispense tubes 6400 and rods 6500, shown in FIG. 34. Tubes 6200 and 6400 and rods 6500 are mounted on moveable head 31000 that rides on track 31500. Moveable head 31000 can position tubes 6200 and 6400 and rods 6500 into or adjacent to cavities 2500. When inserted into cavities 2500, aspirate tubes 6200 can aspirate fluids from one cluster 3500 of cavities 2500 while rods 6500 sonicate fluid in second cluster 3500 of cavities 2500. Dispense tubes 6400 are arranged to dispense fluid into the second cluster of cavities. In a preferred embodiment, the aspiration and sonication operations can occur substantially simultaneously. The aspiration, sonication and dispense operations can be performed substantially simultaneously, or in any order necessary to efficiently process fluid samples. In this manner, the efficient automated processing of a large number of discrete fluid samples can be performed without substantial human intervention.

Automated centrifuge system 30000 illustrated in FIG. 33 eliminates many components of the above-described automated centrifuge system 1000, resulting in the faster processing of fluids or substances deposited in cavities 2500. While employing many of the concepts and components of automated centrifuge system 1000, described in detail above, automated centrifuge 30000 eliminates many components, resulting in a machine that processes fluid samples faster, yet costs less to construct and operate. In particular, the indexing system for determining the position of rotor 2000 and rotor control box 20000 is removed from the embodiment illustrated in FIG. 33. Automated centrifuge system 30000 employs rotor position sensor 34500. This replaces several components, including: index 4000, indexer 15000, index motor 15200, index wheel 15500, live center 16000, sliding mount 16500, reference optical sensor 18000 and rim optical sensor 18200. In this embodiment, rotor motor 2700 is controlled by controller 10000 to perform both centrifugation and rotor positioning.

In a preferred embodiment, the rotor position sensor 34500 is a rotary optical encoder. Other types of devices used for measuring the rotation and position of rotor shaft 34000 can be employed, such as inductive angle measuring devices, resolvers and other similar apparatus. Rotor position sensor 34500 is positioned on rotor shaft 34000 and communicates with controller 10000 which is operated through operator interface 10500. Certain available controllers or controller components can be used to direct rotor positioning and/or centrifugation by rotor motor 2700, e.g., the 2400 modular performance AC drive available, e.g., from UNICO, Inc. (Franksville, Wis.). As discussed above, the operator interface allows a technician to program the controller with a "recipe" which is a list of instructions that tells the controller to perform specific functions appropriate to a specific task. For example, a component such as a protein that is suspended in a fluid may need to be isolated through a centrifugation process. The technician programs the appropriate "recipe" into the controller and then proceeds to load vessels 4500 into large rotor 30500.

Referring to FIG. 33, once a recipe has been entered through operator interface 10500 and into controller 10000, the controller determines the position of rotor 30500 through rotor position sensor 34500. The technician inserts vessels 45 into cavities 2500 and then places both hands on the switch 32000. The rotor is then rotated, presenting a new cluster 3500 of cavities 2500 for loading. Switch 32000 provides an important safety feature by forcing the technician to place his hands on the switch before the rotor is rotated. This avoids any possible injury to the technician, by keeping his hands well away from the rotating rotor. In a preferred embodiment, switch 32000 comprises one or more touch buttons. Touch buttons register an operators touch, converting that touch into an electrical output that signals the controller to rotate the rotor. Other types of safety switches such as capacitive and photoelectric sensors and other suitable devices can be employed in place of the switch. Ordinarily, there are 2 touch buttons, i.e., one for each of an operator's hands. Thus, an operator places 2 hands on the touch buttons, ensuring that the operators hands are out of any danger from the rotor before engaging the rotor.

After placement of vessels 4500 into cavities 2500, rotor cover 14000 is positioned over rotor 30500. Rotor 30500 is then spun, separating the different components through a centrifugation process. When the centrifugation process is complete, rotor 30500 is stopped. Controller 10000 then instructs rotor cover 14000 to slide away, revealing rotor 30500.

Figure 35:
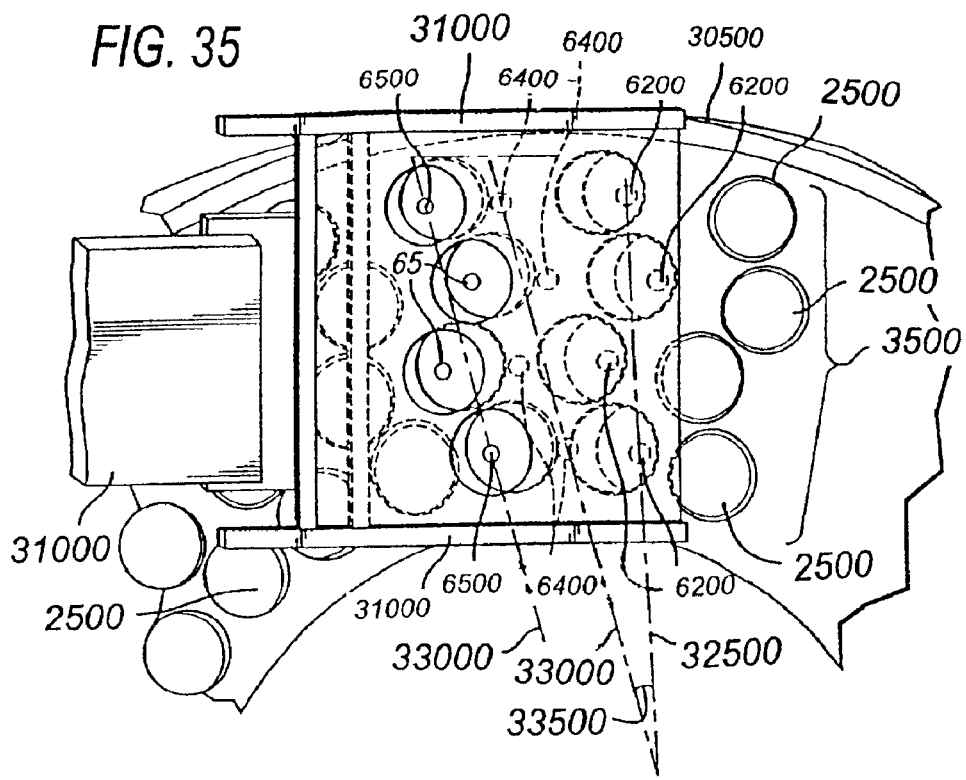
FIG. 35 is a plan view of the rotor illustrated in FIG. 34.

Referring now to FIGS. 34 and 35, the insertion of the aspirate tubes 6200, dispense tubes 6400, and rods 6500 into cavities 2500 will now be described. In one preferred embodiment, rotor 30500 contains ninety-six cavities 2500 arranged in twenty-four clusters 3500 of four cavities 2500. As shown in FIG. 35, the cavities are arranged substantially radially on rotor 30500. As discussed above, the longitudinal axes of all of the cavities of each cluster are substantially parallel, thereby permitting the substantially simultaneous insertion of one or more of the rods, aspirate tubes and/or dispense tubes.

Referring to FIG. 35, one arrangement of rods 6500 and aspirate tubes 6200 and dispense tubes 6400 is illustrated. Four aspirate tubes, four dispense tubes and four rods are mounted on movable head 31000. In a preferred embodiment, the dispense tubes and rods have parallel tube axes 33000. The aspirate tubes are arranged on a tube axis 33000 that is angled 33500 relative to the dispense tube axis. The angle allows the aspirate tubes and rods to be substantially simultaneously inserted into two adjacent clusters 3500. This allows the aspiration of fluids from one cluster 3500 of cavities 2500 and the simultaneous sonication of an adjacent cluster of cavities. Shown in FIG. 34, the dispense tubes are significantly shorter than the aspirate tubes 6200 and can be arranged to dispense fluid into the same cavities that the rods are positioned in. Other arrangements of aspirate tubes and dispense tubes and cavities can be constructed, such as positioning tubes 6200 and rods 6500 in a splayed arrangement so that three or more clusters 3500 of cavities 2500 can be substantially simultaneously serviced.

Figure 36:
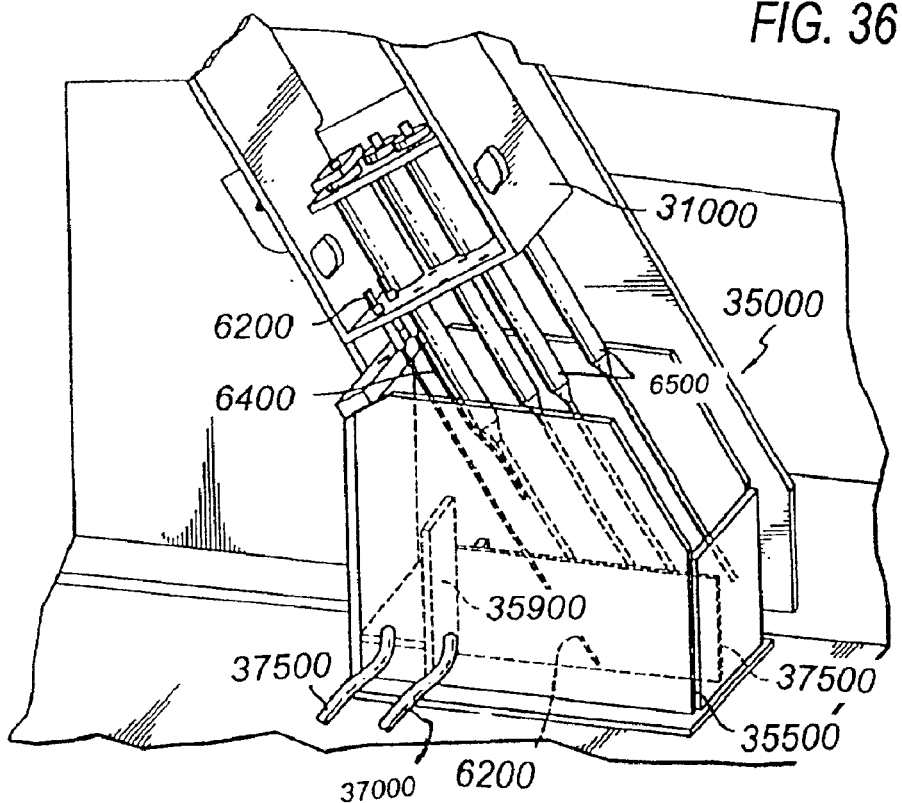
FIG. 36 is a perspective view of a transport and waste trough illustrated in FIG. 33.
Figure 37:
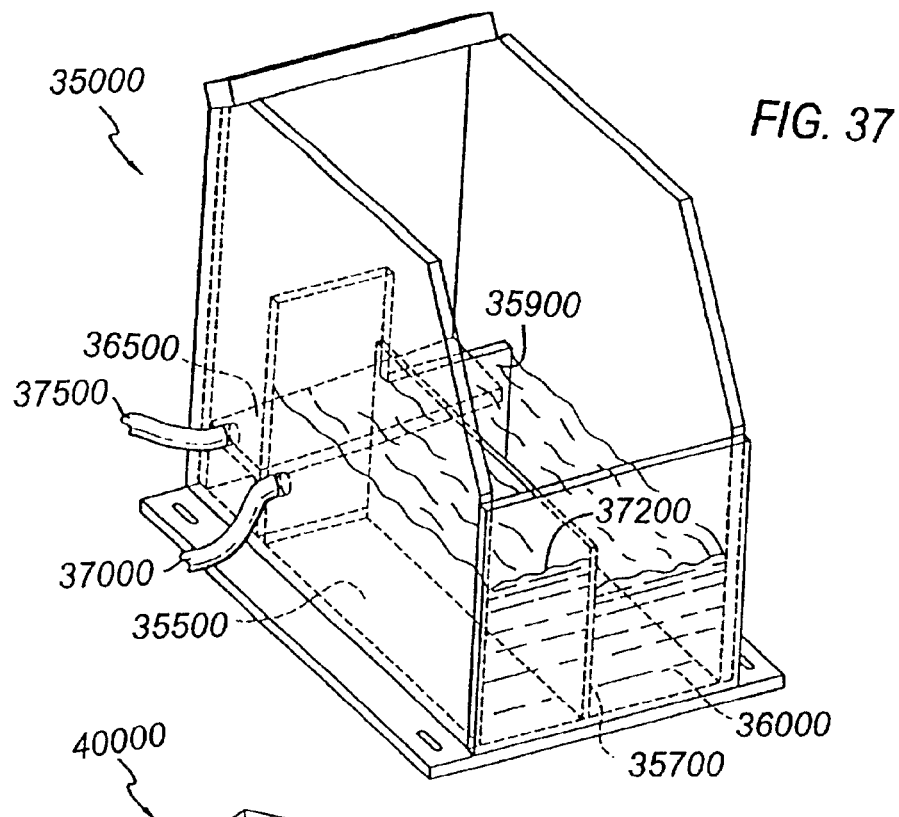
FIG. 37 is a perspective view of the waste trough illustrated in FIG. 36.

Referring to FIGS. 36 and 37, waste/rinse container 35000 is illustrated. After tubes 6200 and 6400 and rods 6500 have performed their functions in cavities 2500, rotor cover 14000 is slid over rotor 30500. This positions the waste/rinse container under movable head 31000. The moveable head is then transported down track 31500 and tubes 6200 and 6400 and rods 6500 are positioned in the waste/rinse container. Aspirate tubes 6200 are inserted into tube bin 35500 with rods 6500 inserted into rod bin 36000. Dispense tube 6400 does not need rinsing, as it does not need to contact fluids or other substances in the cavities. Fluid source 8500 delivers fluid through rinse fluid input 3700 and into tube bin 35500. Rinse fluid 37000 can be dionized water, alcohol, detergent, or any other suitable rinsing fluid. Rinse fluid 37000 washes aspirate tube 6200 and, if necessary, aspirate tubes 6200 can aspirate rinse fluid 37000 and dump it into waste dump 9000. The rinse fluid fills the tube bin and then overflows into rod bin 36000 where it rinses sonication rod 6500. Dispense tube 6400 can dispense fluids into rinse fluid 37000, which then runs down run-off ramp 36500 to rinse fluid exit 37500 and to waist dump 9000 through tubes or other means that are not illustrated.

Figure 38:
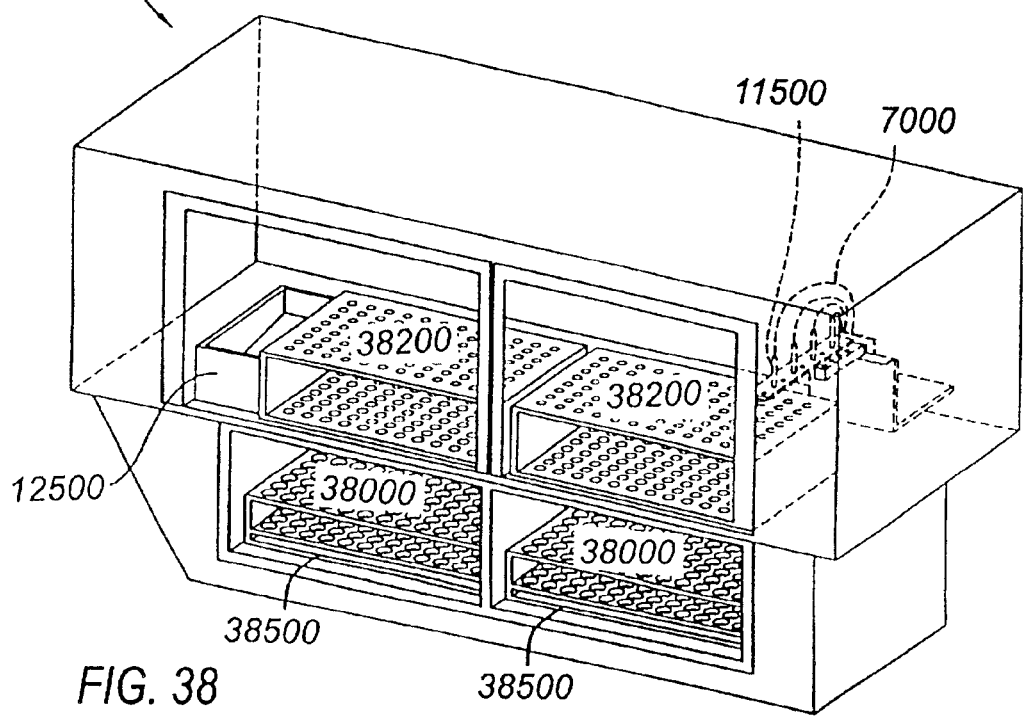
FIG. 38 is a perspective view of a sample/ fraction collector illustrated in FIG. 33.

Referring to FIG. 38, fraction collector 40000 is illustrated. Fraction collector 40000 is structured to collect sample components that have been isolated during a centrifugation process. Tips 11500, that are connected to hoses 7000, deposit isolated material obtained from cavities 2500 by aspirate tubes 6200 into filter bed 38200, preferably arranged in a standard ninety-six, three hundred eighty four, or one thousand five hundred thirty six member sample format. The fraction collector optionally comprises one or more additional tips or sets of tips that dispense fluid from sources other than the cavities. Hoses 7000 communicate with aspirate tubes 6200 as described above. In a preferred embodiment, filter bed 38200 comprises a plurality of vessels, each comprising a filter structured to remove particles that have not been separated during the centrifugation process. For example, nitrocellulose filters or Whatman filters or sepharose resin filters or other suitable filters can be employed.

After passing through filter bed 38200, the fluid then drops down onto resin bed 38000, which preferably is arranged in standard format such as a ninety-six, three hundred eighty four, or one thousand five hundred thirty six member sample format. Resin bed 38000 is structured to catch the components that have been isolated during the centrifugation process. For example, proteins that have passed through the filter bed 38200 are now caught in resin bed 38000. In a preferred embodiment, a nickel chelate resin is employed, but other types of resins, such as ion-exchange resins and hydrophobic interaction resins, can be employed. Located beneath resin bed 38000 is catch tray 38500 that catches any remaining fluids and deposits them in waste dump 9000.

Figure 39:
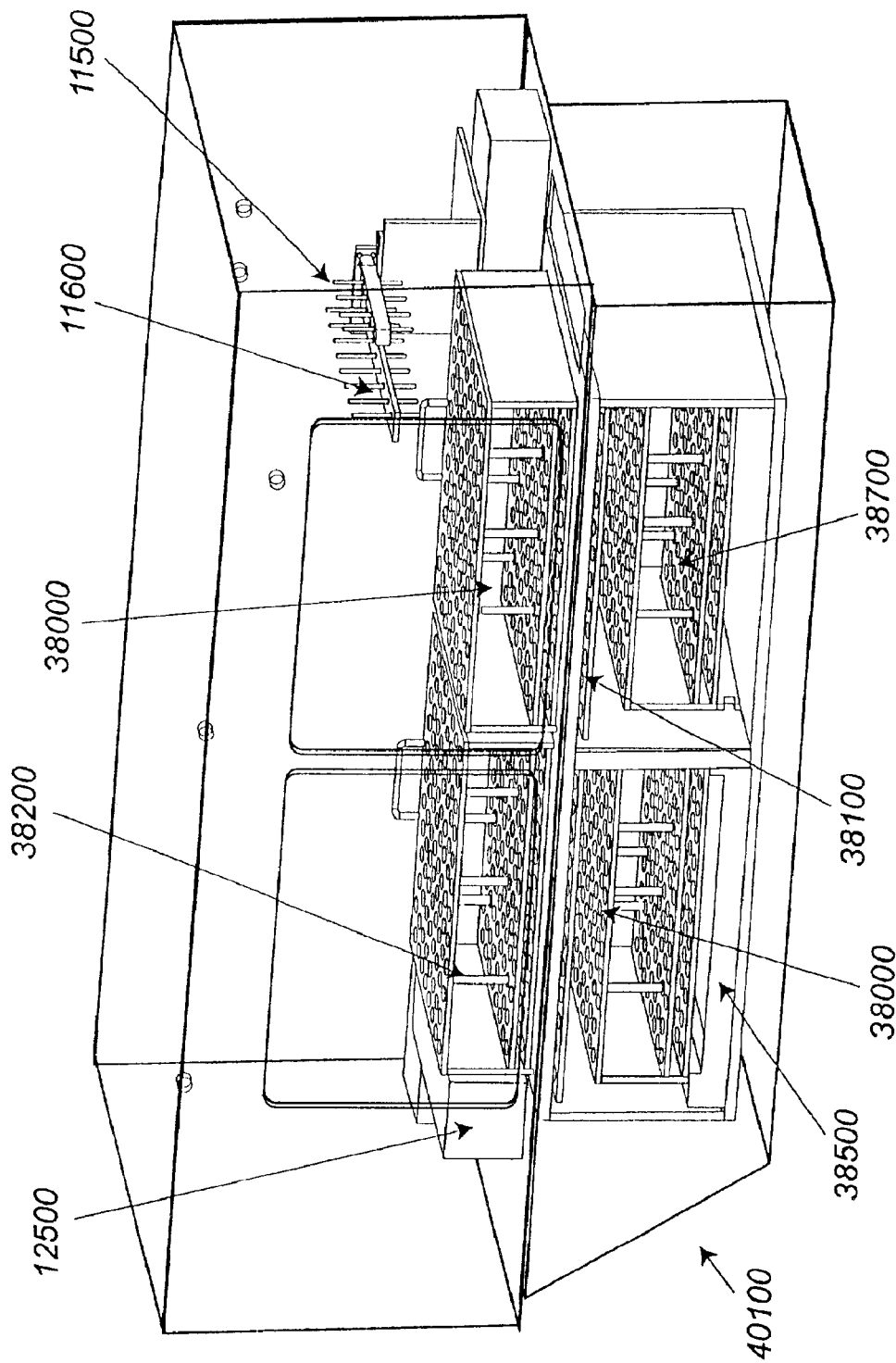
FIG. 39 is a perspective view of an alternate sample/ fraction collector illustrated in FIG. 33.

FIG. 39 illustrates an alternate fraction collector embodiment which omits the need for a filter tray (right side of drawing). Fraction collector 40100 is illustrated, schematically showing two different configurations of collector component options on the left and right side of the drawing. The left side of the drawing is configured as in FIG. 38 for comparative purposes. The right side represents a different collector configuration. In practice, either the left side configuration, or the right side configuration, or both, can be used for any given collector. As illustrated on the right side of the drawing, fraction collector 40100 is structured to collect sample components that have been isolated during a centrifugation process. Tips 11500 that are connected to hoses 7000 deposit isolated material obtained from cavities 2500 by aspirate tubes 6200 into tips 11500 which dispense material into resin bed 38000 comprising resin bed rack 37900 and resin bed columns 37800. Resin bed 38000 is depicted schematically. As shown, only a few resin columns are placed in the bed. However, in use, resin bed 38000 can comprise resin columns 37800, in any or all of the holes in rack 37900. In one embodiment, the columns comprise a nickel chelate resin, but it will be appreciated that any other appropriate purification material can be substituted in the column, depending on the material to be purified. Additional tips 11600 are connected to buffer or other fluid sources and dispense fluids into resin bed 38400 to provide for washing or rinsing of materials on the columns, and/or separation of the materials from the columns (e.g., by applying a cleavage reagent). For example, when dispensing washing fluid, waste collection tray 38100 located under resin bed 38000 collects waste from the resin bed. The waste collection tray is coupled to waste dump 19000 and provides for delivery of waste from the resin bed to the waste dump. When tips 11600 dispense a material which provides for separation of desired components from the resin bed, waste collection tray 38100 is placed in a non-collecting position and fluid comprising the sample of interest (e.g., a purified protein) drops into collection rack 38700. Collection tube rack 38700 is located beneath the waste collection tray and collects sample components such as purified protein components or the like, e.g., in collection tubes or microtiter trays placed in the rack. Any or all of these beds or trays can be arranged in a standard format, e.g., in a 96, 384, or 1536 well arrangement to provide for simplified processing and collection of purified materials.

Figure 40:
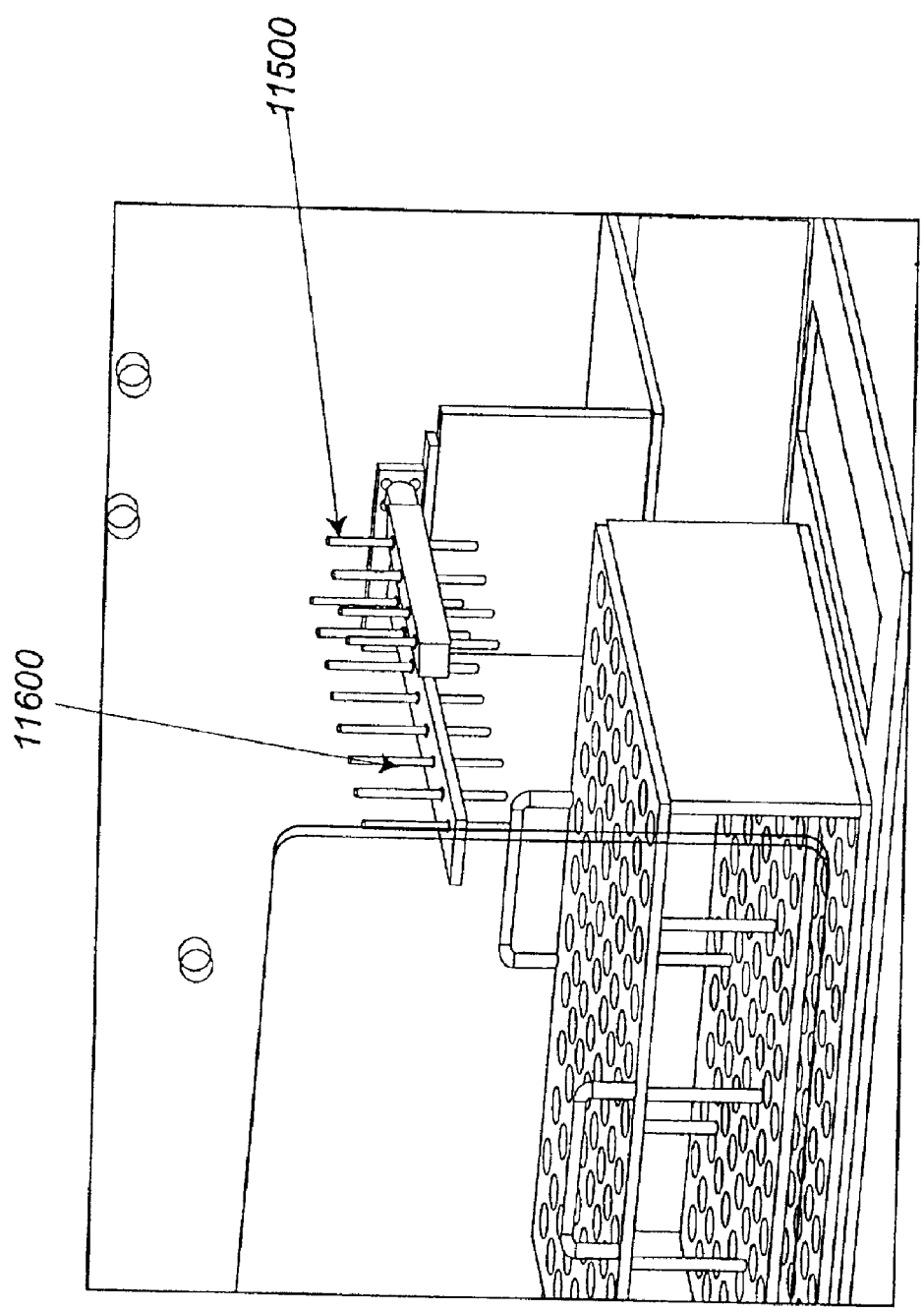
FIG. 40 is a perspective view of an arrangement of tips which operate in the sample/fraction collectors of FIGS. 38 and 39.

FIG. 40 provides details on the arrangement of tips 11500 and 11600 in one example embodiment which can apply to any of the sample/fraction collector embodiments noted above. Tips 11500 are fluidly coupled to sample processing elements, while tips 11600 are coupled to fluid sources that provide wash, rinse, cleavage or other solutions of interest to the collector.

Also shown in FIG. 33 is controller 10000. As discussed above, the controller optionally comprises a general purpose computing device that controls a function of automated centrifuge 30000. In one embodiment, the automated centrifuge employs a controller that comprises two programmable logic controllers (PLCs) with one PLC operating operator interface 10500 and directing the second PLC to perform the variety of functions of the automated centrifuge 30000. In an alternate similar embodiment, one PLC controls the fraction collection functions for the fraction collector noted above while another controls the user interface, the main rotor functions, and, optionally, controls the PLC that controls the fraction collector functions. The number, function and arrangement of PLC can vary, depending on the system components and the operations that the overall system performs.

Once sample fractions are collected in, e.g., microtiter plates, collection tubes, or the like, the samples are then typically subjected to additional downstream processing, such as crystallization and structural analysis, which are described further below.

IV. Crystallization and Analysis

One application of the various methods and devices of the present invention is their use in the process of going from protein expression to protein structure determination via protein crystallization. More specifically, the protein fermentation, processing and purification methods and devices of the present invention may be used in combination with known protein purification and submicroliter crystallization processes to determine crystallization conditions for proteins. Once crystallized, protein structures can be determined by standard x-ray crystallography techniques from the protein crystals produced.

One bottleneck in the process of producing protein crystals for structure determination is the production of sufficient quantities of protein to use in crystallization experiments. The amount of protein needed to perform such crystallization experiments was recently reduced by reducing the amount of protein used per crystallization experiment. For example, U.S. Pat. No. 6,296,673 entitled "Methods and Apparatus for Performing Array Microcrystallizations" describes performing protein crystallizations where a protein solution volume of less than 1 microliter is used per crystallization experiment. For example, 1000, 750, 500, 250, 100, 50 nanoliters or less of protein solution may be used per crystallization experiment.

The protein solution used in submicroliter crystallization experiments commonly has between about 5–20 mg/mL. As a result, for example, 200 microliters of a 10 mg/mL protein solution is generally sufficient to perform over 1000 submicroliter crystalliation experiments, which is typically enough experiments to determine suitable crystallization conditions for a protein.

With the ability to crystallize proteins in submicroliter volumes, the amount of a given protein that is needed to perform crystallization experiments to determine crystallization conditions may be 5 mg, 4 mg, 3 mg, 2 mg, 1 mg, 0.5 mg or less.

Despite reducing the amount of purified protein needed to perform crystallization experiments, a need still exists for technology that reduces the amount of labor required to purify proteins. For example, it is currently reasonable to estimate a 10% yield in going from expressed protein in a fermentation to purified protein for use in crystallization experiments. Accordingly, a need still exists for producing 5 mg, 10 mg, 20 mg, 30 mg, 40 mg, 50 mg, or more of a protein via fermentation and then to purify that expressed protein. This need is magnified as one looks to increase the number of different proteins one wishes to crystallize, and thus the number of different proteins for which a source of purified protein is needed, albiet in a smaller quantity due to submicroliter crystallizations.

The various methods and devices of the present invention address this problem by making it less labor intensive to ferment proteins and perform one or more of the protein isolation and purification steps (e.g, centrifugation, cell lysis, pellet and supernatant isolation) in an at least partially parallel and semiautomated manner.

Accordingly, the present invention further relates to methods that comprise fermenting a protein to be crystallized in 2, 3, 4, 5, 10, 20, 40 or more separate fermentation vessels in a same fermentation apparatus; and purifyng the protein from the fermentations; where the amount of protein purified is sufficient to perform crystallization experiments for the protein. The methods may optionally further comprise performing the crystallization experiments as well as obtaining a protein crystal and optionally determining the structure of the protein from the crystal.

In one embodiment, the method is for producing purified protein and comprises: performing in a same fermentation apparatus 2, 3, 4, 5, 10, 20, 40 or more different fermentations in separate fermentation vessels, each fermentation comprising cells expressing a protein to be purified and has a fermentation volume of 500, 250, 100 mL or less; and purifying the expressed protein from the different fermentations. Each of the separate fermentation vessels may be sized to have relatively small volumes (e.g., 500 mL, 250 mL, 100 mL or less) so they can house relatively small fermentation volumes (e.g., between 25 mL and 500 mL, between 25 mL and 250 mL, or between 25 mL and 100 mL).

Because of the relatively small fermentation volumes, the fermentations can be performed using the fermentation system of the present invention. For example, the different fermentations vessels can be held in a same carrier which may optionally be portable. The separate fermentations can also be performed where each vessel is coupled to a common gas distribution arrangement.

In order to support later protein purification and crystallization steps, it is advantageous for the different fermentations to produce 50, 100, 200 mg/liter or more of the proteins to be purified.

Different expression systems may be used including and $E\ coli$ and baculovirus. $E\ coli$ is easy to use as an expression system. However, eukaryotic proteins are sometimes not expressed solubly and active in prokaryotic systems such as $E\ coli$.

Baculovirus has been found to be useful for expressing eukaryotic proteins. However, because the protein being expressed is typically more heterogeneous in the system, it can be more difficult to purify. Baculovirus is also a relatively expensive expression system to use. Baculovirus cultures typically produce in the neighborhood of 4–5 mg/L. As a result, assuming 4 mg/L expression, one needs a 5 liter fermentation to obtain 20 mg of expressed protein to then yield 2 mg of purified protein. As can be seen, in order to use baculovirus expression system, it is desirable to have a labor efficient process for fermenting and isolating the expressed protein.

Because of the relatively small fermentation volumes, purifying the different proteins from the fermentations can optionally be performed where at least part of the purification process is performed in the same fermentation vessels. For example, the fermentation volumes can be transferred to a centrifuge head by simply transferring the same fermentation vessels to the centrifuge head. The fermentations can then be centrifuged in parallel as part of the protein isolation process. Further processing steps such as cell lysis and cell pellet and supernatant isolations can also be performed in the same fermentation vessels. Using the devices and processes described herein, operations such as cell lysis, cell pellet isolation and supernatant isolation can also be performed in parallel.

Because the amount of protein that can be purified from the different small volume fermentations is sufficient to perform submicroliter protein crystallization experiments, in one embodiment, a method is provided for producing a purified protein, the method comprising: performing in a same fermentation apparatus 2 or more different fermentations in separate fermentation vessels and each fermentation comprises cells expressing a protein to be purified; purifying the protein from the different fermentations; and determining crystallization conditions for the purified protein by submicroliter crystallization experiments.

An advantage of combining submicroliter crystallization technology with the methods and devices of the present invention is that less fermentation volume per protein is needed to yield sufficient purified protein to determine crystallization conditions for the protein and obtain crystals of the protein. It should be appreciated that the methods and devices of the present invention, in combination with performing submicroliter crystallization experiments, make it possible to take cells expressing a protein to be crystallized, and in a substantially parallel manner, go from fermenting the cells to isolating, purifying and crystallizing the expressed protein. Thus, the reduced amount of purified protein needed to determine crystallization conditions made possible by submicroliter crystallization, in combination with the highly parallel and semiautomated process of going from fermentation to purified protein according to the present invention, a parallel, high throughput process of going from protein expression to protein crystal and to crystal structure is made feasible.

V. Robotics

Any of a variety of traditional robotics can be employed to move samples, microwell plates or other sample vessels (e.g., fermentation sample vessels, centrifuge tubes, etc.), fermentation apparatus, centrifuge rotors, and/or other objects or components of the present invention, e.g., between work stations and to move sample processing components proximal to or inserted into sample receiving elements. Such robotics can include robotic armatures, grasping mechanisms or components, conveyor systems (e.g., conveyor belts) or the like. Typically, robotic components are coupled to a control system that directs sample/sample vessel movement between stations, and/or sample/vessel tracking within the system, and/or sample processing component movement to the rotor, rotor positioning, and/or the like.

In particular, the present invention provides gripper apparatus, grasping mechanisms, and related methods for accurately grasping and manipulating objects with higher throughput than preexisting technologies. In certain embodiments, for example, grasping mechanisms are resiliently coupled to other gripper apparatus components. In other embodiments, grasping mechanism arms include support surfaces and height adjusting surfaces to determine x-axis and z-axis positions of objects being grasped. As used herein, the "x-axis" refers to an axis in a three-dimensional rectangular coordinate system that is substantially parallel to a horizontal plane and approximately perpendicular to both the y- and z-axes. Further, the "z-axis" refers to an axis in a three-dimensional rectangular coordinate system that is substantially parallel to a vertical plane and approximately perpendicular to both the x- and y-axes. In certain other embodiments of the invention, grasping mechanism arms include pivot members that align with objects as they are grasped. In some of these embodiments, pivot members include the support surfaces and height adjusting surfaces. In other embodiments, the arms of grasping mechanisms include stops that determine y-axis positions of objects that are grasped. As used herein, the "y-axis" refers to an axis in a three-dimensional rectangular coordinate system that is substantially parallel to a horizontal plane and approximately perpendicular to both the x- and z-axes. Essentially any combination of these and other embodiments described herein is optionally utilized together.

Figure 41:
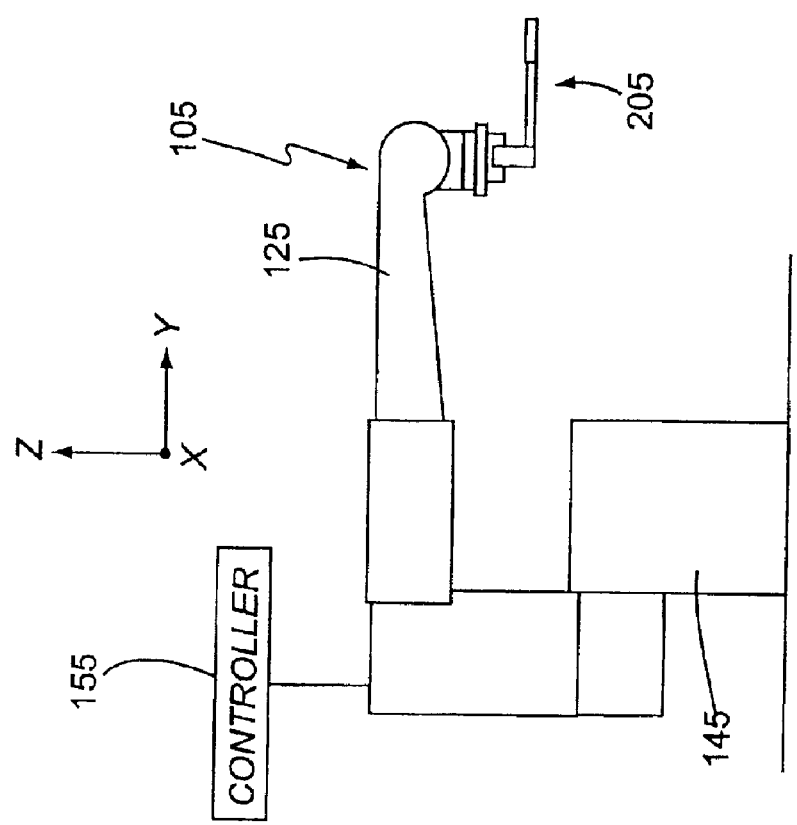
FIG. 41 schematically depicts one embodiment of a gripper apparatus from a side elevational view.

FIG. 41 schematically depicts one embodiment of gripper apparatus 105 from a side elevational view. Robotic gripper apparatus 105 is an automated robotic device, e.g., for accurately and securely grasping, moving, manipulating and/or positioning objects. The design of robotic gripper apparatus 105 is optionally varied to accommodate different types of objects. For example, robotic gripper apparatus 105 is optionally manufactured to grasp sample plates (e.g., microwell plates or the like). Other exemplary objects include, e.g., fermentation sample vessels, fermentation apparatus, centrifuge rotors, etc.

In the embodiment illustrated in FIG. 41, robotic gripper apparatus 105 includes grasping mechanism 205 movably connected to boom 125, which is movable relative to base 145. Controller 155, which optionally includes a general purpose computing device, controls the movements of, e.g., grasping mechanism 205 and boom 125 in a work perimeter that includes one or more stations that can receive and support selected objects. Controllers are described further below. Additional details relating to robotic gripping devices are provided in, e.g., Ser. No. PCT/US02/06096 entitled "GRIPPING MECHANISMS, APPARATUS, AND METHODS," which was filed Feb. 26, 2002 by Downs et al., and U.S. Pat. No. 5,871,248, entitled "ROBOT GRIPPER," which issued Feb. 16, 1999 to Okogbaa et al. and U.S. Pat. No. 5,945,798, entitled "SYSTEM FOR DETERMINING PART PRESENCE AND GRIP PRESSURE FOR A ROBOTIC GRIPPING DEVICE," which issued Aug. 31, 1999 to Stagnitto et al., which are incorporated by reference.

The controllers of the present invention typically include at least one computer (or other information appliance) operably connected to or included within various apparatus or system components (e.g., grasping mechanisms, booms, etc.). The computer typically includes system software or logic instructions that direct, e.g., the movement of robotic booms, the movement of grasping mechanism arms, and/or the movement of other gripper apparatus components. Additionally, a gripper apparatus is optionally coupled to an appropriately programmed processor or computer which functions to instruct the operation of device instrumentation or components in accordance with preprogrammed or user input instructions, receive data and information from these instruments, and interpret, manipulate and report this information to the user. As such, the computer is typically appropriately coupled to one or more of these instruments (e.g., including an analog to digital or digital to analog converter as needed).

In certain embodiments, Microsoft WINDOWS™ software written using instrument control language (ICL) scripts is adapted for use in the gripper apparatus and systems of the invention. Optionally, standard desktop applications such as word processing software (e.g., Microsoft Word™ or Corel WordPerfect™) and database software (e.g., spreadsheet software such as Microsoft Excel™, Corel Quattro Pro™, or database programs such as Microsoft Access™ or Paradox™) can be adapted to the present invention by inputting user-defined instructions, such as defining work piece locations, preset forces for breakaways, or the like. For example, the systems optionally include the foregoing software having the appropriate, e.g., work piece positional information used in conjunction with a user interface (e.g., a GUI in a standard operating system such as a Windows, Macintosh or LINUX system) to manipulate such information.

The computer can be, e.g., a PC (Intel x86 or Pentium chip-compatible DOS™, OS2™, WIDOWS™, WINDOWS NT™, WINDOWS95™, WINDOWS98™, WINDOWS2000™, LINEX-based machine, a MACINTOSH™, Power PC, or a UNIX-based (e.g., SUN™ work station) machine or other common commercially available computer which is known to one of skill. Software for performing, e.g., object grasping, object translocation, or the like is optionally easily constructed by one of skill using a standard programming language such as Visual basic, Fortran, Basic, Java, or the like. Any controller or computer optionally includes a monitor which is often a cathode ray tube ("CRT") display, a flat panel display (e.g., active matrix liquid crystal display, liquid crystal display, etc.), or others. Computer circuitry is often placed in a box (e.g., within the base of the gripper apparatus of the invention), which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard (e.g., a touch screen, etc.) or mouse optionally provide for input from a user.

The computer typically includes appropriate software for receiving user instructions, either in the form of user input into a set of parameter fields, e.g., in a GUI, or in the form of preprogrammed instructions, e.g., preprogrammed for a variety of different specific operations. The software then converts these instructions to appropriate language for instructing the operation of one or more the grasping mechanism, the boom, or the like to carry out the desired operation, e.g., varying or selecting the rate or mode of movement of various system components, or the like. The computer then receives the data from the one or more sensors/detectors included within the apparatus or system, and interprets the data, either provides it in a user understood format, or uses that data to initiate further controller instructions, in accordance with the programming, e.g., such as in monitoring boom location, grasping mechanism location, or the like.

Referring again to FIG. 41, boom 125 is generally capable of about 360 degrees of rotation. In addition, boom 125 typically moves vertically and horizontally, e.g., to align grasping mechanism 205 with selected stations. As used herein, the term "vertical" refers to a plane that is approximately perpendicular a plane of a horizontal or supporting surface. In contrast, the term "horizontal" refers to a plane that is approximately parallel to a plane of a supporting surface and approximately perpendicular a vertical plane. Although many types of robots can be used in robotic gripper apparatus 105, in a preferred embodiment of the invention, a Stäubli RX-60 robot (provided by Stäubli Corporation of South Carolina, U.S.A.), which includes boom 125 and base 145, is utilized. A variety of other robotic instrumentation that is optionally adapted for use with the present invention is available from, e.g., the Zymark Corporation (Zymark Center, Hopkinton, Mass.), which utilize various Zymate systems, which can include, e.g., robotics and fluid handling modules. Similarly, the common ORCA® robot, which is used in a variety of laboratory systems, e.g., for microtiter tray manipulation, is also commercially available, e.g., from Beckman Coulter, Inc. (Fullerton, Calif.).

Boom 125 is configured to extend and retract from base 145. This defines the work perimeter for robotic gripper apparatus 105. Stations (e.g., the centrifuge and fermentation apparatus described above) are positioned within the work perimeter of boom 125 as are hand-off areas or other areas that are configured to support or receive objects grasped and moved by grasping mechanism 205. For example, sample plate 255 is positioned on a station shelf and can be grasped by grasping mechanism 205 and moved to another position by boom 125.

Figure 42:
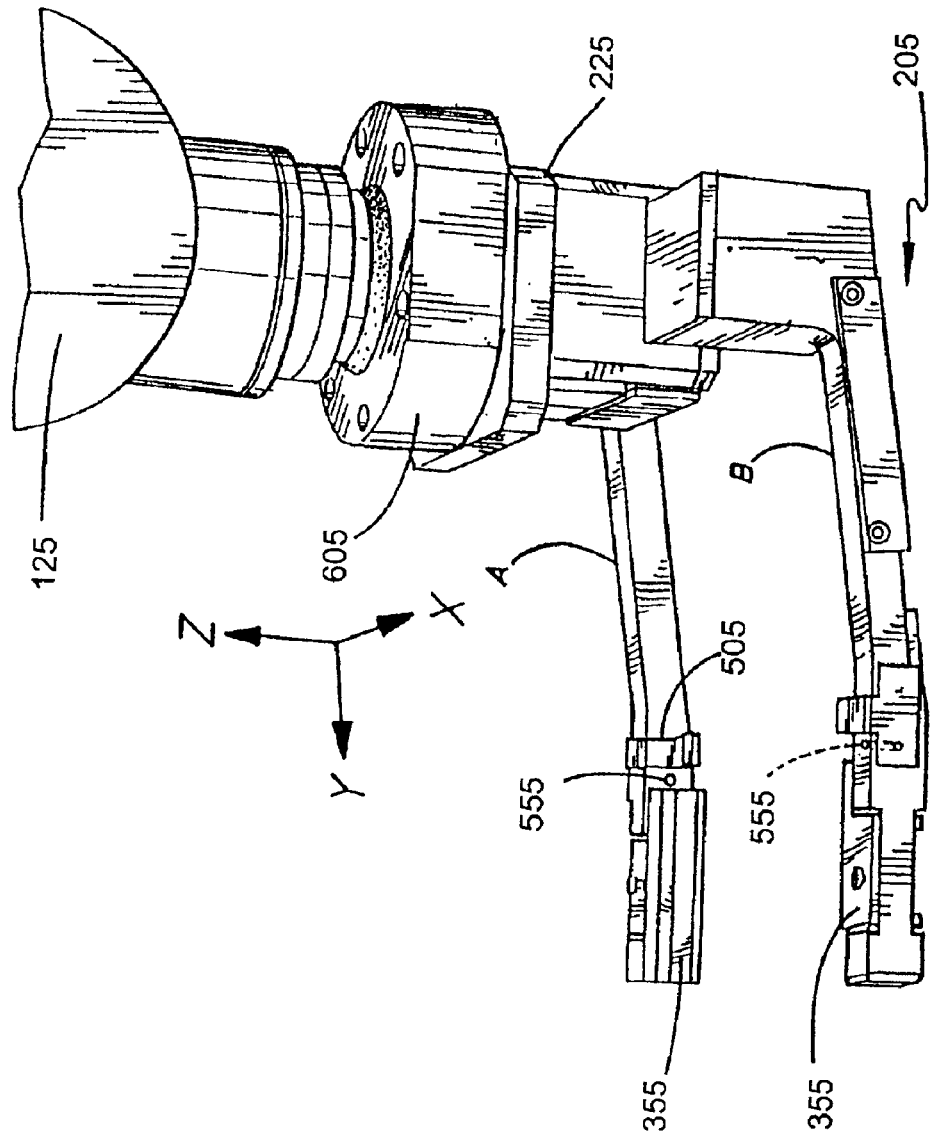
FIG. 42 schematically illustrates one embodiment of a grasping mechanism coupled to a boom of a robot from a perspective view.

Referring now to FIG. 42, one embodiment of grasping mechanism 205 is illustrated. Grasping arm A and grasping arm B extend from gripper mechanism body 225. Although the embodiments described herein include two arms for purposes of clarity of illustration, the grasping mechanisms of the invention optionally include more than two arms, e.g., about three, about four, about five, about six, or more arms. Further, although in preferred embodiments, grasping mechanism arms are structured to grasp objects between the arms, other configurations are also optionally included, e.g., such that certain objects can be at least partially, if not entirely, grasped internally, e.g., via one or more cavities disposed in one or more surfaces of the particular objects.

As further shown in FIG. 42, grasping mechanism body 225 is connected to a deflectable member, such as breakaway 605, which is deflectably coupled to boom 125. Breakaway 605 is typically structured to detect angular, rotational, and compressive forces encountered by grasping mechanism 205. The breakaway acts as a collision protection device that greatly reduces the possibility of damage to components within the work perimeter by, e.g., the accidental impact of grasping mechanism 205 or grasping arms A and B with objects. For example, when grasping mechanism 205 impacts an object, breakaway 605 will deflect, thereby also causing grasping mechanism 205 to deflect. To further illustrate, deflectable members in the apparatus of the invention generally deflect when the grasping mechanism contacts an object or other item with a force greater than a preset force. The preset force typically includes a torque force and/or a moment force that, e.g., ranges between about 1.0 Newton-meter and about 10.0 Newton-meters. When controller 155 detects the deflection, it generally stops movement of the robotic gripper mechanism. In a preferred embodiment, breakaway 605 is a "QuickSTOP™" collision sensor manufactured by Applied Robotics of Glenville, N.Y., U.S.A. Breakaway 605 is typically a dynamically variable collision sensor that operates, e.g., on an air pressure system. Other types of impact detecting devices are optionally employed, which operate hydraulically, magnetically, or by other means known in the art. In certain embodiments, breakaways are not included in the gripper apparatus of the invention. In these embodiments, grasping mechanisms are typically directly coupled to robotic booms.

As also shown, body 225 connects grasping arms A and B to breakaway 605. When directed by controller 155, body 225 moves grasping arms A and B away from or toward each other, e.g., to grasp and release objects. In a preferred embodiment, body 225 is manufactured by Robohand of Monroe, Conn., U.S.A. Typically, the grasping arms are pneumatically driven, but other means for operating the arms are also optionally utilized, such as magnetic- and hydraulic-based systems.

Figure 43:
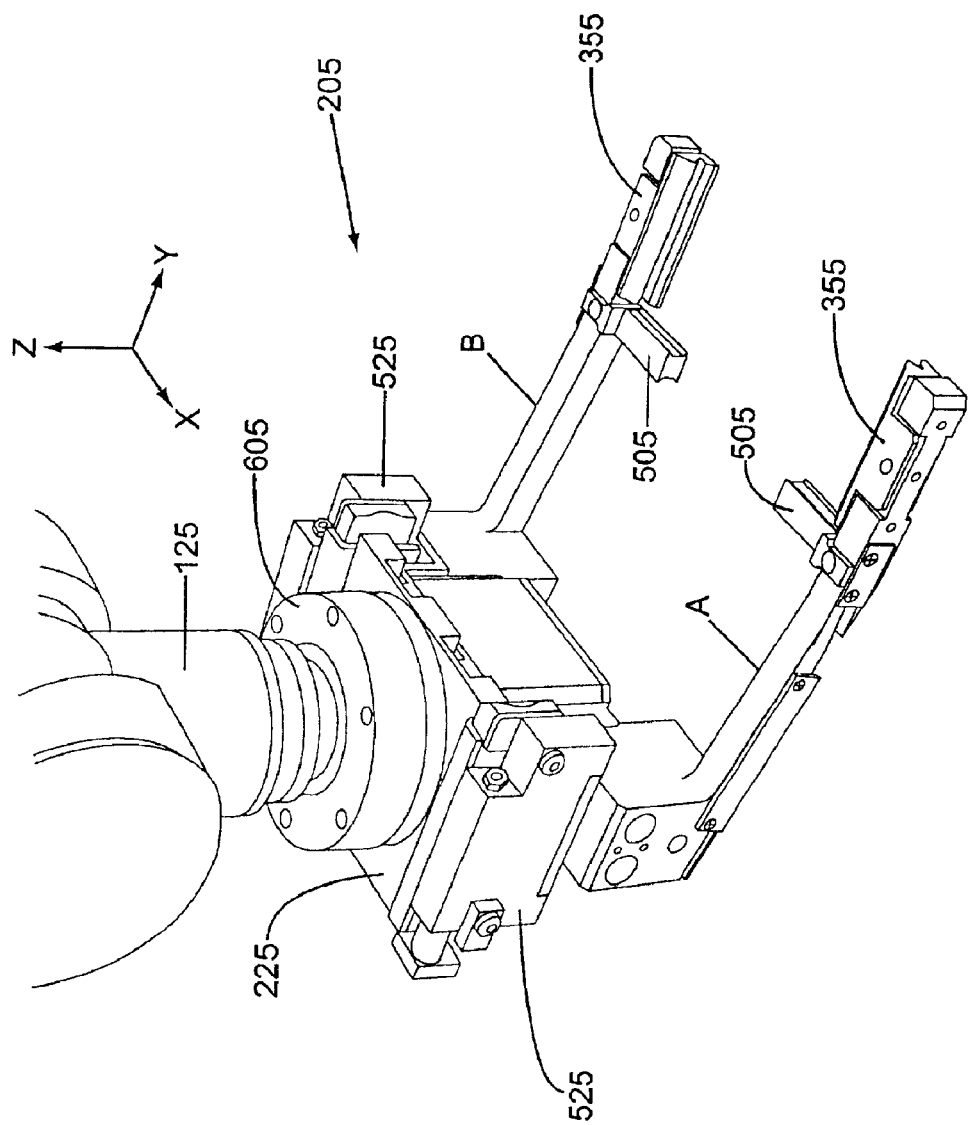
FIG. 43 schematically illustrates another embodiment of a grasping mechanism coupled to a boom of a robot from a perspective view.

In other preferred embodiments, grasping arms are resiliently coupled to robotic booms such that when an object contacts stops on the grasping arms, the arms reversibly recede from an initial position, e.g., to determine a y-axis position of an object prior to determining the x-axis and z-axis positions of the object. One of these embodiments is schematically illustrated in FIG. 43. In particular, FIG. 43 schematically depicts one embodiment of grasping mechanism 205 that includes arms A and B resiliently coupled to body 225 via slideable interface 525. Slideable interfaces typically include springs, which resiliently couple, e.g., grasping arms to grasping mechanism bodies. Such resiliency is optionally provided by other interfaces that include, e.g., pneumatic mechanisms, hydraulic mechanisms, or the like. As further shown, arms A and B include stops 505 and pivot members 355. As mentioned, the embodiment of grasping mechanism 205 schematically illustrated in FIG. 43 is optionally used to determine the y-axis position of an object prior to grasping the object between the arms, that is, prior to determining the x-axis and z-axis positions of the object. As further shown in FIG. 43, grasping mechanism 205 is connected to boom 125 via breakaway 605. Breakaways are described in greater detail above. Optionally, breakaways are not included in the gripper apparatus or systems of the invention, in which case grasping mechanisms, such as grasping mechanism 205 of FIGS. 42 and 43, are directly connected, e.g., to boom 125. Methods that include grasping mechanisms such as the one schematically shown in FIG. 43 are described further below.

Figure 44:
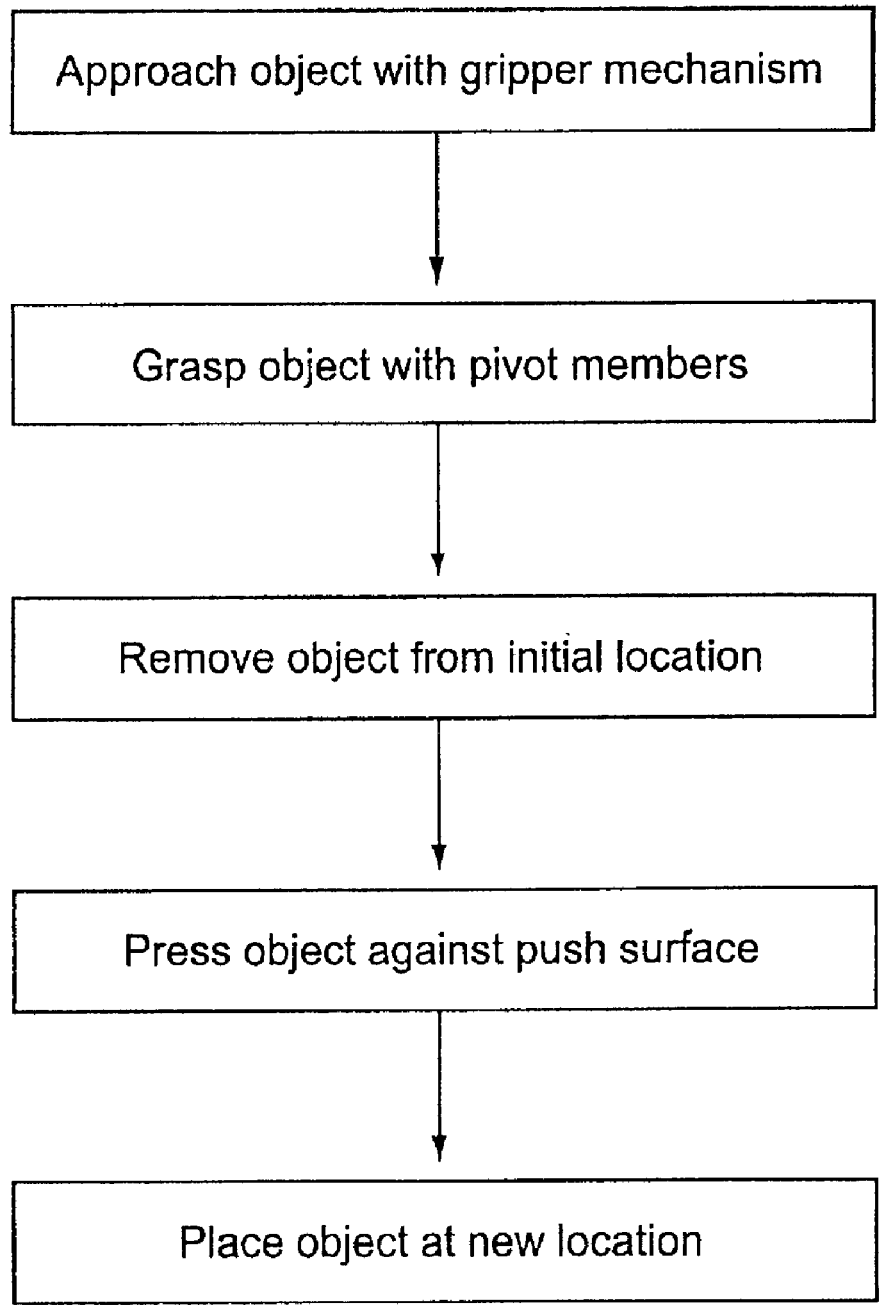
FIG. 44 is a block diagram illustrating one method of grasping an object with a gripper apparatus.

The invention also relates to various methods. For example, the invention provides a method of determining an x-axis position and a z-axis position of an object. The method includes providing a gripper apparatus that includes a controller coupled grasping mechanism including moveably coupled arms that are structured to grasp an object in which at least one arm includes a support surface and a height adjusting surface. The method also includes grasping at least a section of the object with the arms such that the height adjusting surface pushes the object into contact with the support surface, thereby determining the x-axis position and the z-axis position of the object. In some embodiments, one or more of the arms include a stop and the method further includes providing at least one push surface, and pushing the object against the at least one push surface and into contact with the stop using the gripper apparatus, thereby determining a y-axis position of the object. Typically, the object is positioned at an initial position and the method generally further includes removing the object from the initial position with the gripper apparatus and placing the object at a new position with the gripper apparatus. FIG. 44 is a block diagram that further illustrates this process of grasping an object with a gripper apparatus.

Figure 45:
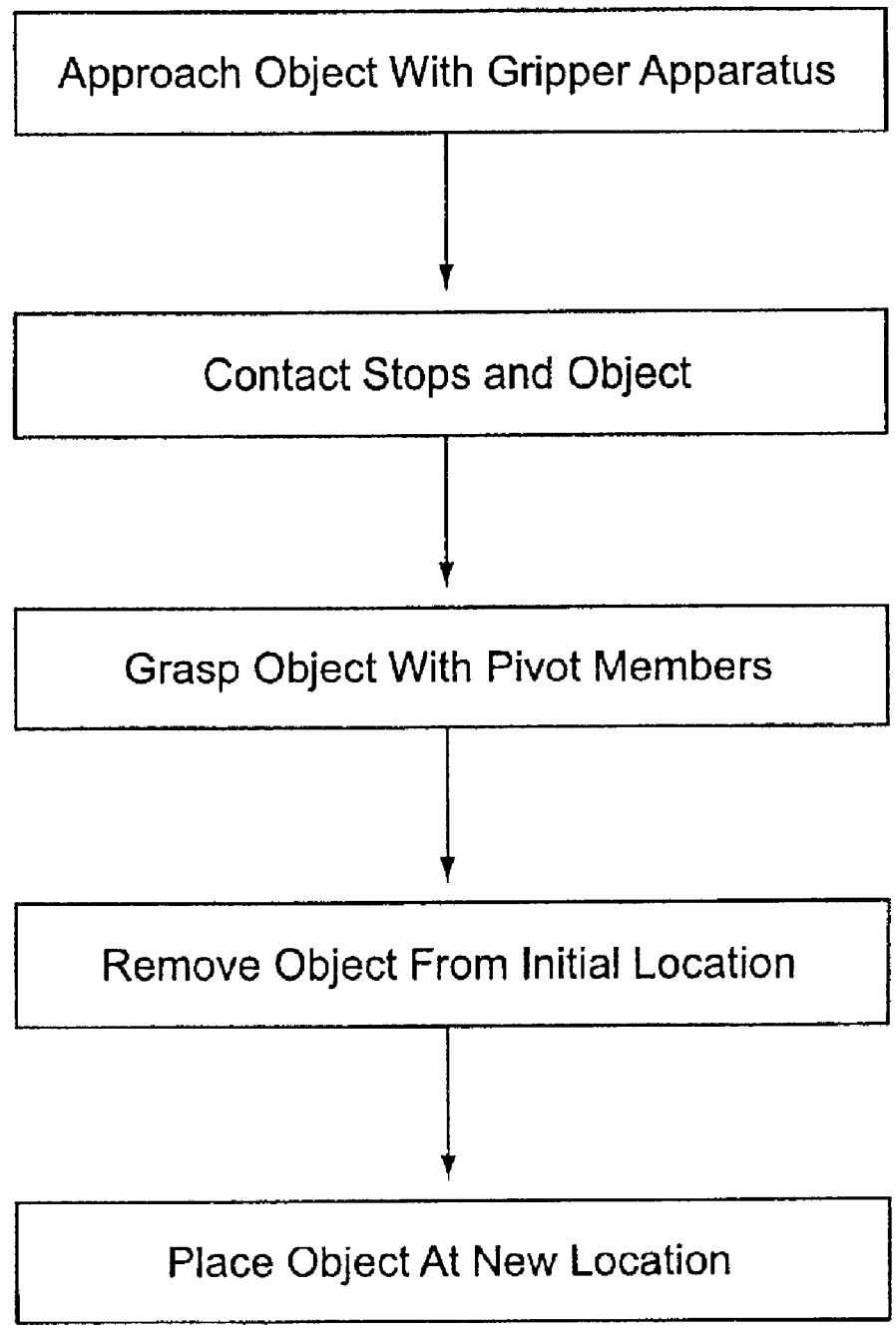
FIG. 45 is a block diagram illustrating another method of grasping an object with a gripper apparatus.

In addition, the invention provides methods that include providing a gripper apparatus that includes a controller coupled grasping mechanism structured to grasp an object with arms that extend from a body of the grasping mechanism in which at least one arm includes a stop. Further, at least two grasping mechanism components are resiliently coupled together (e.g., along a y-axis direction, etc.). To illustrate, in certain embodiments, the arms are resiliently coupled to the body of the grasping mechanism. Optionally, pivot members and/or stops are resiliently coupled to the arms. The methods also include contacting the object is pushed against a push surface by the stops, whereby the resilient coupling allows the arms to reversibly recede from an initial position (e.g., an initial y-axis position, etc.), and grasping at least a section of the object with the arms, after which the arms advance at least substantially back to the initial position, thereby grasping the object. The object is typically positioned at a first position and the method generally further includes removing the object from the first position with the gripper apparatus and placing the object at a second position with the gripper apparatus. FIG. 45 is a block diagram that further illustrates this method of grasping an object such that the y-axis position of the object is determined before the x-axis and z-axis positions of the object.

One skilled in the art will appreciate that the present invention can be practiced by other than the preferred embodiments which are presented in this description for purposes of illustration and not of limitation, and the present invention is limited only by the claims that follow. It is noted that equivalents for the particular embodiments discussed in this description are also within the scope of the present invention.

All patents, patent applications, publications and other documents cited above are incorporated by reference for all purposes as if each patent, patent application, publication and/or other document were specifically indicated to be incorporated by reference.

What is claimed is:

1. A system for processing a plurality of samples comprising:

a first station for performing a plurality of fermentations, each fermentation being performed in a different sample vessel;

a second station comprising a centrifuge for performing a further processing step on the plurality of fermented samples where the sample is retained in the same sample vessel as the fermentation during the further processing step; and, means for crystallizing proteins expressed in the samples.

2. The system of claim 1, wherein the means is capable of crystallizing hundreds of thousands of proteins per day.

3. The system of claim 1, wherein the system further comprises means for performing x-ray crystallography.

4. The system of claim 1, further comprising means for analyzing on an imaging station as many as 1 million images from as many as 140,000 crystallization experiments set up each day.

5. The system of claim 1, further comprising means for identifying crystals with crystal detecting algorithms.

6. The system of claim 1, further comprising means for automatically positioning and centering about 30 to about 50 protein crystals per hour with a robot.

7. The system of claim 1, wherein the crystals are frozen and analyzed by X-ray diffraction.

8. The system of claim 7, wherein the beamline produces diffraction data that is subject to phasing and refinement calculations and is converted to a three dimensional representation of the protein.

9. The system of claim 8, wherein the three dimensional representation of the protein undergoes virtual ligand screening wherein a computerized simulation of the interaction between proteins and potential drugs identifies drug leads for synthesis and/or in vitro and/or in vivo testing.

10. The system of claim 1, wherein the first and/or second station is automated.

11. The system of claim 1, wherein two or more sample vessels are coupled to a gas distribution arrangement.

12. The system of claim 1, wherein one or more components of the system are coupled to a controller that functions to instruct operation of the components.

13. The system of claim 1, further comprising at least one robotic gripper apparatus that is structured to move sample vessels between at least the first and second stations.

14. The system of claim 1, further comprising a sonication device that is insertable into sample vessels.

15. The system of claim 1, wherein two or more sample vessels are held in a carrier.

16. The system of claim 15, wherein the carrier is portable.

* * * * *